(12) United States Patent
Saltzman et al.

(10) Patent No.: US 12,268,774 B2
(45) Date of Patent: Apr. 8, 2025

(54) COMPOSITIONS AND METHODS FOR IN UTERO DELIVERY

(71) Applicant: Yale University, New Haven, CT (US)

(72) Inventors: W. Mark Saltzman, New Haven, CT (US); David H. Stitelman, Branford, CT (US); James Stephen Farrelly, Milford, CT (US); Anthony Bianchi, Liverpool, NY (US)

(73) Assignee: YALE UNIVERSITY, New Haven, CT (US)

( * ) Notice: Subject to any disclaimer, the term of this patent is extended or adjusted under 35 U.S.C. 154(b) by 53 days.

(21) Appl. No.: 18/397,091

(22) Filed: Dec. 27, 2023

(65) Prior Publication Data
US 2024/0207172 A1    Jun. 27, 2024

Related U.S. Application Data

(63) Continuation of application No. 16/603,152, filed as application No. PCT/US2018/026116 on Apr. 4, 2018, now abandoned.

(60) Provisional application No. 62/481,562, filed on Apr. 4, 2017, provisional application No. 62/489,377, filed on Apr. 24, 2017, provisional application No. 62/589,275, filed on Nov. 21, 2017.

(51) Int. Cl.
| | | |
|---|---|---|
| A61K 9/00 | (2006.01) | |
| A61K 9/16 | (2006.01) | |
| A61K 9/51 | (2006.01) | |
| A61K 38/18 | (2006.01) | |
| A61K 47/60 | (2017.01) | |
| A61K 48/00 | (2006.01) | |
| A61P 7/00 | (2006.01) | |
| A61P 11/00 | (2006.01) | |

(52) U.S. Cl.
CPC .......... *A61K 9/0034* (2013.01); *A61K 9/0019* (2013.01); *A61K 9/1647* (2013.01); *A61K 9/1652* (2013.01); *A61K 9/5153* (2013.01); *A61K 38/1825* (2013.01); *A61K 47/60* (2017.08); *A61K 48/0041* (2013.01); *A61P 7/00* (2018.01); *A61P 11/00* (2018.01)

(58) Field of Classification Search
None
See application file for complete search history.

(56) References Cited

U.S. PATENT DOCUMENTS

| | | |
|---|---|---|
| 3,266,987 A | 8/1966 | Crowley |
| 3,832,253 A | 8/1974 | Palma |
| 3,854,480 A | 12/1974 | Zaffaroni |
| 4,452,775 A | 6/1984 | Kent |
| 4,460,563 A | 7/1984 | Calanchi |
| 4,667,013 A | 5/1987 | Reichle |
| 4,675,189 A | 6/1987 | Kent |
| 4,714,680 A | 12/1987 | Civin |
| 4,748,034 A | 5/1988 | Rham |
| 4,794,000 A | 12/1988 | Ecanow |
| 4,883,666 A | 11/1989 | Sabel |
| 4,965,204 A | 10/1990 | Civin |
| 5,034,506 A | 7/1991 | Summerton |
| 5,061,620 A | 10/1991 | Tsukamoto |
| 5,075,109 A | 12/1991 | Tice |
| 5,114,719 A | 5/1992 | Sabel |
| 5,118,528 A | 6/1992 | Fessi |
| 5,133,974 A | 7/1992 | Paradissis |
| 5,142,047 A | 8/1992 | Summerton |
| 5,176,996 A | 1/1993 | Hogan |
| 5,185,444 A | 2/1993 | Summerton |
| 5,239,660 A | 8/1993 | Ooi |
| 5,354,670 A | 10/1994 | Nickoloff |
| 5,356,802 A | 10/1994 | Chandrasegaran |
| 5,407,686 A | 4/1995 | Patel |
| 5,422,251 A | 6/1995 | Fresco |
| 5,436,150 A | 7/1995 | Chandrasegaran |
| 5,487,994 A | 1/1996 | Chandrasegaran |
| 5,527,675 A | 6/1996 | Coull |
| 5,539,082 A | 7/1996 | Nielsen |
| 5,601,835 A | 2/1997 | Sabel |
| 5,623,049 A | 4/1997 | Lobberding |
| 5,643,741 A | 7/1997 | Tsukamoto |
| 5,665,541 A | 9/1997 | Miller |
| 5,677,136 A | 10/1997 | Simmons |
| 5,698,546 A | 12/1997 | Bridger |
| 5,714,331 A | 2/1998 | Buchardt |
| 5,716,827 A | 2/1998 | Tsukamoto |

(Continued)

FOREIGN PATENT DOCUMENTS

| | | |
|---|---|---|
| EP | 0253193 | 1/1988 |
| EP | 0266099 | 5/1988 |

(Continued)

OTHER PUBLICATIONS

Khaboushan et al., Stem Cell Reviews and Reports, 2022, 18: 752-767.*
Watanabe et al., Tissue Engineering, 2011, 17: 1099-1110.*
Wiltsey et al., Acta Biomaterialia, 2015, 16: 71-80.*
Watanabe et al., Tissue Engineering: Part A, 2010, 16: 1645-1655.*
Chandrasekar et al., Food Hydrocolloids, 2017, 69: 301-307.*
Formiga et al., J. Conrol. Rel., 2014, 173: 132-139.*
Zhou et al., Int. J. Pharm., 2009, 37: 197-195.*

(Continued)

*Primary Examiner* — Ileana Popa
(74) *Attorney, Agent, or Firm* — PABST PATENT GROUP LLP

(57) ABSTRACT

Compositions and methods for fetal or in utero delivery of active agents are provided. The compositions are most typically administered intravenously via the vitelline vein, umbilical vein, or directly into the amniotic cavity of a pregnant mother. Fibroblast growth factor is to correct structural defects of neural tissue.

13 Claims, 2 Drawing Sheets

(56) References Cited

U.S. PATENT DOCUMENTS

| | | |
|---|---|---|
| 5,736,152 A | 4/1998 | Dunn |
| 5,736,336 A | 4/1998 | Buchardt |
| 5,739,308 A | 4/1998 | Kandimalla |
| 5,750,397 A | 5/1998 | Tsukamoto |
| 5,759,793 A | 6/1998 | Schwartz |
| 5,773,571 A | 6/1998 | Nielsen |
| 5,776,744 A | 7/1998 | Glazer |
| 5,786,461 A | 7/1998 | Buchardt |
| 5,786,571 A | 7/1998 | Bethel |
| 5,854,033 A | 12/1998 | Lizardi |
| 5,866,361 A | 2/1999 | Dujon |
| 5,932,711 A | 8/1999 | Boles |
| 5,945,337 A | 8/1999 | Brown |
| 5,962,426 A | 10/1999 | Glazer |
| 6,010,908 A | 1/2000 | Gruenert |
| 6,140,081 A | 10/2000 | Barbas |
| 6,261,841 B1 | 7/2001 | Cohen |
| 6,303,376 B1 | 10/2001 | Glazer |
| 6,326,479 B1 | 12/2001 | Gildea |
| 6,331,617 B1 | 12/2001 | Weeks |
| 6,363,746 B1 | 4/2002 | Wei |
| 6,422,251 B1 | 7/2002 | Tseng |
| 6,441,130 B1 | 8/2002 | Egholm |
| 6,453,242 B1 | 9/2002 | Eisenberg |
| 6,509,323 B1 | 1/2003 | Davis |
| 6,534,261 B1 | 3/2003 | Cox |
| 6,610,512 B1 | 8/2003 | Barbas |
| 6,632,919 B1 | 10/2003 | Nielsen |
| 6,686,463 B2 | 2/2004 | Beigelman |
| 6,746,838 B1 | 6/2004 | Choo |
| 6,770,442 B2 | 8/2004 | Gildea |
| 6,866,997 B1 | 3/2005 | Choo |
| 6,919,208 B2 | 7/2005 | Levy |
| 7,067,617 B2 | 6/2006 | Barbas |
| 7,078,389 B2 | 7/2006 | Glazer |
| 7,256,275 B2 | 8/2007 | Coull |
| 7,279,463 B2 | 10/2007 | Glazer |
| 7,534,448 B2 | 5/2009 | Saltzman |
| 7,534,449 B2 | 5/2009 | Saltzman |
| 7,550,154 B2 | 6/2009 | Saltzman |
| 7,566,535 B2 | 7/2009 | Kmiec |
| 8,309,356 B2 | 11/2012 | Glazer |
| 8,658,608 B2 | 2/2014 | Glazer |
| 8,889,117 B2 | 11/2014 | Mellman |
| 9,193,758 B2 | 11/2015 | Ly |
| 9,220,698 B2 | 12/2015 | Ault |
| 9,272,043 B2 | 3/2016 | Saltzman |
| 9,317,102 B2 | 4/2016 | Kanchana |
| 9,501,364 B1 | 11/2016 | Bushman |
| 9,501,365 B2 | 11/2016 | Nitin |
| 9,526,136 B1 | 12/2016 | Ramabhadran |
| 9,617,074 B2 | 4/2017 | Hellenbrand |
| 9,834,945 B2 | 12/2017 | Crumley |
| 11,136,597 B2 | 10/2021 | Saltzman |
| 2002/0165356 A1 | 11/2002 | Barbas |
| 2003/0044978 A1 | 3/2003 | Young |
| 2003/0113894 A1 | 6/2003 | Selden |
| 2003/0148352 A1 | 8/2003 | Glazer |
| 2003/0211612 A1 | 11/2003 | Seidman |
| 2004/0006035 A1 | 1/2004 | Macejak |
| 2004/0197892 A1 | 10/2004 | Moore |
| 2004/0241651 A1 | 12/2004 | Olek |
| 2006/0045874 A1 | 3/2006 | Bedwell |
| 2007/0154989 A1 | 7/2007 | Barbas |
| 2007/0213269 A1 | 9/2007 | Barbas |
| 2007/0219122 A1 | 9/2007 | Glazer |
| 2008/0050920 A1 | 2/2008 | Kawahara |
| 2009/0239789 A1 | 9/2009 | Saltzman |
| 2009/0269397 A1 | 10/2009 | Saltzman |
| 2010/0151436 A1 | 6/2010 | Fong |
| 2010/0172882 A1 | 7/2010 | Glazer |
| 2011/0008451 A1 | 1/2011 | Saltzman |
| 2011/0145940 A1 | 6/2011 | Voytas |
| 2011/0262406 A1 | 10/2011 | Campo |
| 2011/0268810 A1 | 11/2011 | Saltzman |
| 2011/0293585 A1 | 12/2011 | Del Campo |
| 2014/0128570 A1 | 5/2014 | Ly |
| 2014/0255384 A1 | 9/2014 | Frey, II |
| 2014/0342003 A1 | 11/2014 | Saltzman |
| 2015/0057505 A1 | 2/2015 | Bangera |
| 2015/0073041 A1 | 3/2015 | Saltzman |
| 2015/0118311 A1 | 4/2015 | Zhou |
| 2015/0125384 A1 | 5/2015 | Mellman |
| 2016/0251477 A1 | 9/2016 | Cui |
| 2016/0263875 A1 | 9/2016 | Ueno |
| 2017/0000737 A1 | 1/2017 | Deng |
| 2017/0266119 A1 | 9/2017 | Deng |
| 2017/0283830 A1 | 10/2017 | Saltzman |
| 2020/0113821 A1 | 4/2020 | Saltzman |
| 2020/0308590 A1 | 10/2020 | Glazer |

FOREIGN PATENT DOCUMENTS

| | | |
|---|---|---|
| EP | 0375408 | 6/1990 |
| EP | 2754684 | 7/2014 |
| EP | 3388517 | 10/2018 |
| GB | 929401 | 6/1963 |
| WO | 9220698 | 11/1992 |
| WO | 93012096 | 6/1993 |
| WO | 9317102 | 9/1993 |
| WO | 93017102 | 9/1993 |
| WO | 95001364 | 1/1995 |
| WO | 95013650 | 1/1995 |
| WO | 1995001364 | 1/1995 |
| WO | 9526136 | 10/1995 |
| WO | 9602558 | 2/1996 |
| WO | 96039195 | 2/1996 |
| WO | 1996004000 | 2/1996 |
| WO | 9617074 | 6/1996 |
| WO | 96017074 | 6/1996 |
| WO | 9640271 | 12/1996 |
| WO | 96040898 | 12/1996 |
| WO | 9834945 | 8/1998 |
| WO | 98034945 | 8/1998 |
| WO | 98053059 | 11/1998 |
| WO | 0022113 | 4/2000 |
| WO | 0022114 | 4/2000 |
| WO | 0125419 | 4/2001 |
| WO | 2002010142 | 2/2002 |
| WO | 2003016496 | 2/2003 |
| WO | 2003052071 | 6/2003 |
| WO | 2005108622 | 11/2005 |
| WO | 2008086529 | 7/2008 |
| WO | 2010123983 | 10/2010 |
| WO | 2011053989 | 5/2011 |
| WO | 2011072246 | 6/2011 |
| WO | 2011133802 | 10/2011 |
| WO | 2011133803 | 10/2011 |
| WO | 2012085554 | 6/2012 |
| WO | 2012138955 | 10/2012 |
| WO | 2013082529 | 6/2013 |
| WO | 2013176772 | 11/2013 |
| WO | 2014018423 | 6/2014 |
| WO | 2014110020 | 7/2014 |
| WO | 2015148716 | 10/2015 |
| WO | 2015172149 | 11/2015 |
| WO | 2015172153 | 11/2015 |
| WO | 2016081621 | 5/2016 |
| WO | 2016183209 | 11/2016 |
| WO | 2016183217 | 11/2016 |
| WO | 2017143042 | 8/2017 |
| WO | 2017143061 | 8/2017 |
| WO | 2018175927 | 9/2018 |
| WO | 2018187493 | 10/2018 |

OTHER PUBLICATIONS

Oshiro et al., Int. J. Polym. Sci., 2015, pp. 1-7.*
Murata, et al., "Anti-tumor effects of anti-VEGF siRNA encapsulated with PLGA microspheres in mice", J. Control. Release, 126(3):246-54 (2008).
Capecchi, "Altering the genome by homologous recombination," Science 244(4910): 1288-1292 (1989).

(56) References Cited

OTHER PUBLICATIONS

Orson, et al., "Oligonucleotide inhibition of IL2R alpha mRNA transcription by promoter region collinear triplex formation in lymphocytes", Nucleic Acids Res. 19:3435-41 (1991).
Goncz, et al., "Small fragment homologous replacement-mediated modification of genomic beta-globin sequences in human hematopoietic stem/progenitor cells", Oligonucleotides, 16:213-24 (2006).
Jagodzinski, "Enhanced human immunodeficiency virus infection in macrophages by high-molecular-weight dextran sulfate is associated with conformational changes of gp120 and expression of the CCR5 receptor", Viral Immunol, 12:23 (1999).
Sancar, "DNA excision repair," Annu. Rev. Biochem. 65: 43-81 (1996).
Sterchak, et al., "Uncharged stereoregular nucleic acid analogs. 1. Synthesis of a cytosine-containing oligomer with carbamate internucleoside linkages", Organic Chem., 52:4202-6 (1987).
Warren, et al., Coordinated Transcription-Dependent Redistribution, Journal of Cellular Biochemistry, Supplement 21B:141 (1995).
Abes, et al., "Endosome trapping limits the efficiency of splicing correction by PNA-oligolysine conjugates", J. Controll. Rel., 110:595-604 (2006).
Allison, et al., "The C-Terminal Domain of the Largest Subunit of RNA Polymerase II of *Saccharomyces cerevisiae, Drosophila Melanogaster*, and Mamals: A Conserved Structure with an Essential Function", Molecular and Cellular Biology, 8(1):321-329 (1988).
Asensio, et al., "The Contribution of Cytosine Protonation to the Stability of Parallel DNA Triple Helices", J. Mol. Biol., 275(5): 811-822 (1998b).
Baron, et al., "Localization of the Centrin-Related 165,000-M.sub.r Protein of PtK.sub.2 Cells During the Cell Cycle," Cell Motil. and the Cytoskel. 18:1-14 (1991).
Baumann, et al., "Role of the human RAD51 protein in homologous recombination and double-stranded-break repair", Trends Biochem Sci, 23(7):247-251 (1998).
Belousov, et al., "Triplex targeting of a native gene in permeabilized intact cells: covalent modification of the gene for the chemokine receptor CCR5", Nucleic Acids Res., 26(5): 1324-1328 (1998).
Bennett and Davis, "Erythrocyte ankyrin: Immunoreactive analogues are associated with mitotic structures in cultured cells and with microtubules in brain", Proc. Natl. Acad. Sci. USA., 78:7550-7554 (1981).
Braasch, et al., "Locked nucleic acid (LNA): fine-tuning the recognition of DNA and RNA", Chem. Biol., 8(1):1-7 (2001).
Bredberg, et al., "Psoralen adducts in a shuttle vector plasmid propagated in primate cells: high mutagenicity of DNA cross-links", Carcinogenesis, 8(12):1923-1927 (1987).
Brenneman, et al., "Stimulation of intrachromosomal homologous recombination in human cells by electroporation with site-specific endonucleases", Proc. Natl. Acad. Sci. USA, 93(8):3608-3612 (1996).
Carrington, et al., "Novel alleles of the chemokine-receptor gene CCR5.", Am. J. Hum. Genet., 61:1261-1267 (1997).
Chan, et al., "Targeted correction of an episomal gene in mammalian cells by a short DNA fragment tethered to a triplex-forming oligonucleotide", J. Biol. Chem., 274(17):11541-11548 (1999).
Chen, et al., "Ethyl carbamate metabolism: in vivo inhibitors and in vitro enzymatic systems.", Drug Metab. Dispos., 18:815 (1990).
Chen, et al., "In Vivo Expression of Single-Stranded DNA in Mammalian Cells with DNA Enzyme Sequences Targeted to C-raf," Antisense Nucleic Acid Drug Dev. 10:415-422 (2000).
Cuenoud, et al., "Dual recognition of double-stranded DNA by 2'-aminoethoxy-modified oligonucleotides", Angew. Chem. Int. Ed., 37:1288-1291 (1998).
Dagle, et al., "Positively charged oligonucleotides overcome potassium-mediated inhibition of triplex DNA formation", Nucleic Acids Res., 24(11):2143-9 (1996).
Dahmus, "Phosphorylation of Eukaryotic DNA-dependent RNA Polymerase", J. Biol. Chem., 256:3332-3339 (1981).
Datta, et al., "Triplex-induced Recombination in Human Cell-free Extracts," J. Biol. Chem., 276:18018-18023 (2001).
Egholm, et al., "Efficient pH-independent sequence-specific DNA binding by pseudoisocytosine-containing bis-PNA.", Nucl. Acids Res., 23(2):217-222 (1995).
Fakan & Bernhard, "Localization of Rapidly and Slowly Labelled Nuclear RNA as Visualized by High Resolution Autoradiography," Exp. Cell Res. 67:129-141 (1971).
Fakan & Puvion, "The Ultrastructural Visualization of Nucleolar and Extranucleolar RNA Synthesis and Distribution," Int. Rev. Cytol . . . 65:255-99 (1980).
Fakan, et al., "Localization and Characterization of Newly Synthesized Nuclear RNA in Isolated Rat Hepatocytes," Exp. Cell. Res. 99:155-164 (1976).
Faria, et al., "Targeted Inhibition of Transcription Elongation in Cells Mediated by Triplex-Forming Oligonucleotides," Proc. Natl. Acad. Sci. USA, 97: 3862-3867 (2000).
Faruqi, et al., "Triple-helix formation induces recombination in mammalian cells via a nucleotide excision repair-dependent pathway", Mol. Cell. Bio., 20(3):990-1000 (2000).
Gasparro, et al., "Photoactivatable antisense DNA: suppression of ampicillin resistance in normally resistant *Escherichia coli*.," Antisense Res. Dev. 1:117-140 (1991).
Gasparro, et al., "Site-specific targeting of Psoralen Photoadducts with a Triple Helix-Forming Oligonucleotide: Characterization of Psoralen Monoadduct and Crosslink Formation", Nucl. Acids Res., 22(14):2845-2852 (1994).
Gasparro, et al., "Rapid and sensitive analysis of 8-methoxypsoralen in plasma," J. Invest. Derm., 90:234-236 (1988).
Gerace, et al., "Immunocytochemical Localization of the Major Polypeptides of the Nuclear Pore Complex—Lamina Fraction", J. Cell Biol., 79:546-566 (1978).
Gia, et al., "Sequence specificity of psoralen photobinding to DNA: a quantitative approach," Biochemistry 31:11818-11822 (1992).
Giovannangeli, et al., "Triplex-forming molecules for modulation of DNA information processing," Curr. Opin. Mol. Ther. 2(3): 288-296 (2000).
Glazer, et al., "Detection and Analysis of UV-induced Mutations in Mammalian Cell DNA Using A Phage Suttle Vector", Proc. Natl. Acad. Sci., 83:1041-1044 (1986).
Goncz, et al., "Site-directed alteration of genomic DNA by small-fragment homologous replacement", Methods Mol. Biol., 133:85-89 (2000).
Gordenin, et al., "Yeast ARMs (DNA at-risk motifs) can reveal sources of genome instability.", Mutat. Res., 400(1-2):45-58 (1998).
Gorman, et al., "Stable Alteration of Pre-mRNA Splicing Patterns by Modified U7 Small Nuclear RNAs," Proc. Natl. Acad. Sci. USA, 95: 4929-4934 (1998).
Grigoriev, et al., "Oligodeoxynucleotide-directed Photo-induced Cross-linking of HIV Proviral DNA via Triple-helix Formation," Nucleic Acids Research, 20(16):4275-4281 (1992A).
Hanson, et al., "Analysis of biological selections for high-efficiency gene targeting", Mol. Cell. Biol., 15(1):45-51 (1995).
Harding, "NMR Studies on YSPTSPSY: Implications for the Design of DNA Bisintercalators," Journal of Medicinal Chemistry, 35:4658-4664 (1992).
Hartley, et al., "Electrophoretic and chromatographic separation methods used to reveal interstrand crosslinking of nucleic acids", J. Chromatogr., 618(1-2):277-88 (1993).
Havre & Glazer, "Targeted mutagenesis of simian virus 40 DNA mediated by a triple helix-forming oligonucleotide", J. Virol., 67(12):7324-7331 (1993a).
Havre, et al., "Targed Mutagenesis of DNA Using Triple Helix-forming Oligonucleotides Linked to Psoralen", Proc. Natl. Acad. Sci. USA, 90(16):7879-7883 (1993b).
Helene, "Sequence-selective recognition and cleavage of double-helical DNA", Curr. Opinion Biotechnology, 4:29-36 (1993).
Helene, et al., "The anti-gene strategy: control of gene expression by triplex-forming-oligonucleotides," Anticancer Drug Des. 6(6):569-84 (1991).
Henry & Hodge, "Nuclear Matrix: A Cell-Cycle-Dependent Site of Increased Intranuclear Protein Phosphorylation," Eur. J. Biochem. 133:23-29 (1983).
Hirt, et al., "Selective extraction of polyoma DNA from infected mouse cell cultures" J. Mol. Biol. 26:365-369 (1967).

(56) References Cited

OTHER PUBLICATIONS

Huang, et al., "Functional silencing of hepatic microsomal glucose-6-phosphatase gene expression in vivo by adenovirus-mediated delivery of short hairpin RNA", FEBS Lett., 558(1-3):69-73 (2004).
Iverson, et al., "In vivo studies with phosphorothioate oligonucleotides: pharmacokinetics prologue," Anticancer Drug Des. 6(6):531-8 (1991).
Jackson, et al., "Visualization of focal sites of transcription within human nuclei", EMBO, 12:1059-1065 (1993).
Jakubczak, et al., "Analysis of genetic instability during mammary tumor progression using a novel selection-based assay for in vivo mutations in a bacteriophage lambda transgene target", Proc. Natl. Acad. Sci. USA, 93:9073-9078 (1996).
James, et al., "Towards gene-inhibition therapy: a review of progress and prospects in the field of antiviral antisense nucleic acids and ribozymes", Antiviral Chemistry & Chemotherapy, 2:191-214 (1991).
Jepsen, et al., "LNA-antisense rivals siRNA for gene silencing", Curr. Opin. Drug Discov. Devel., 7(2):188-194 (2004).
Khiat, et al., "Structural Differences Between the Free and Bound States of DNA-Bisintercalating Peptide YSPTSPSY", Journal of Medicinal Chemistry, 39(21):2495 (1996).
Kitagawa, et al., "Enzyme coupled immunoassay of insulin using a novel coupling reagent.", J. Biochem., 79:233-236 (1976).
Koppelhus, et al., "Cellular delivery of peptide nucleic acid (PNA)" Adv. Drug Deliv. Rev., 55(2):267-280 (2003).
Kuhn, et al., "An experimental study of mechanism and specificity of peptide nucleic acid (PNA) binding to duplex DNA.", J. Mol. Biol., 286(5):1337-1345 (1999).
Lacroix, et al., "Triplex formation by oligonucleotides containing 5-(1-propynyl)-2'-deoxyuridine: decreased magnesium dependence and improved intracellular gene targeting", Biochemistry, 38(6):1893-1901(1999).
Laemmli, "Cleavage of Structural Proteins during the Assembly of the Head of Bacteriophage T4", Nature, 227:680-685 (1970).
Lassner, et al., "Targeting of T7 RNA polymerase to tobacco nuclei mediated by an SV40 nuclear location signal", Plant Mol Biol., 17(2):29-34 (1991).
Lee and Greenleaf, "A protein kinase that phosphorylates the C-terminal repeat domain of the largest subunit of RNA polymerase II," Proc. Natl. Acad. Sci. U.S.A. 86:3624-28 (1989).
Letai, et al., "Specificity in formation of triple-stranded nucleic acid helical complexes: studies with agarose-linked polyribonucleotide affinity columns", Biochemistry, 27:9108-9112 (1988).
Lin, et al., "Repair of double-stranded DNA breaks by homologous DNA fragments during transfer of DNA into mouse L Cells," Molecular and Cellular Biology 10:113-119 (1990).
Lin, et al., "Extrachromosomal recombination in mammalian cells as studied with single- and double-stranded DNA substrates", Mol. Cell. Biol., 7(1):129-140 (1987).
Lind, et al., "Structural characteristics of 2'-O-(2-methoxyethyl)-modified nucleic acids from molecular dynamics simulations", Nucleic Acids Res., 26(16):3694-799 (1998).
Liu, et al., "New procedures for preparation and isolation of conjugates of proteins and a synthetic copolymer of D-amino acids and immunochemical characterization of such conjugates.", Biochem., 18:690-693 (1979).
Luo, et al., "High-frequency intrachromosomal gene conversion induced by triplex-forming oligonucleotides microinjected into mouse cells", Proc. Natl. Acad. Sci. U.S.A., 97(16):9003-9008 (2000).
Ma, et al., "Nuclease-resistant external guide sequence-induced cleavage of target RNA by human ribonuclease P", Antisense Nucleic Acid Drug Dev., 8(5):415-26 (1998).
Majumdar, et al., "Cell cycle modulation of gene targeting by a triple helix-forming oligonucleotide", J. Biol. Chem., 278(13):11072-7 (2003A).
Majumdar, et al., "Targeted gene knockout mediated by triple helix forming oligonucleotides", Nat. Genet., 20:212-214 (1998).
Mergny, et al., "Sequence specificity in triple-helix formation: experimental and theoretical studies of the effect of mismatches on triplex stability.", Biochemistry, 30(40):9791-9798 (1991).

Mirabelli, et al., "In Vitro and in vivo pharmacologic activities of antisense oligonucleotides", Anticancer Design, 6:647-661 (1991).
Myhr, "Validation studies with Muta Mouse: a transgenic mouse model for detecting mutations in vivo", Environ. Mol. Mutagen, 18:308-315(1991).
Narayanan, et al., "Elevated levels of mutation in multiple tissues of mice deficient in the DNA mismatch repair gene Pms2", Proc. Natl. Acad. Sci. USA, 94:3122-3127 (1997).
Nickerson, et al., "A Normally Masked Nuclear Matrix Antigen That Appears at Mitosis on Cytoskeleton Filaments Adjoining Chromosomes, Centrioles, and Midbodies", J. Cell. Biol., 116:977-987 (1992).
Noonberg, et al., "In Vivo Generation of Highly Abundant Sequence-Specific Oligonucleotides for Antisense and Triplex Gene Regulation," Nucleic Acids Res., 22:2830-2836 (1994).
Nyce and Metzger, "DNA antisense therapy for asthma in an animal model", Nature, 385(6618):721-5 (1997).
Obika, et al., "2'-O,4'-C-Methylene bridged nucleic acid (2',4'-BNA): synthesis and triplex-forming properties", Bioorg. Med. Chem., 9(4):1001-1011 (2001).
O'Keefe, et al., "Disruption of Pre-mRNA Splicing In Vivo Results in Reorganization of Slicing Factors", J. Cell Biol., 124:249-260 (1994).
Park, et al., "Formation of a ternary complex by human XPA, ERCC1, and ERCC4(XPF) excision repair proteins", Proc. Natl. Acad. Sci. USA, 91:5017-5021 (1994).
Pattanayek, et al., "Structural rationalization of a large difference in RNA affinity despite a small difference in chemistry between two 2'-O-modified nucleic acid analogues", J. Am. Chem. Soc., 126(46):15006-15007 (2004).
Postel, et al., "Evidence that a triplex-forming oligodeoxyribonucleotide binds to the c-myc promoter in Hela cells, thereby reducing c-myc mRNA levels.", Proc. Natl. Acad. Sci. USA, 88(18):8227-8231 (1991).
Price & Pettijohn, "Redistribution of the Nuclear Mitotic Apparatus Protein (NuMA) during Mitosis and Nuclear Assembly", Exp. Cell Res., 166:292-311 (1986).
Puri, et al., "Minimum number of 2'-O-(2-aminoethyl) residues required for gene knockout activity by triple helix forming oligonucleotides", Biochemistry, 41(24):7716-7724 (2002).
Raha, et al., "Mutagenesis by Third-Strand-Directed Psoralen Adducts in Repair-Deficient Human Cells: High Frequency and Altered Specgrum in a Xeroderma Pigmentosum Variant," Proc. Natl. Acad. Sci. USA, 93(7):2941-2942 (1996).
Roberts, et al., "Stability and Properties of Double and Triple Helices: Dramatic Effects of RNA or DNA Backbone Composition," Science 258: 1463-1466 (1992).
Rooney and Moore, "Antiparallel, intramolecular triplex DNA stimulates homologous recombination in human cells," Proc. Natl. Acad. Sci. USA, 92:2141-2144 (1995).
Sambrook, et al., Molecular Cloning: A Laboratory Manual, second edition, Cold Spring Harbor Laboratory Press: New York (1989).
Seipel, et al., "Basal Components of the Transcription Apparatus (RNA Polymerase II, TATA-binding Protein) Contain Activation Domains: Is Repetitive C-Terminal Domain (CTD) of RNA Polymerase II a Portable Enhancer Domain?", Chemical Abstracts, 122(17), Abstract No. 206769 (1994).
Shevelev, et al., "Potential Triple Helix-Mediated Inhibition of IGF-I Gene Expression Significantly Reduces Tumorigenicity of Gliolastoma in an Animal Model," Cancer Gene Therapy, 4:105-112 (1997).
Sibghat-Ullah, et al., "Human nucleotide excision repair in vitro: repair of pyrimidine dimers, psoralen and cisplatin adducts by HeLa cell-free extract", Nucl. Acids Res., 17:4471-4484 (1989).
Sidransky, et al., "Identification of p53 gene mutations in bladder cancers and urine samples.", Science 252:706-709 (1991).
Singleton and Dervan, "Influence of pH on the Equilibrium Association Constants for Oligodeoxyribonucleotide-Directed Triple Helix Formation at Single DNA Sites", Biochemistry, 31:10995-11003 (1992).

(56) References Cited

OTHER PUBLICATIONS

Smith, et al., "Alterations in chromatic Conformation Are Accompanies by Reorganization of Nonchromatin Domains That Contain U-snRNP Protein p28 and Nuclear Protein p107", J. Cell. Biol., 101:560-567 (1985).
Steinberger, et al., "Functional deletion of the CCR5 receptor by intracellular immunization produces cells that are refractory to CCR5-dependent HIV-1 infection and cell fusion.", Proc. Natl. Acad. Sci. USA., 97(2):805-810 (2000).
Takasugi, et al., "Sequence-specific photo-induced cross-linking of the two strands of double-helical DNA by a psoralen covalently linked to a triple helix-forming oligonucleotide.", Proc. Natl. Acad. Sci. USA, 88(13):5602-5606 (1991).
Talmadge, "The pharmaceutics and delivery of therapeutic polypeptides and proteins", Adv. Drug Del. Rev., 10:247-299 (1993).
Thibodeau and Vincent, "Monoclonal Antibody CC-3 Recognizes Phosphorproteins in Interphase and Mitotic Cells", Experimental Cell Research, 195:145-153 (1991).
Towbin, et al., "Electrophoretic transfer of proteins from polyacrylamide gels to nitrocellulose sheets: Procedure and some applications", Proc. Natl. Acad. Sci USA., 76:4350-4354 (1979).
Vasquez, et al., "Specific mutations induced by triplex-forming oligonucleotides in mice", Science, 290:530-533 (2000).
Vasquez, et al., "Triplex-directed modification of genes and gene activity.", Trends Biochem. Sci., 23(1):4-9 (1998).
Wang, et al., "Altered Repair of Targeted Psoralen Photoadducts in the Context of an Oligonucleotide-mediated Triple Helix", J. Biol. Chem., 270(22):22595-22601(1996a).
Wansink, et al., "Fluorescent Labeling of Nascent RNA Reveals Transcription by RNA Polymerase II in Domains Scattered Throughout the Nucleus," J. Cell. Biol., 122:283-293 (1993).
Warren and Nelson, "Nonmitogenic Morphoregulatory Action of pp60.sup.v-src on Multicellular Epithelial Structures", Mol. Cell. Biol., 7:1326-1337 (1987).
Warren, et al., "Cytostellin: a novel. highly conserved protein that undergoes continuous redistribution during the cell cycle", J. Cell Sci., 103:381-388 (1992).
Whitesell, et al., "Stability, clearance, and disposition of intraventricularly administered oligodeoxynucleotides: implications for therapeutic application within the central nervous system," Proc. Natl. Acad. Sci. U S A., 90(10):4665-9 (1993).
Wood, et al., "The Effect of Volume and Temperature on the Energy and Entropy of Pure Liquids", J. Am. Chem. Soc., 79:2023-2024 (1957).
Xing and Lawrence, "Higher Level Organization of Individual Gene Transcription and RNA Splicing," Science 259:1326-1330 (1993).
Yang, et al., "Nu-MA: An Unusually Long Coiled-Coil Related Protein in the Mammalian Nucleus," J. Cell Biol. 116:1303-1317 (1992).
Zendegui, et al., "In vivo stability and kinetics of absorption and disposition of 3' phosphopropyl amine oligonucleotides.", Nucleic Acids Res., 20(2):307-314 (1992).
Zielke, et al., "Repetitive synchronization of human lymphoblast cultures with excess thymidine", Methods Cell Biol., 8(0):107-121 (1974).
Zon and Geiser, "Phosphorothioate oligonucleotides: chemistry, purification, analysis, scale-up and future directions," Anticancer Drug Des. 6(6):539-68 (1991).
Horne, et al., "Recognition of Mixed-Sequence Duplex DNA by Alternate-Strand Triple-Helix Formation", J. Am. Chem. Soc., 112:2435-2437 (1990).
Izvolsky, et al., "Sequence-specific protection of duplex DNA against restriction and methylation enzymes by pseudocomplementary PNAs", Biochemistry, 10908-10913 (2000).
Knauert, et al., "Triplex-stimulated intermolecular recombination at a single-copy genomic target", Mol. Therapy, 14:392-400 (2006).
Lohse, et al., "Double duplex invasion by peptide nucleic acid: a general principle for sequence-specific targeting of double-stranded DNA", Proc. Natl. Acad. Sci. USA, 96:11804-11808 (1999).
Lorenz, et al., "Steroid and lipid conjugates of siRNAs to enhance cellular uptake and gene silencing in liver cells", Bioorg. Med. Chem. Lett., 14(19):4975-4977 (2004).
Olsen, et al., "Genomic sequence correction by single-stranded DNA oligonucleotides: role of DNA synthesis and chemical modifications of the oligonucleotide ends", J. Gene Med., 7:1534-1544 (2005).
Urnov, et al., "Highly efficient endogenous human gene correction using designed zinc-finger nucleases", Nature, 435:646-651 (2005).
Vasquez, et al., "Manipulating the mammalian genome by homologous recombination", Proc. Natl. Acad. Sci. USA, 98:8403-8410 (2001).
Wu, et al., "Increased efficiency of oligonucleotide-mediated gene repair through slowing replication fork progression", Proc. Natl. Acad. Sci. USA, 102:2508-2513 (2005).
Rump, et al., "Modification of the plasma clearance and liver uptake of steroid ester-conjugated oligodeoxynucleotides by association with (lactosylated) low-density lipoprotein", Biochem. Pharmacol., 59(11):1407-1416 (2000).
Braden, et al., "Polymeric nanoparticles for sustained down-regulation of annexin A2 lead to reduction in proliferation and migration of prostate cancer cells", Journal of Biomedical Nanotechnology 3:148-159 (2007).
Bramwell, et al., "Particulate delivery systems for biodefense subunit vaccines", Adv. Drug Deliv. Rev., 57(9):1247-65 (2005).
Conner and Schmid, "Regulated portals of entry into the cell", Nature 422:37-44 (2003).
Desai, et al., "The mechanism of uptake of biodegradable microparticles in Caco-2 cells is size dependent", Pharm. Res., 14(11):1568-73 (1997).
Fahmy, et al., "Surface modification of biodegradable polyesters with fatty acid conjugates for improved drug targeting", Biomaterials, 26: 5727-5736 (2005).
Jiang, et al., "Biodegradable poly(lactic-co-glycolic acid) microparticles for injectable delivery of vaccine antigens", Adv. Drug Deliv. Rev., 57(3):391-410 (2005).
Khan, A. et al., "Sustained polymeric delivery of gene silencing antisense ODNs, siRNA, DNAzymes and ribozymes: in vitro and in vivo studies", J Drug Target, 12:393-404 (2004).
Adzick, "Fetal myelomeningocele: natural history, pathophysiology, and in-utero intervention", Seminars in fetal & neonatal medicine, 15(1):9-14 (2010).
Adzick, et al., "A randomized trial of prenatal versus postnatal repair of myelomeningocele", The New England Journal Of Medicine, 364(11):993-1004 (2011).
Akinc, et al., "Synthesis of poly(beta-amino ester)s optimized for highly effective gene delivery", Bioconjug Chem., 14:979-88 (2003).
Alton, et al., "Repeated nebulisation of non-viral CFTR gene therapy in patients with cystic fibrosis: a randomised, double-blind, placebo-controlled, phase 2b trial", Lancet Respir Med., 3(9):684-91 (2015).
Ryan, et al., "Knockout-transgenic mouse model of sickle cell disease." Science., 278(5339):873-6 (1997).
Sahu, et al., "Synthesis and characterization of conformationally preorganized, (R)-diethylene glycol-containing γ-peptide nucleic acids with superior hybridization properties and water solubility", J. Org. Chem., 76:5614-27 (2011).
Rodriguez, et al., "Minimal "Self" peptides that inhibit phagocytic clearance and enhance delivery of nanoparticles", Science, 339:971-5 (2013).
Gruenert, et al., "Established cell lines used in cystic fibrosis research", J Cystic Fibros, 3 (Suppl 2):191-6 (2004).
Genbank accession No. U01317.1—"Human beta globin region on chromosome 11",42 pages, first appeared Feb. 18, 1994, updated Jan. 9, 2012, accessed Aug. 9, 2017.
Fields, et al., "Modified poly(lactic-co-glycolic acid) nanoparticles for enhanced cellular uptake and gene editing in the lung", Adv Healthc Mater., 4(3):361-6 (with supporting information) (2015).
Wick, et al., "Barrier capacity of human placenta for nanosized materials", Enviro Health Perspectives, 118(3):432-6 (2010).
Zhou, et al., "Biodegradable poly(amine-co-ester) terpolymers for targeted gene delivery", Nat Mater., 11(1):82-90 (2012).

(56) References Cited

OTHER PUBLICATIONS

Tatokoro, et al., "Heat shock protein 90 targeting therapy: state of the art and future perspective", EXCLI J., 14:48-58 (2015).
Sugiyama and Kittaka, "Chiral peptide nucleic acids with a substituent in the N-(2-aminoethy)glycine backbone", Molecules, 18:287-310 (2013).
Weber and Ryan, "ATM and ATR as therapeutic targets in cancer", Pharmacol Ther., 149:124-38 (2015).
Zeiher, et al., "A mouse model for the delta F508 allele of cystic fibrosis", J Clin Invest., 96:2051-64 (1995).
Yuan, et al., "siRNA drug delivery by biodegradable polymeric nanoparticles", J. Nanosci. Nanotechnol., 6:2821-8 (2006).
Yin, "Genome editing with Cas9 in adult mice corrects a disease mutation and phenotype", Nat Biotechnol., 32(6):551-3 (2014).
Walkley, "Pathogenic cascades in lysosomal disease—Why so complex", J. Inherit. Metab. Dis., 32(2):181-9 (2009).
Smith, et al., "The ATM-Chk2 and ATR-Chk1 pathways in DNA damage signaling and cancer", Adv Cancer Res., 108:73-112 (2010).
Singer, et al., "Electronic barcoding of a viral gene at the single-molecule lever", Nano Ltrs., 12:1722-8 (2012).
Schleifman, et al., Targeted disruption of the CCR5 gene in human hematopoietic stem cells stimulated by peptide nucleic acids Chem Biol., 18:1189-98 (2011).
Sargent, et al., "Oligo/polynucleotide-based gene modification: strategies and therapeutic potential", Oligonucleotides, 21(2):55-75 (2011).
Yu, et al., "Novel aptamer-nanoparticle bioconjugates enhances delivery of anticancer drug to MUC1-positive cancer cells in vitro", PLoS One., 6:e24077 (2011).
Von Bismarck, et al., "IKK NBD peptide inhibits LPS induced pulmonary inflammation and alters sphingolipid metabolism in a murine model", Pulm Pharmacol Ther., 25(3):228-35 (2012).
Staretz-Chacham, et al., "Lysosomal storage disorders in the newborn", Pediatrics, 123(4):1191-207 (2009).
Sinn, et al., "Lentiviral vector gene transfer to porcine airways", Mol Ther Nucleic Acids, 1:e56 (2012).
Yamano, et al., "Modified Tat peptide with cationic lipids enhances gene transfection efficiency via temperature-dependent and caveolae-mediated endocytosis", J Control Release, 152:278-85 (2011).
Wang, et al., "The sustained-release behavior and in vitro and in vivo transfection of pEGFP-loaded core-shell-structured chitosan-based composite particles", Intl J Namomed., 9:4965-78 (2014).
UniProtKB—21581(SCF_RAT), 7 pages, first appeared May 1, 1991, updated May 10, 2017, accessed Aug. 11, 2017.
Vasquez, et al., "Human XPA and RPA DNA repair proteins participate in specific recognition of triplex-induced helical distortions", PNAS, 99:5848-53 (2002).
UniProtKB—P21583 (SCF_Human), 10 pages, first appeared May 1, 1991, updated May 10, 2017, accessed Aug. 11, 2017.
Woodrow, et al., "Intravaginal gene silencing using biodegradable polymer nanoparticles densely loaded with small-interfering RNA", Nat Mater, 8:526-33 (2009).
Rivera-Torres, et al., "The position of DNA cleavage by TALENs and cell synchronization influences the frequency of gene editing directed by single-stranded oligonucleotides", Plos One, 9(5):e96483 1-8 (2014).
Reay, et al., "Full-length dystrophin gene transfer to the mdx mouse in utero", Gene Therapy, 15:531-6 (2008).
Recombinant Rat SCF (Stem Cell Factor) Accession No. P2158,1 Catalog No. 300-32) accessed Aug. 11, 2017.
Rapireddy, et al., "Strand invasion of mixed-sequence, double-helical B-DNA by γ-peptide nucleic acids containing G-clamp nucleobases under physiological conditions", Biochemistry, 50(19):3913-8 (2011).
Ramachandran, et al., "A microRNA network regulates expression and biosynthesis of wild-type and DeltaF508 mutant cystic fibrosis transmembrane conductance regulator", PNAS, 109:13362-7 (2012).
Pászty, et al., "Transgenic knockout mice with exclusively human sickle hemoglobin and sickle cell disease." Science, 278(5339):876-8 (1997).

Oakland, et al., "Advances in cell and gene-based therapies for cystic fibrosis lung disease", Mol Ther., 20:1108-15 (2012).
Nielsen, et al., "Sequence-Selective Recognition of DNA by Strand Displacement with a Thymine-Substituted Polyamide", Science (Washington, D.C., 1883-), 254:1497-1500 (1991).
Nie, et al., "Lysine-based peptide-functionalized PLGA foams for controlled DNA delivery", J Control Release, 138:64-70 (2009).
NCBI Reference Sequence: NG_008103.1), "*Homo sapiens* iduronidase, alpha-L-(IDUA), RefSeqGene on chromosome 4", 14 pages, first appeared Nov. 27, 2008, updated Jul. 12, 2017, accessed Aug. 10, 2017.
NCBI Reference Sequence: NG_007119.1), "*Homo sapiens* galactosidase alpha (GLA), RefSeqGene (LRG_672) on chromosome X", 10 pages first appeared Nov. 27, 2007, updated Jul. 12, 2017, accessd Aug. 10, 2017.
Miller, et al., "A TALE nuclease architecture for efficient genome editing", Nature Biotechnol 29: 143 (2011).
Mcneer, "Nanoparticles for site specific genome editing", Dissertation presented to the Facility of Graduate School of Yale University, 154 pages, May 2013.
Miccio, et al., "In vivo selection of genetically modified erythroblastic progenitors leads to long-term correction of beta-thalassemia", PNAS, 105:10547-52 (2008).
Mcneer, et al., "Correction of F508DEL CFTR using nanoparticles delivering triplex-forming peptide nucleic acid molecules", Nat Commun. 6(6952):1-25 (2015c).
Mcneer, et al., "Polymer delivery systems for site-specific genome editing", J Control Release, 155(2): 312-316 (2011b).
Mcneer, et al., "Nanoparticles Deliver Triplex-forming PNAs for Site-specific Genomic Recombination in CD34+ Human Hematopoietic Progenitors", Mol Ther., 19(1):172-80 (2011a).
Magzoub, et al., "N-terminal peptides from unprocessed prion proteins enter cells by micropinocytosis", Biochem Biophys Res Commun., 348:379-85 (2006).
Mali, et al., "RNA-guided human genome engineering via Cas9", Science, 339:823-6 (2013).
Luo, et al., "Controlled DNA delivery systems", Pharm Res, 16:1300-08 (1999).
Lynn, et al., "Degradable Poly(β-amino esters): Synthesis, Characterization, and Self-Assembly with Plasmid DNA", J Am Chem Soc., 122(44):10761-10768 (2000).
Little, et al., "Poly-beta amino ester-containing microparticles enhance the activity of nonviral genetic vaccines", PNAS, 101:9534-9 (2004).
Little, et al., "Formulation and characterization of poly (beta amino ester) microparticles for genetic vaccine delivery", J Control Release, 107:449-62 (2005).
Luens, et al., "Thrombopoietin, kit ligand, and flk2/flt3 ligand together induce increased numbers of primitive hematopoietic progenitors from human CD34+Thy-1+Lin-cells with preserved ability to engraft SCID-hu bone", Blood 91:1206-15 (1998).
Lewis, et al., "A common human beta globin splicing mutation modeled in mice", Blood, 91:2152-6 (1998).
Konstan, et al., "Compacted DNA Nanoparticles Administered to the Nasal Mucosa of Cystic Fibrosis Subjects Are Safe and Demonstrate Partial to Complete Cystic Fibrosis Transmembrane Regulator Reconstitution", Human Gene Therapy, 15(12):1255-69 (2004).
Kim, et al. "Insertion and deletion mutants of FokI restriction endonuclease", J. Biol. Chem. 269:31978-82 (1994b).
Kim, et al., "Chimeric restriction endonuclease", PNAS, 91:883-7 (1994a).
Kim, et al., "USP17- and SCFβTrCP-Regulated Degradation of DEC1 Controls the DNA Damage Response", Mol Cell Biol., 34(22):4177-85 (2014).
Karen, et al., "Angiokeratoma corporis diffusum (Fabry disease)", Dermatol. Online J., 11(4): 8 (2005).
Kamei, et al., "Mechanistic study of the uptake/permeation of cell-penetrating peptides across a caco-2 monolayer and their stimulatory effect on epithelial insulin transport", J Pharm Sci., 102(11):3998-4008 (2013).
Jia, et al., "Bacterial delivery of TALEN proteins for human genome editing", PlosOne, 9(3):e91547 1-9 (2014).

(56) References Cited

OTHER PUBLICATIONS

Hubbell, et al., "Chemistry. Nanomaterials for drug delivery", Science, 337:303-5 (2012).
Hutt, et al., "Reduced histone deacetylase 7 activity restores function to misfolded CFTR in cystic fibrosis", Nat Chem Biol., 6:25-33 (2010).
Hu, et al., "ELDA: extreme limiting dilution analysis for comparing depleted and enriched populations in stem cell and other assays", J Immunol Methods, 347:70-8 (2009).
Huang, et al., "Preparation and determination of optical purity of y-lysine modified peptide nucleic acid analogues", Arch Pharm Res, 35(3):517-522 (2012).
Hrkach, et al., "Preclinical Development and Clinical Translation of a PSMA-Targeted Docetaxel Nanoparticle with a Differentiated Pharmacological Profile", Sci Transl Med., 4:128ra139 (2012).
Hanna, et al., "Treatment of Sickle Cell Anemia Mouse Model with iPS Cells Generated from Autologous Skin", Science, 318:1920-3 (2007).
Holt, et al., "Human hematopoietic stem/progenitor cells modified by zinc-finger nucleases targeted to CCR5 control HIV-1 in vivo", Nature biotechnology, 28(8):839-47 (2010).
Haendel, et al., "Zinc-finger nuclease based genome surgery: it's all about specificity", Gene Ther., 11:28-37 (2011).
Griesenbach, et al., "Gene transfer to the lung: Lessons learned from more than 2 decades of CF gene therapy", Advanced Drug Delivery Reviews, 61:128-139 (2009).
Green, "A combinatorial polymer library approach yields insight into nonviral gene delivery", Acc Chem Res., 41(6):749-59 (2008).
Grafmueller, et al., "Bidirectional transfer study of polystyrene nanoparticles across the placental barrier in an ex vivo human placental perfusion model", Enviro Health Perspectives, 123(12):1280-6 (2015).
Granio, et al., "Adenovirus 5-fiber 35 chimeric vector mediates efficient apical correction of the cystic fibrosis transmembrane conductance regulator defect in cystic fibrosis primary airway epithelia", Human Gene Therapy, 21:251-69 (2010).
Goncz, et al., "Targeted replacement of normal and mutant CFTR sequences in human airway epithelial cells using DNA fragments", Hum Mol Genet., 7:1913-9 (1998).
Goncz, et al., "Expression of DeltaF508 CFTR in normal mouse lung after site-specific modification of CFTR sequences by SFHR", Gene Ther., 8:961-965 (2001).
Genbank accession No. AH006034.1, "Human cystic fibrosis transmembrane conductance regulator (CFTR) gene", 24 pages, first appeared Jul. 26, 1993, updated Jun. 10, 2016, accessed Aug. 9, 2017.
Fields, et al., "Surface modified poly(β amino ester)-containing nanoparticles for plasmid DNA delivery", J Control Release, 164(1):41-8 (2012).
Felfly, et al., "Long-term correction of beta-thalassemia with minimal cellular requirement and transplantation modalities", Mol Ther, 15:1701-9 (2007).
Faruqi, et al., "Peptide nucleic acid-targeted mutagenesis of a chromosomal gene in mouse cells", PNAS, 95:1398-1403 (1998).
Egholm, et al., "PNA hybridizes to complementary oligonucleotides obeying the Watson-Crick hydrogen-bonding rules", Nature, 365:566-8 (1993).
Endoh, et al., "Cellular siRNA delivery using cell-penetrating peptides modified for endosomal escape", Adv Drug Deliv Rev., 61:704-9 (2009).
Egan, et al., "Calcium-pump inhibitors induce functional surface expression of Delta F508-CFTR protein in cystic fibrosis epithelial cells", Nat Med., 8:485-92 (2002).
Dib and Pastories, "Laronidase for treating mucopolysaccharidosis type I", Genet. Mol. Res., 6(3):667-74 (2007).
Doudna, et al., "Genome editing. The new frontier of genome engineering with CRISPR-Cas9", Science, 346:1258096 (2014).
Cu, et al., "Ligand-modified gene carriers increased uptake in target cells but reduced DNA release and transfection efficiency", Nanomedicine, 6:334-343 (2010).
Davis, et al., "Cystic fibrosis since 1938", Am J Respir Crit Care Med., 173(5):475-82 (2006).
Davis, et al., "Cystic fibrosis", Pediatr Rev., 22(8):257-64 (2001).
Cradick, et al., "CRISPR/Cas9 systems targeting β-globin and CCR5 genes have substantial off-target activity", Nucleic Acids Res., 41:9584-92 (2013).
Cruz, et al., "Targeted PLGA nano—but not microparticles specifically deliver antigen to human dendritic cells via DC-SIGN in vitro", J Control Release, 144:118-126 (2010).
Choi, et al., "Application of chitosan and chitosan derivatives as biomaterials", J Ind Eng Chem., 33:1-10 (2016).
Cong, et al., "Multiplex genome engineering using CRISPR/Cas systems", Science, 15:339(6121):819-23 (2013).
Chin, et al., "Triplex-forming Peptide Nucleic Acids Induce Heritable Elevations in Gamma-globin Expression in Hematopoietic Progenitor Cells", Mol. Ther., 21(3):580-7 (2013).
Chin, et al., "Repair of DNA lesions associated with triplex-forming oligonucleotides", Mol Carcinog., 48:389-399 (2009).
Cermak, et al., "Efficient design and assembly of custom TALEN and other TAL effector-based constructs for DNA targeting", Nucl. Acids Res., 39(12):e82 (2011).
Cheng, et al., "Enhanced siRNA delivery into cells by exploiting the synergy between targeting ligands and cell-penetrating peptides", Biomaterials, 32(26):6194-203 (2011).
Cartier, et al., "Hematopoietic stem cell gene therapy with a lentiviral vector in X-linked adrenoleukodystrophy", Science, 326(5954):818-23 (2009).
Cartiera, et al., "Partial correction of cystic fibrosis defects with PLGA nanoparticles encapsulating curcumin", Mol Pharm, 7:86-93 (2010).
Cai, et al., "In utero delivery of oligodeoxynucleotides for gene correction", Gene Correction Methods and Protocols, Methods in Molecular Biology vol. 1114, Chapter 26:399-411, Francesca Storici, editor Springer Science-Business Media (2014).
Bruscia, et al., "Isolation of CF cell lines corrected at DeltaF508-CFTR locus by SFHR-mediated targeting", Gene Ther., 9:683-5 (2002).
Beumer, et al., "Efficient gene targeting in *Drosophila* with zinc-finger nucleases", Genetics, 172:2391-2403 (2006).
Bertram, "Functionalized poly(lactic-co-glycolic acid) enhances drug delivery and provides chemical moieties for surface engineering while preserving biocompatibility", Acta Biomater. 5:2860-71 (2009).
Barkalina, et al., "Nanotechnology in reproductive medicine: emerging applications of nanomaterials", Nanomedicine, 10:921-38 (2014).
Bahal, et al., "Sequence-Unrestricted, Watson-Crick Recognition of Double Helical B-DNA by (R)-MiniPEG-gPNAs", ChemBioChem, 13:56-60 (2012).
Bahal, et al., "Site-specific genome editing of hematopoietic stem cells for beta thalassemia gene therapy", Mol Ther., 22:S290-91 (2014b).
Arnould, et al., "The I-CreI meganuclease and its engineered derivatives: applications from cell modification to gene therapy", Protein Eng. Des. Sel., 24(1-2):27-31 (2011).
Babar, et al., "Nanoparticle-based therapy in an in vivo microRNA-155 (miR-155)-dependent mouse model of lymphoma", PNAS, 109:E1695-E1704 (2012).
Armstrong, et al., "Gene therapy in cystic fibrosis", Arch Dis Child., 99(5):465-8 (2014).
Andreani, et al., "Persistence of mixed chimerism in class 3 thalassemic patients following BMT", Bone Marrow Transplant, 7(Suppl 2):75 (1991).
Alton, et al., "A randomised, double-blind, placebo-controlled phase IIB clinical trial of repeated application of gene therapy in patients with cystic fibrosis", Thorax, 68(11):1075-7 (2013).
Thompson and Eastman, "The cancer therapeutic potential of Chk1 inhibitors: how mechanistic studies impact on clinical trial design", Br J Clin Pharmacol., 76(3):358-69 (2013).
Schleifman, et al., "Site-specific Genome Editing in PBMCs With PLGA Nanoparticle-delivered PNAs Confers HIV-1 Resistance in Humanized Mice", Mol. Ther Nucleic Acids, 2:e135 (2013).

(56) References Cited

OTHER PUBLICATIONS

Shenoy, et al., "Calcium-modulated chloride pathways contribute to chloride flux in murine cystic fibrosis-affected macrophages", Pediatr Res., 70:447-52 (2011).
Agata, et al., "Expression of the PD-1 antigen on the surface of stimulated mouse T and B lymphocytes", Int. Immunol., 8:765-772 (1996).
Aguado, et al., "Controlled-release vaccines—biodegradable polylactide/polyglycolide (PL/PG) microspheres as antigen vehicles," Immunobiology, 184(2-3):113-25 (1992).
Sazani, et al., "Systemically delivered antisense oligomers upregulate gene expression in mouse tissues", Nat. Biotechnol., 20:1228-33 (2002).
Schwank, et al., "Functional repair of CFTR by CRISPR/Cas9 in intestinal stem cell organoids of cystic fibrosis patients", Cell Stem Cell, 13:653-8 (2013).
Soutschek, et al., "Therapeutic silencing of an endogenous gene by systemic administration of modified siRNAs", Nature, 432(7014):173-8 (2004).
UniProtKB—P20826 (SCF_Mouse), 8 pages, first appeared Feb. 1, 1991, updated May 10, 2017, accessed Aug. 11, 2017.
Bentin, et al., "Structural diversity of target-specific homopyrimidine peptide nucleic acid-dsDNA complexes", Nucleic Acids Res, 34(20): 5790-5799 (2006).
Depreaux, et al., "Antisense oligonucleotides delivered to the amniotic cavity in utero modulate gene expression in the postnatal mouse," Nucleic Acids Res. 44(20):9519-9529 (2016).
Hansen, et al., "High-affinity triplex targeting of double stranded DNA using chemically modified peptide nucleic acid oligomers", Nucleic Acids Research, 37(13): doi: 10.1093/nar/gkp437 (2009).
Jain, et al., "Influence of pendant chiral C(γ)-(alkylideneamino/guanidino) cationic side-chains of PNA backbone on hybridization with complementary DNA/RNA and cell permeability", J. Org. Chem., 79(20): 9567-9577 (2014).
Juch, et al., "Nanomaterial interference with early human placenta: Sophisticated matter meets sophisticated tissues", Reproductive Toxicology, 41:73-79 (2013).
Kayali, et al., "Site-directed gene repair of the dystrophin gene mediated by PNA-ssODNs", Human Molecular Genetics, 19(16): 3266-3281 (2010).
Kenesei, et al., "Enhanced detection with spectral imaging fluorescence microscopy reveals tissue- and cell-type-specific compartmentalization of surface-modified polystyrene nanoparticles," J.Nanobiotechnol, 14:55 (2016).
Mcclain, et al., "In utero stem cell transplantation and gene therapy: Recent progress and the potential for clinical application," Best Practice & Research Clinical Obstetrics and Gynaecology, 31:88-98 (2016).
Bramlage, et al., "Designing ribozymes for the inhibition of gene expression," Trends Biotechnol. 16, 434 (1998).
Bindra et al., "Hypoxia-induced down-regulation of BRCA1 expression by E2Fs", Cancer Res, 65(24):11597-604, (2005).
Agrawal, et al., "Pharmacokinetics, biodistribution, and stability of oligoeoxynucleotide phosphorothioates in mice," Proc Natl Acad Sci U S A. 88(17):7595-9 (1991).
Asensio, et al. "Thermodynamic, kinetic, and conformational properties of a parallel intermolecular DNA triplex containing 5' and 3' junctions", Biochemistry, 37(43):15188-98 (1998a).
Barre, et al., "Unambiguous demonstration of triple-helix-directed gene modification," Proc. Natl. Acad. Sci. USA 97, 3084 (2000).
Beal & Dervan, "The Influence of Single Base Triplet Changes on the Stability of a Pur.Pur.Pyr Triple Helix Determined by Affinity Cleaving," Nucleic Acids Res. 20(11): 2773-2776 (1992).
Beal & Dervan , "Second Structural Motif for Recognition of DNA by Oligonucleotide-Directed Triple-Helix Formation," Science 251:1360-1363 (1991).
Bindra & Glazer, "Co-repression of mismatch repair gene expression by hypoxia in cancer cells: role of the Myc/Max network", Cancer Lett, 252(1):93-103 (2007).

Blume, et al., "Triple helix formation by purine-rich oligonucleotides targeted to the human dihydrofolate reductase promoter", Nucleic Acids Res., 20(7):1777-84 (1992).
Bregman et al., "Cytostellin distributes to nuclear regions enriched with splicing factors," J Cell Sci. 107 (Pt 3):387-96 (1994).
Campbell, et al., "Homologous recombination involving small single-stranded oligonucleotides in human cells," New Biol. 1(2):223-7 (1989).
Chan, et al., "Triplex DNA: Fundamentals, Advances, and Potential Applications for Gene Therapy," J. Mol. Med. 75: 267-282 (1997).
Cole-Strauss, et al., "Correction of the mutation responsible for sickle cell anemia by an RNA-DNA oligonucleotide.", Science, 273(5280): 1386-1389 (1996).
Connell, et al., "Automated DNA sequence analysis." Bio Techniques 5:342 (1987).
Cooney, et al., "Site-Specific Oligonucleotide Binding Represses Transcription of the Human c-myc Gene in Vitro," Science 241:456 (1988).
Culver et al., "Correction of chromosomal point mutations in human cells with bifunctional oligonucleotides", Nature Biotechnology, 17(10):989-993 (1999).
Di Domenico, et al., "Gene Therapy for a Mucopolysaccharidosis Type I Murine Model with Lentiviral-IDUA Vector", Human Gene Therapy, 16(1):81-90 (2005).
Duval-Valentin, et al., "Specific Inhibition of Transcription by Triple Helix-Forming Oligonucleotides," Proc. Natl. Acad. Sci. USA 89:504 (1992).
Fakan & Nobis, "Ultrastructural Localization of Transcription Sites and of RNA Distribution During the Cell Cycle of Synchronized Cho Cells," Exp. Cell Res. 113:327-337 (1978).
Famulok, "Oligonucleotide aptamers that recognize small molecules," Curr. Opin. Struct. Biol. 9, 324 (1999).
Faruqi, et al., "Recombination induced by triple helix-targeted DNA damage in mammalian cells", Mol. Cell. Biol. 16: 6820-6828, (1996).
Francois et al., "Sequence-Specific Recognition and Cleavage of Duplex DNA via Triple-Helix Formation by Oligonucleotides Covalently Linked to a Phenanthroline-Copper Chelate," Proc. Natl. Acad. Sci. USA 86:9702 (1989).
Galderisi, et al., "Antisense oligonucleotides as therapeutic agents," J. Cell Physiol. 181, 251 (1999).
Giovannangeli, et al., "Oligodeoxynucleotide-directed photoinduced cross-linking of HIV proviral DNA via triple-ihelix formation," Nucleic Acids Res. 20:4275-4281 (1992a).
Giovannangeli, et al., "Triple-helix formation by oligonucleotides containing the three bases thymine, cytosine, and guanine," Proc. Natl. Acad. Sci. USA 89:8631-8635 (1992B).
Glazer, et al., "DNA mismatch repair detected in human cell extracts," Mol. Cell. Biol. 7:218 (1987).
Good, et al., "Progress in developing PNA as a gene-targeted drug," Antisense Nucleic Acid Drug Dev. 7(4):431-7 (1997).
Gorman and Glazer, "Directed gene modification via triple helix formation," Curr. Mol. Med., 1(3): 391-399 (2001).
Gottesfeld, et al., "Regulation of gene expression by small molecules" Nature 387(6629):202-5 (1997).
Grigoriev, et al., "A Triple-Helix-Forming Oligonucleotide-Intercalator Conjugate Acts as a Transcriptional Repressor via Inhibition of NF kB Binding to Interleukin-2 Receptor _ Regulatory Sequence," J. of Biological Chem. 267:3389 (1992B).
Grigoriev, et al., "Inhibition of Gene Expression by Triple Helix-directed DNA Cross-linking at Specific Sites," Proceedings of the National Academy of Sciences of USA, 90(8):3501-3505 (1993).
Gura, "Antisense has growing pains," Science 270:575-77 (1995).
Hanawalt, "Transcription-coupled repair and human diseases," Science 266(5193): 1957-1958 (1994).
Hu, et al., "Reaction parameters pf targeted gene repair in mammalian cells", Mol. Biotech., 29:197-210 (2005).
Huang & Spector, "Nascent pre-mRNA transcripts are associated with nuclear regions enriched in splicing factors," Genes and Dev. 5:2288 (1991).
Igoucheva, et al., "Transcription affects formation and processing of intermediates in oligonucleotide-mediated gene alteration", Nucleic Acid Res., 31:2659-2670 (2003).

(56) References Cited

OTHER PUBLICATIONS

Ito, et al., "Sequence-specific DNA purification by triplex affinity capture," Proc. Natl. Acad. Sci. USA 89:495 (1992).
Jasin "Genetic manipulation of genomes with rare-cutting endonucleasis", Trends Genet., 12:224-228 (1996).
Jones & Wood, "Preferential binding of the xeroderma pigmentosum group A complementing protein to damaged DNA," Biochemistry 32(45):12096-104 (1993).
Kim, et al., "Inhibition of Transcription of the Human c-myc Protooncogene by Intermolecular Triplex," Biochemistry 37: 2299-304 (1998).
Kim, et al., "Site-directed gene mutation at mixed sequence targets by psoralen-conjugated pseudo-complementary peptide nucleic acids", Nucleic Acids, 35:7604-7613 (2007b).
Knauert, et al., "Distance and affinity dependence of triplex-induced recombination." Biochemistry, 44:3856-3864 (2005).
Kong, "Btrim: a fast, lightweight adapter and quality trimming program for next-generation sequencing technologies," Genomics, 98:152-153 (2011).
Konopka & Duzgunes, "Expression of CD4 controls the susceptibility of THP-1 cells to infection by R5 and X4 HIV type 1 isolates", AIDS Res Hum Retroviruses, 18(2):123-31 (2002).
Kramer, et al., "Monoclonal Antibody Directed Against RNA Polymerase II of *Drosophila melanogaster*," Molec. Gen. Genet. 180:193-199 (1980).
Lahoud, et al., "Properties of pseudo-complementary DNA substituted with weakly pairing analogs of guanine or cytosine", Nucleic Acid Research, 36(22):6999-7008 (2008).
Lin et al., "Stability of DNA triplexes on shuttle vector plasmids in the replication pool in Mammalian cells", J. Biol. Chem., 275(50):39117-39124 (2000).
Lin, et al., "Use of EDTA derivatization to characterize interactions between oligodeoxyribonucleoside methylphosphonates and nucleic acids," Biochemistry 28:1054 (1989).
Maher, et al., "Analysis of Promoter-Specific Repression by Triple Helical DNA Complexes in a Eukaryotic Cell-Free Transcription System," Biochemistry 31:70 (1992).
Maher, et al., "Inhibition of DNA binding proteins by oligonucleotide-directed triple helix formation," Science 245:725 (1989).
Majumdar, et al., "Gene targeting by triple helix-forming oligonucleotides", Ann. N.Y. Acad. Sci., 1002:141-53 (2003B).
Mayer, "Synthesis and triplex forming properties of pyrrolidino pseudoisoccytidine containing oligodeoxynucleotides.", Org. Biomol. Chem., 3(9):1653-1658 (2005).
Beesley, et al., "Mutational analysis of 85 mucopolysaccharidosis type I families: frequency of known mutations, identification of 17 novel mutations and in vitro expression of missense mutations", Human Genetics, 109(5):503-511 (2001).
Moser & Dervan, "Sequence-specific cleavage of double helical DNA by triple helix formation," Science 238:645-650 (1987).
Parris, et al., "Proximal and distal effects of sequence context on ultraviolet mutational hotspots in a shuttle vector replicated in xeroderma cells," J mol Biol. 236(2):491-502 (1994).
Pei et al, "Site Specific Cleavage of Duplex DNA by a Semisynthetic Nuclease via Triple-Helix Formation," Proc. Natl. Acad. Sci. USA 87:9858 (1990).
Perrouault, et al., "Sequence-specific artificial photo-induced ndonucleases based on triple helix-forming oligonucleotides," Nature 344:358 (1990).
Pierce et al., "Oligonucleotide-directed single-base DNA alterations in mouse embryonic stem cells", Gene Therapy, 10(1):24-33 (2003).
Povsic, et al., "Sequence-Specific Alkylation of Double Helical DNA by Oligonucleotide Directed Triple-Helix Formation," J. Am. Chem. Soc. 112:9428 (1992).
Prakash, et al., "2'-O-[2-(guanidinium)ethyl]-modified oligonucleotides: stabilizing effect on duplex and triplex structures", Org. Lett., 6(12):1971-4 (2004).

Praseuth, et al., "Sequence-Specific Binding and Photocrosslinking of _ and _ Oligodeoxynucleotides to the Major Groove of DNA via Triple-Helix Formation," Proc. Natl. Acad. Sci. USA 85:1349 (1988).
Reardon, et al., "Removal of psoralen monoadducts and crosslinks by human cell free extracts," Nucleic Acids Res. 19: 4623 (1991).
Schneider, et al., "Optimal design of parallel triplex forming oligonucleotides containing Twisted Intercalating Nucleic Acids—TINA," Nucl. Acids Res. 38(13):4394-4403, (2010).
Seidman, et al., "The potential for gene repair via triple helix formation", The Clinical Journal of Investigation 112(4):487-94 (2003).
Semerad & Maher, "Exclusion of RNA Strands from a Purine Motif Triple Helix," Nucleic Acids Res. 22: 5321-5325 (1994).
Shen et al., "Intrinsic human immunodeficiency virus type 1 resistance of hematopoietic stem cells despite coreceptor expression", J Virol, 73:728 (1999).
Shimizu, et al., "Oligo(2'-O-methyl)ribonucleotides. Effective probes for duplex DNA", FEBS Lett., 302(2):155-8 (1992).
Shivji, et al., "Proliferating cell nuclear antigen is required for DNA excision repair," Cell 69: 367 (1992).
Spector, "Higher order nuclear organization: Three-dimensional distribution of small nuclear ribonucleoprotein particles," Proc. Natl. Acad. Sci. 87:147-151 (1990).
Streisinger, et al., "Frameshift mutations and the genetic code," Cold Spring harbor Symp. Quant. Biol. 31:77-84 (1966).
Summerton, et al., "Morpholino antisense oligomers: design, preparation, and properties", Antisense Nucleic Acid Drug Dev., 7(3):187-95 (1997).
Sung, et al., "Recombination factors of *Saccharomyces cerevisiae*," Mutat Res 451:257-75 (2000).
Thacker, "A surfeit of RAD51-like genes?," Trends Genet 15(5):166-8 (1999a).
Treisman, et al., "A single-base change at a splice site in a beta 0-thalassemic gene causes abnormal RNA splicing." Cell, 29(3): 903-911, (1982).
Uhlman, et al., "Antisense Oligonucleotides: A New Therapeutic Principle," Chem. Reviews 90(4):544-584 (1990).
Vasquez, et al., "Chromosomal mutations induced by triplex-forming oligonucleotides in mammalian cells," Nucleic Acids Res. 27: 1176 (1999).
Wang, et al., "Targeted Mutagenesis in Mammalian Cells Mediated by Intracellular Triple Helix Formation," Molecular and Cellular Biology, 15(32), 1759-1768 (1995).
Wood, et al., "Complementation of the xeroderma pigmentosum DNA repair defect in cell-free extracts," Cell 53:97 (1988).
Yang, et al., "Blocking the CC Chemokine Receptor 5 Pathway by Antisense Peptide Nucleic Acid Prolongs Islet Allograft Survivals", Transplantation Proceedings, 39(1):185-190 (2007).
Young et al., "Triple Helix Formation Inhibits Transcription Elongation in vitro," Proc. Natl. Acad. Sci. USA 88:10023 (1991).
White, et al., "Cell killing by the *Drosophila* gene reaper," Science 271(5250): 805-807 (1996).
Reza et al., "Triplex-mediated genome targeting and editing," Methods Mol Biol, 1114:115-142 (2014).
Svasti, et al., "RNA repair restores hemoglobin expression in IVS2-654 thalassemic mice", PNAS, 106:1205-10 (2009).
Strouse, et al., "Combinatorial gene editing in mammalian cells using ssODNs and TALENs", Scientific Reports, 4:3791-9 (2014).
Scott, et al., "Molecular genetics of mucopolysaccharidosis type I: diagnostic, clinical, and biological implications", Hum. Mutat. 6:288-302 (1995).
Aiuti, et al., "Gene therapy for immunodeficiency due to adenosine deaminase deficiency", N Engl J Med., 360(5):447-458 (2009).
Anandalingam, et al., "Nanoparticles with triplex-forming oligonucleotides for site specific editing of the human CFTR gene", Poster, Dept of Bioeng, Yale Univ School of Med. and School of Eng and Applied Sci., (2012).
Beer, et al., "Genome-edited human stem cell-derived beta cells: a powerful tool for drilling down om type 2 diabetes GWAS biology {version1: referees:2 approve]", https://f1000research.com/articles/5-1711/v1 (2016).

(56) References Cited

OTHER PUBLICATIONS

Chin, et al., "Correction of a splice-site mutation in the beta-globin gene stimulated by triplex-forming peptide nucleic acids", PNAS., 105(36):13514-19 (2008).
Cu, et al., "In vivo distribution of surface-modified PLGA nanoparticles following intravaginal delivery", J Control Release, 156:258-264 (2011).
Durland, et al., "Binding of triple helix forming oligonucleotides to sites in gene promoters", Biochemistry, 30(38):9246-9255 (1991).
Egan, et al., "Evidence against the rescue of defective DeltaF508-CFTR cellular processing by curcumin in cell culture and mouse models", Science, 304:600-2 (2004b).
Gabbianelli, et al., "Role of stem cell factor in the reactivation of human fetal hermoglobin", Mediter J Hemo Infect Dis., 1(1):e2009009 (2009).
Genbank accession No. NM_000579, "CCR5 chemokine (C-C motif) receptor 5 (*Homo sapiens*)", 8 pages, first appeared Mar. 24, 1999, updated Aug. 22, 2010, accessed Aug. 9, 2017.
Mcneer, et al., "Nanoparticles for site-specific genome editing in cystic fibrosis", 16 pages, presented at 26th Annual North American Cystic Fibrosis Conference, Orlando, FL, Oct. 11-13, (2012b).
Lee, et al., "Correction of the ΔF508 Mutation in the Cystic Fibrosis Transmembrane Conductance Regulator Gene by Zinc-Finger Nuclease Homology-Directed Repair", BioResearch Open Access, 1:99-108 (2012).
Li, et al., "Functional domains in Fok I restriction endonuclease", PNAS, 89:4275-9 (1992).
Martz, "Triplex solution for a monogenic problem", Science-Business exchange, 1(33); doi:10.1038/scibx.2008.794, Published online Sep. 18, 2008 (http://www.nature.com/scibx/journal/v1/n33/full/scibx.2008.794.html), 4 pages (2008).
NCBI Reference Sequence: NG_009783.1 "*Homo sapiens* glucosylceramidase beta (GBA), RefSeqGene on chromosome 1)", 11 pages, first appeared Feb. 19, 2009, updated Jul. 12, 2017, accessed Aug. 10, 2017.
Kim, et al., "Efficient sequence-directed psoralen targeting using pseudocomplementary peptide nucleic acids", Bioconjug. Chem., 18:567-572 (2007a).
Gaj, et al., "ZFN, TALEN, and CRISPER/cas-based methods for genome engineering", Trends in Biotech., 31(7):397-405 (2013).
Kukreti, et al., "Extension of the range of DNA sequences available for triple helix formation: stabilization of mismatched triplexes by acridine-containing oligonucleotides," (Nucl. Acid. Resc 25(21): 4264-4270, (1997).
Nansen, et al., "The role of CC chemokine receptor 5 in antiviral immunity", Blood, 99(4):1237-1245 (2002).
Oliveria, et al., "Enhancement of chitosan-mediated gene delivery through combination with phiC31 integrase", Acta Biomaterialia, 17:89-97 (2015).
Preprotech, Recombinant Human SCF Catalog No. 250-03, Stem Cell Factor, c-Kit Ligand, Mast Cell Growth Factor (MGF), Steel Factor, 2 pages, accessed Aug. 11, 2017.
Puri, et al., "Targeted gene knockout by 2'-O-aminoethyl modified triplex forming oligonucleotides", J.Biol. Chem., 276(31):28991-28998 (2001).
Sangamo Bioscience, Triple forming peptide nucleic acids (TFPs)-SGMO, http://www.investorvillage.com/mbthread.asp?mb=1933&=13823114&showall, post dated May 13, 2014, accessed Jul. 13, 2016.
Schleifman, et al., "Triplex-mediated gene modification", Methods in Molecular Biology, 175-190 (2008).
Seksek, et al., "Nuclear pH gradient in mammalian cells revealed by laser microspectrofluorimetry", Journal of Cell Science 109(1):257-262 (1996).
Shahid, et al., "Targeted cross-linking of the human beta-globin gene in living cells mediated by a triple helix forming oligonucleotide", Biochemistry, 45 (6): 1970-1978 (2006).
Strobel, et al., "Site-specific cleavage of human chromosome 4 mediated by triple-helix formation", Science, 254(5038):1639-42 (1991.

Thacker, "The photoprotective effect of ascorbic acid, acetylsalicylic acid, and indomethacin evaluated by the photo hen's egg test," Trends Genet 15(5): 166-8 (1999).
Wang, et al., "Mutagenesis in mammalian cells induced by triple helix formation and transcription-coupled repair," Science 271(5250): 802-805 (1996B).
Jinek, et al., "A programmable dual-RNA-guided DNA endonuclease in adaptive bacterial immunity", Science, 337(6096):816-21 (2012).
Li, et al., "Alteration of the cleavage distance of Fok I restriction endonuclease by insertion mutagenesis", PNAS, 90:2764-2768 (1993).
Alshamsan, "Nanoprecipitation is more efficient than emulsion solvent evaporation method to encapsulate cucurbitacin I in PLGA nanoparticles", Saudi Pharma J, 22(3):219-22 (2014).
Papaioannou, et al., "Oligonucleotide-directed gene-editing technology: mechanisms and future prospects", Expert Opin. Biol. Ther., 12(3):329-342 (2012).
Daksis, et al., "Heteropolymeric Triplex-Based Genomic Assay to Detect Pathogens or Single-Nucleotide Polymorphisms in Human Genomic Samples", PLOS ONE, 2:3 (2007).
Gamble, et al., "Development of Cu+2-Based Distance Methods and force Field Parameters for the Determination of PNA Conformations and Dynamics by EPR and MD Simulations", Journal of Physical Chemistry Part B, 124(35):7544-7556 (2020).
Deng, et al., "Improved i.p. drug delivery with bioadhesive nanoparticles", Proc. Natl. Acad. Sci., 113:11453-11458 (2016).
Avitabile, et al., "[gamma] sulphate ONA (PNA S): Highly Selective DNA Binding Molecule Showing Promising Antigene Activity", PLOS ONE, 7(5): e35774 (2012).
Kirillova, et al., "Polyanionic Carboxyethyl Peptide Nucleic Acids (ce-PNAs): Synthesis and DNA Binding", PLOS ONE, 10(10):e0140468 (2015).
Cantin, et al., "Synthesis of the monomeric building blocks of Z-olefinic PNA (Z-OPA) containing the bases adenine and thymine", Tetrahedron Lett., 38:4211-4214 (1997).
Cavazzana-Calvo, et al., "Gene therapy of human severe combined immunodeficiency (SCID)-X1 disease", Science, 288:669-672 (2000).
Chapman, et al., "Playing the end game: DNA double-strand break repair pathway choice," Mol. Cell, 47:497-510 (2012).
Chenna, et al., "A simple cytosine to G-clamp nucleobase substitution enables chiral gamma-PNAs to invade mixed-sequence double-helical B-form DNA", Chembiochem., 9:2388-2391 (2008).
Chung, et al., "Generation of ΔF508-CFTR T84 cell lines by CRISPR/Cas9-mediated genome editing", Biotechnol. Lett., 38:2023-2034 (2016).
Ciapetti, et al., "Synthesis of N-Fmoc-α-amino acids carrying the four DNA nucleobases in the side chain", Tetrahedron, 53:1167-1176 (1997).
Ciccia, et al., "The DNA damage response: making it safe to the play with knives," Mol. Cell., 40:179-204 (2010).
Coskun, et al., "Development of the fetal bone marrow niche and regulation of HSC quiescence and homing ability by emerging osteolineage cells", Cell Rep., 9:581-590 (2014).
Crane, et al., "Targeted Correction and Restored Function of the CFTR Gene in Cystic Fibrosis Induced Pluripotent Stem Cells", Stem Cell Reports, 4:569-577 (2015).
Cui, et al., "Ex vivo pretreatment of human vessels with siRNA nanoparticles provides protein silencing in endothelial cells", Nature Communications, 8:(191):1-11 (2017).
Diederichsen, et al., "Self-pairing PNA with alternating alanyl/homoalanyl backbone", Tetrahedron Lett., 37:475-478 (1996).
Diederichsen, et al., "Alanyl-PNA homoduplex: A-T pairing with the N7-regioisomer of adenine", Bioorg. Med. Chem. Lett., 8:165-168 (1998).
Doe, et al., "Generating CRISPR/Cas9-Derived Mutant Mice by Zygote Cytoplasmic Injection Using an Automatic Microinjector", Methods and Protocols, 1(5):1-12 (2018).
Dragulescu-Andrasi, et al., "A Simple γ-Backbone Modification Preorganizes Peptide Nucleic Acid into a Helical Structure", Journal of the American Chemical Society, 128(31):10258-67 (2006).
Efimov, et al., "Hydroxyproline-based DNA mimics provide an efficient gene silencing in vitro and in vivo", Nucleic Acids Res., 34(8):2247-2257 (2006).

(56) References Cited

OTHER PUBLICATIONS

Egan, et al., "Curcumin, a Major Constituent of Turmeric, Corrects Cystic Fibrosis Defects", Science, 304:600-602 (2004a).
Eriksson, et al., "PNA-nucleic acid complexes. Structure, stability and dynamics", Quart. Rev. Biophys., 29(4):369-394 (1996).
Ezzati, et al., "Tubal transport of gametes and embryos: a review of physiology and pathophysiology", J. Assist. Reprod. Genet., 31(10):1337-47 (2014).
Fanen, et al., "Genetics of cystic fibrosis: CFTR mutation classifications toward genotype-based CF therapies", Int. J. Biochem. Cell Biol., 52:94-102 (2014).
Firth, et al., "Functional Gene Correction for Cystic Fibrosis in Lung Epithelial Cells Generated From Patient iPSCs", Cell Rep., 12:1385-1390 (2015).
Fujii, et al., "Nucleic acid analog peptide (NAAP) 2. Syntheses and properties of novel DNA analog peptides containing nucleobase linked β-aminoalanine" Bioorg. Med. Chem. Lett. 7:637-627 (1997).
Gaspar, et al., "Gene therapy of X-linked severe combined immunodeficiency by use of a pseudotyped gammaretroviral vector", Lancet, 364:2181-2187 (2004).
Govindaraju, et al., "(1S,2R/1R,2S)-cis-Cyclopentyl PNAs (cpPNAs) as Constrained PNA Analogues: Synthesis and Evaluation of aeg-cpPNA Chimera and Stereopreferences in Hybridization with DNA/RNA", J. Org. Chem. 69(17):5725-34 (2004).
Gupta, et al., "Triple Helical Recognition of Pyrimidine Inversions in Polypurine Tracts of RNA by Nucleobase-modified PNA", Chem. Comm., 47:11125-11127 (2011).
Hacein-Bey-Abina, et al., "Sustained correction of X-linked severe combined immunodeficiency by ex vivo gene therapy", N. Engl. J. Med., 346:1185-1193 (2002).
He, et al., "The Structure of a γ-modified peptide nucleic acid duplex", Mol. BioSyst. 6:1619-1629 (2010).
Hoban, et al., "Correction of the sickle cell disease mutation in human hematopoietic stem/progenitor cells", Blood, 125:2597-2604 (2015).
Johnson, et al., "Efficiency of gene transfer for restoration of normal airway epithelial function in cystic fibrosis", Nat. Genet. 2:21-25 (1992).
Jordan, et al., "New hetero-oligomeric peptide nucleic acids with improved binding properties to complementary DNA", Bioorg. Med. Chem. Lett., 7:687-690 (1997).
Keshet, et al., "Embryonic RNA expression patterns of the c-kit receptor and its cognate ligand suggest multiple functional roles in mouse development", EMBO J. 10:2425-2435 (1991).
Krotz, et al., "Synthesis of 'retro-inverso' peptide nucleic acids: 2. Oligomerization and stability", Tetrahedron Lett. 36:6941-6944 (1995).
Lagriffoul, et al., "The synthesis, co-oligomerization and hybridization of a thymine-thymine heterodimer containing PNA", Bioorg. Med. Chem. Lett. 4:1081-1082 (1994).
Lagriffoule, et al., "Peptide Nucleic Acids with a Conformationally Constrained Chiral Cyclohexyl_Derived Backbone", Chem. Eur. J., 3:912-919 (1997).
Larson, et al., "In Utero Gene Therapy", Ochsner J., 2(2):107-110 (2000).
Lennartsson, et al., "Stem Cell Factor Receptor/C-Kit: From Basic Science To Clinical Implications", Physiological Reviews, 92(4):1619-1649 (2012).
Lowe, et al., "Amino acids bearing nucleobases for the synthesis of novel peptide nucleic acids", J. Chem. Soc. Perkin Trans., 1:539-546 (1997).
Maeder, et al., "Genome-editing Technologies for Gene and Cell," Therapy Molecular Therapy, 24 (3): 430-446 (2016).
Matsui, et al., "Embryonic expression of a haematopoietic growth factor encoded by the SI locus and the ligand for c-kit", Nature, 347:667-669 (1990).
Nielsen, et al., "Peptide nucleic acid (PNA). A DNA mimic with a peptide backbone", Bioconjug. Chem., 5:3-7 (1994).

Orr-Urtreger, et al., "Developmental expression of c-kit, a proto-oncogene encoded by the W locus", Development, 109:911-923 (1990).
Patel, et al., "Polymeric nanoparticles for drug delivery to the central nervous system", Advanced drug delivery reviews, 64(7):701-5 (2012).
Petersen, et al., "Synthesis and oligomerization of Nδ-Boc-Nα-(thymin-1-ylacetyl)ornithine", Bioorg. Med. Chem. Lett., 6(7):793-796 (1996).
Quijano, et al., "Therapeutic Peptide Nucleic Acids: Principles, Limitations, and Opportunities", Yale J. Biol. Med., 90:583-598 (2017).
Reyes, et al., "Towards a CRISPR view of early human development: applications, limitations and ethical concerns of genome editing in human embryos," Development, 144: 3-7 (2017).
Ricciardi, et al., "Targeted genome modification via triple helix formation", Methods Mol. Biol., 1176:89-106 (2014).
Richardson, et al., "Gene Repair in the New Age of Gene Therapy", Hepatology, 35(3):512-518 (2002).
Roybal, et al., "Stem cell and genetic therapies for the fetus", Semin. Fetal Neonatal. Med., 15:46-51 (2010).
Sanz, et al., "Cas9/gRNA targeted excision of cystic fibrosis-causing deep-intronic splicing mutations restores normal splicing of CFTR mRNA", PLoS One 12:e0184009 (2017).
Schaefer, et al., "Unexpected mutations after CRISPR-Cas9 editing in vivo", Nat. Methods, 14:547-548 (2017).
Song, et al., "Surface chemistry governs cellular tropism of nanoparticles in the brain", Nat. Commun, 8:15322 (2017).
Sugiyama, et al., "PNA monomers fully compatible with standard Fmoc-based solid-phase synthesis of pseudocomplementary PNA", Bioorg. Med. Chem. Lett., 27(15):3337-3341 (2017).
Tan, et al., "Homopolymeric pyrrolidine-amide oligonucleotide mimics: Fmoc-synthesis and DNA/RNA binding properties", Org. Biomol. Chem., 5: 239-248 (2007).
Abramova, et al., "Solid-phase-supported synthesis of morpholinoglycine oligonucleotide mimics", Beilstein J. Org. Chem., 10: 1151-1158 (2014).
Van Der Laan, et al., "An approach towards the synthesis of oligomers containing a N-2-hydroxyethyl-aminomethylphosphonate backbone: A novel PNA analogue", Tetrahedron Lett. 37:7857-7860 (1996).
Waddington, et al., "In Utero gene therapy: current challenges and perspectives," Molecular Therapy, 11(5): 661-676 (2005).
Walsh, "Fetal Gene Therapy," Gene Therapy, 6(7):1200-1 (1999).
Wefers, et al., "Gene editing in mouse zygotes using the CRISPR/Cas9 system," Methods, 121-122:55-67 (2017).
Yeh, et al., "Self-assembled Monothiol-Terminated Hyperbranched Polyglycerols on a Gold Surface: A Comparative Study on the Structure, Morphology, and Protein Adsorption Characteristics With Linear Poly(ethylene Glycol)s", Langmuir, 24(9):4907-16(2008).
Zhou, et al., "Highly penetrative, drug-loaded nanocarriers improve treatment of glioblastoma", PNAS, 110(29):11751-6 (2013).
Deng, et al., "The Effect of Hyperbranched Polyglycerol Coatings on Drug Delivery Using Degradable Polymer Nanoparticles", Biomaterials, 35(24): 6595-6602 (2014).
Roos, et al., "The multifaceted influence of histone deacetylases on DNA damage signalling and DNA repair", Nucleic Acids Research, 44(21):10017-10030 (2016).
Krishnendu, et al., "Core/shell nanoparticles in biomedical applications", Advances in Colloid and Interface Science, 209:8-39 (2014).
Budke, et al., "RI-1: a chemical inhibitor of RAD51 that disrupts homologous recombination in human cells", Nucleic Acids Research, 40(15):7347-7357 (2012).
Nielsen, et al., "Sequence-selective targeting of duplex DNA by peptide nucleic acids", Current opinion in molecular therapeutics, 12:184-191 (2010). Abstract Only.
Almeida-Porada, et al., "In utero stem cell transplantation and gene therapy: rationale, history, and recent advances toward clinical application", Mol. Ther. Methods Clin. Dev., 5:16020 (2016).
Andreani, et al., "Long-term survival of ex-thalassemic patients with persistent mixed chimerism after bone marrow transplantation", Bone Marrow Transplant, 25:401-404 (2000).

(56) References Cited

OTHER PUBLICATIONS

Ansari, et al., "Cellular GFP Toxicity and Immunogenicity: Potential Confounders in in Vivo Cell Tracking Experiments", Stem Cell Rev. and Rep., 12(5):553-559 (2016).
Bang, et al., "Ultrasound-guided fetal intravenous transfusion for severe rhesus haemolytic disease", Br. Med. J. (Clin. Res. Ed.) 284:373-374 (1982).
Blanpain, et al., "Multiple Nonfunctional Alleles of CCR5 Are Frequent in Various Human Populations", Blood, 96(5):1638-45 (2000).
Bordignon et al., "Transgene Expression of Green Fluorescent Protein and Germ Line Transmission in Cloned Calves Derived from In Vitro-Transfected Somatic Cells", Biol. Reprod., 68(6):2013-23 (2003).
Bowie, et al., "Hematopoietic stem cells proliferate until after birth and show a reversible phase-specific engraftment defect", J. Clin. Invest., 116:2808-2816 (2006).
Bruijn, et al., "Definitive hematopoietic stem cells first develop within the major arterial regions of the mouse embryo", EMBO J., 19:2465-2474 (2000).
Coumans, et al., "Green fluorescent protein expression triggers proteome changes in breast cancer cells", Exp. Cell Res., 320(1):33-45 (2014).
Coutelle, "Why Bother?: Is In Utero Gene Therapy Worth the Effort?" Molecular Therapy, 16(2):219-20 (2008).
Douar, et al., "Foetal gene delivery in mice by intra-amniotic administration of retroviral producer cells and adenovirus", Gene Ther., 4:883-890 (1997).
Dzierzak, et al., "Of lineage and legacy: the development of mammalian hematopoietic stem cells", Nat. Immunol., 9(2):129-136 (2008).
Endo, et al., "The developmental stage determines the distribution and duration of gene expression after early intraamniotic gene transfer using lentiviral vectors", Gene therapy, 17(1):61-71 (2010).
Fahmy, et al., "Design opportunities for actively targeted nanoparticle vaccines", Nanomedicine, 3(3):343-55 (2008).
Fan, et al., "Non-invasive prenatal measurement of the fetal genome", Nature, 487:320-324 (2012).
Farrelly, et al., "Intra-Amniotic Delivery of Biodegradable Microparticles and Nanoparticles to the Spinal Defect in a Rat Myelomeningocele Model," American Society of Gene and Cell Therapy, 20th Annual Meeting, Abstract 699, 2 pages, Apr. 24, 2017.
Fichter, et al., "Fetal spina bifida repair—current trends and prospects of intrauterine neurosurgery", Fetal Diagn. Ther., 23(4):271-86 (2008).
Flores, et al., "Early detection and staging of spontaneous embryo resorption by ultrasound biomicroscopy in murine pregnancy", Reprod. Biol. Endocrinol., 12(38): 1-12 (2014).
Gilbert, et al., "Genetic mouse embryo assay: improving performance and quality testing for assisted reproductive technology (ART) with a functional bioassay", Reprod. Biol. Endocrinol., 14(13):1-8 (2016).
Haapaniemi, et al., "CRISPR-Cas9 genome editing induces a p53-mediated DNA damage response", Nature medicine, 24:927-930 (2018).
Harrison, et al., "Gene editing & stem cells", J. Cyst. Fibros., 17:10-16 (2018).
Hui, et al., "Prenatal pharmacotherapy for fetal anomalies: a 2011 update", Prenat. Diagn., 31(7):735-43 (2011).
Ihry, et al., "p53 inhibits CRISPR-Cas9 engineering in human pluripotent stem cells", Nature medicine, 24:939-946 (2018).
Itoi, et al., "Offspring from Mouse Embryos Developed Using a Simple Incubator-Free Culture System with a Deoxidizing Agent", PLoS One, 7(10): p. e47512 (2012).
Jay, et al., "Controlled Delivery of VEGF via Modulation of Alginate Microparticle Ionic Crosslinking," J. Control Release, 134(1):26-34 (2009).
Jay, et al., "Dual delivery of VEGF and MCP-1 to support endothelial cell transplantation for therapeutic vascularization", Biomaterials, 31(11):3054-62 (2010).

Jukam, et al., "Zygotic Genome Activation in Vertebrates", Dev. Cell, 42(4):316-332 (2017).
Kalma, et al., "Optimal timing for blastomere biopsy of 8-cell embryos for preimplantation genetic diagnosis", Hum. Reprod., 33(1):32-38 (2018).
Kempe, et al., "First-trimester treatment of fetal anemia secondary to parvovirus B19 infection", Ultrasound Obstet. Gynecol., 29:226-228 (2007).
Langley, et al., "New insights into the maternal to zygotic transition", Development, 141(20):3834-41 (2014).
Li, et al., "Fast and accurate short read alignment with Burrows-Wheeler transform", Bioinformatics, 26:589-595 (2010).
Lyons, et al., "The reproductive significance of human Fallopian tube cilia", Hum. Reprod. Update, 12(4):363-72 (2006).
Manna, et al., "MiniPEG-γPNA", Methods in Molecular Biology, 1050:1-12 (2014).
Marangi, et al., "Innovative Therapeutic Strategies for Cystic Fibrosis: Moving Forward to CRISPR Technique", Front. Pharmacol., 9:396 (2018).
Modell, et al., "Global epidemiology of haemoglobin disorders and derived service indicators", Bull World Health Organ., 86:480-487 (2008).
Nagy, et al., "Pronuclear morphology evaluation with subsequent evaluation of embryo morphology significantly increases implantation rates", Fertil. Steril., 80(1): 67-74 (2003).
Orkin, et al., "Hematopoiesis: an evolving paradigm for stem cell biology", Cell, 132: 631-644 (2008).
Perets, et al., "Enhancing the vascularization of three-dimensional porous alginate scaffolds by incorporating controlled release basic fibroblast growth factor microspheres", J. Biomed. Mater. Res. A., 65(4):489-97 (2003).
Piotrowski-Daspit, et al., "Poly(amine-co-ester) Nanoparticles for the Delivery of Peptide Nucleic Acid Gene Editing Agents to Correct Beta-thalassemia," American Society of Gene & Cell Therapy Annual Meeting 2018 Abstracts, #614, 2 pages, Apr. 30, 2018.
Radcliff, et al., "Hospital use, associated costs, and payer status for infants born with spina bifida", Birth Defects Res. A., 94(12):1044-53 (2012).
Ribault, et al., "Experience with intraamniotic thyroxine treatment in nonimmune fetal goitrous hypothyroidism in 12 cases", The Journal Of Clinical Endocrinology And Metabolism, 94(10):3731-9 (2009).
Ricciardi, et al., "Peptide Nucleic Acids as a Tool for Site-Specific Gene Editing," Molecules, 23(3):632 (2018a).
Ricciardi, et al., "In utero nanoparticle delivery for site-specific genome editing", Nat. Commun., 9(1):2481 (2018b).
Saadai, et al., "Fetal surgery for myelomeningocele", Clin. Perinatol., 39(2):279-88 (2012).
Sarvari, et al., "A Technique for Facile and Precise Transfer of Mouse Embryos", Med. Biotechnol., 5(1): 62-65 (2013).
Shamonki, et al., "Proof of concept: preimplantation genetic screening without embryo biopsy through analysis of cell-free DNA in spent embryo culture media", Fertil Steril, 106(6): 1312-1318 (2016).
Stehle, et al., "Albumin-based drug carriers: comparison between serum albumins of different species on pharmacokinetics and tumor uptake of the conjugate", Anticancer Drugs, 10(8):785-90 (1999).
Stitelman, et al., "Robust in vivo transduction of nervous system and neural stem cells by early gestational intra amniotic gene transfer using lentiviral vector", Molecular therapy : the journal of the American Society of Gene Therapy, 18(9):1615-23 (2010).
Stitelman, et al., "Developmental Stage Determines Efficiency of Gene Transfer to Muscle Satellite Cells by in Utero Delivery of Adeno-Associated Virus Vector Serotype 2/9," Mol. Ther. Methods Clin. Dev., 1:14040 (2014).
Stitelman, et al., "Life-Long Transgene Expression in Skeletal Muscle Without Transduction of Satellite Cells Following Embryonic Myogenic Progenitor Transduction by Lentivirus Administered in Utero," Stem Cells Dev., 24(16):1878-87 (2015).
Strug, et al., "Recent advances in developing therapeutics for cystic fibrosis", Hum. Mol. Genet., 27:R173-R186 (2018).

(56) References Cited

OTHER PUBLICATIONS

Tatyana, et al., "Solid-phase-supported synthesis of morpholinoglycine oligonucleotide mimics", Beilstein J. Org. Chem., 10: 1151-1158 (2014).
Tavian, et al., "Embryonic development of the human hematopoietic system", Int. J. Dev. Biol. 49:243-250 (2005).
Themis, et al., "Successful Expression of Beta-Galactosidase and Factor IX Transgenes in Fetal and Neonatal Sheep After Ultrasound-Guided Percutaneous Adenovirus Vector Administration Into the Umbilical Vein", Gene Ther., 6(7):1239-48 (1999).
Turner, et al., "The amniotic fluid as a source of neural stem cells in the setting of experimental neural tube defects", Stem cells and development, 22(4):548-53 (2013).
Wassarman, et al., "Mouse zona pellucida genes and glycoproteins", Cytogenet. Genome Res., 105(2-4):228-34 (2004).
Watanabe, et al., "A tissue engineering approach for prenatal closure of myelomeningocele with gelatin sponges incorporating basic fibroblast growth factor", Tissue engineering Part A, 16(5):1645-55 (2010).
Watanabe, et al., "Tissue Engineering Strategies for Fetal Myelomeningocele Repair in Animal Models", Fetal Diagnosis And Therapy, (2014).
Watanabe, et al., "Complete tissue coverage achieved by scaffold-based tissue engineering in the fetal sheep model of Myelomeningocele", Biomaterials, 76:133-43 (2015).
Williams, et al., "Updated estimates of neural tube defects prevented by mandatory folic Acid fortification—United States, 1995-2011", MMWR Morb Mortal Wkly Rep., 64(1):1-5 (2015).
Zeng, et al., "Correction of the Marfan Syndrome Pathogenic FBN1 Mutation by Base Editing in Human Cells and Heterozygous Embryos", Mol. Ther., 26(11):2631-2637 (2018).
Zhang, et al., "PEAR: a fast and accurate Illumina Paired-End reAd mergeR", Bioinformatics 30:614-620 (2014).
Van Kamp, et al., "Complications of intrauterine intravascular transfusion for fetal anemia due to maternal red-cell alloimmunization", Am. J. Obstet. Gynecol., 192:171-177 (2005).
Danzer, et al., "Retinoic acid induced myelomeningocele infetal rats: characterization by histopathological analysis and magnetic resonance imaging", Experimentalneurology, 194(2):467-75 (2005).
Devgan, et al., "Impact of embryonic expression of enhanced green fluorescent protein on early mouse development", Biochem. Biophys. Res. Commun., 313(4): p. 1030-6 (2004).
Dionigi, et al., "Trans-amniotic stem cell therapy (TRASCET) minimizes Chiari-II malformation in experimental spina bifida", J. Pediatr. Surg., 50(6):1037-41 (2015).
Hanono, et al., "Antenatal treatment of fetal goiter: a therapeutic challenge", J. Matern. Fetal Neonatal. Med., 22(1):76-80 (2009).
Hashimoto, et al., "Successful in utero treatment of fetal goitrous hypothyroidism: case report and review of the literature", Fetal Diagn. Ther., 21(4):360-5 (2006).
Kitterman, "The effects of mechanical forces on fetal lung growth", Clin. Perinatol., 23:727-740 (1996).
Mackenzie, et al., "Human mesenchymal stem cells persist, demonstrate site-specific multipotential differentiation, and are present in sites of wound healing and tissue regeneration after transplantation into fetal sheep", Blood Cells Mol. Dis., 27(3):601-4 (2001).
Mahoney, et al., "Transplantation of brain cells assembled around a programmable synthetic microenvironment", Nature biotechnology, 19(10):934-9 (2001).
Manning, et al., "Pathophysiology, prevention, and potential treatment of neural tube defects", Ment. Retard Dev. Disabil. Res. Rev., 6(1):6-14 (2000).
Mcarthur, et al., "Blastocyst trophectoderm biopsy and preimplantation genetic diagnosis for familial monogenic disorders and chromosomal translocations", Prenat. Diagn., 28(5):434-42 (2008).
Mulvihill, et al., "Trophic effect of amniotic fluid on fetal gastrointestinal development", J. Surg. Res., 40:291-296 (1986).
Peranteau, et al., "Prenatal surgery for myelomeningocele", Curr. Opin. Obstet. Gynecol., 28(2):111-8 (2016).

Yang, et al., "In Utero Gene Delivery Using Chitosan-DNA Nanoparticles in Mice", Journal of Surgical Research, 171(2): 691-699 (2011).
Song, et al., "Evidence against the rescue of defective DeltaF508-CFTR cellular processing by curcumin in cell culture and mouse models", Science, 304:600-2 (2004).
Lin, et al., "Enhanced homology-directed human genome engineering by controlled timing of CRISPR/Cas9 delivery", eLife, 3:e04766 (2014).
Mcneer, et al., "Systemic delivery of triplex-forming PNA and donor DNA by nanoparticles mediates site-specific genome editing of human hematopoietic cells in vivo", Gene Therapy, 20(6): 658-669 (2012a).
Rogers, et al., "Local delivery of gene-modifying triplex-forming molecules to the epidermis", Journal of Investigative Dermatology, 133(3):685-691 (2013).
Kuhn, et al., "Sequence specificity at targeting double-stranded DNA with a γ-PNA oligomer modified with guanidinium G-clamp nucleobases", Artificial DNA:PNA & XNA, 1(1):45-53 (2010).
Bahal, et al., "Nanoparticle for delivery of antisense γPNA oligomers targeting CCR5", Artificial DNA:PNA & XNA, 4(2): 49-58 (2013).
Bahal, et al., "Single-Stranded γPNAs for In Vivo Site-Specific Genome Editing viaWatson-Crick Recognition", Current Gene Therapy, 14(5): 331-342 (2014a).
Gupta, et al., "Nanotechnology for delivery of peptide nucleic acids (PNAs)", Journal of Controlled Release, 240:302-311 (2016).
Bahal, et al., "In vivo correction of anaemia in β-thalassemic mice by γPNA-mediated gene editing with nanoparticle delivery", Nature Communications, 7:13304, 14 pages (2016).
Mcneer, et al., "Nanoparticles that deliver triplex-forming peptide nucleic acid molecules correct F508del CFTR in airway epithelium", Nature Communications, 6:6952, 25 pages (2015a).
Mcneer, et al., "Nanoparticles that deliver triplex-forming peptide nucleic acid molecules correct F508del CFTR in airway epithelium", Supplementary data, Nature Communications, 1-15 (2015b).
International Search Report for PCT/US2017/018165 dated May 22, 2017.
Hollingsworth, et al., "A nuclear factor that binds purine-rich, single-stranded oligonucleotides derived from SI-sensitive elements upstream of the CFTR gene and the MUCI gene", Nucleic Acids Research, 22(7): 1138-1146 (1994).
Kaihatsu, et al., "Extending recognition by peptide nucleic acids (PNAs): Binding to duplex DNA and inhibition of transcription by tail-clamp PNA-peptide conjugates." Biochemistry, 42(47):13996-4003 (2003).
Bentin, et al., "Combined Triplex/Duplex Invasion of Double-Stranded DNA by Tail Clamp Peptide Nucleic Acid", Biochemistry, 42(47): 13987-13995 (2003).
Rogers, et al., "Site-Directed Recombination Via Bifunctional Pna-Dna Conjugates" PNAS, 99(26): 16695-16700 (2002).
International Seach Report for PCT/US2010/031888 dated Aug. 3, 2010.
International Search report for PCT/US2018/026116 dated Jul. 9, 2018.
Mcneer, et al., "Correction of F508DEL CFTR using nanoparticles delivering triplex-forming peptide nucleic acid molecules", poster presented at North American Cystic Fibrosis Meeting, Oct. 8-10, (2015d).
Bahal, et al. "Nanoparticle for delivery of antisense γPNA oligomers targeting CCR5", Artificial DNA: PNA & XNA, 4:2, 49-57(2013).
Bahal, et al., "In vivo correction of anaemia in β-thalassemic mice by γPNA-mediated gene editing with nanoparticle delivery", Nat Commun., 7:13304. doi: 10.1038 (2016).
Bahal, et al., "Single-Stranded yPNAs for In Vivo Site-Specific Genome Editing viaWatson-Crick Recognition", Curr. Gene Ther., 14:331-42 (2014).
Bentin, et al., "Combined triplex/duplex invasion of double-stranded DNA by "tail-clamp" peptide nucleic acid", Biochemistry, 42(47):13987-95 (2003).
Gupta, et al., "Nanotechnology for delivery of peptide nucleic acids (PNAs)", J Control Release, 240:302-11 (2016).

(56) References Cited

OTHER PUBLICATIONS

Hollingsworth, et al., "A nuclear factor that binds purine-rich, single-stranded oligonucleotides derived from S1-sensitive elements upstream of the CFTR gene and the MUC1 gene", Nucleic Acids Res., 22(7):1138-46 (1994).
International Search Report PCT/US2017/018165 mailed May 22, 2017.
Lin, et al., "Enhanced homology-directed human genome engineering by controlled timing of CRISPR/Cas9 delivery", eLife, 3:e04766. doi: 10.7554 (2014).
Mcneer, et al., "Correction of F508DEL CFTR using nanoparticles delivering triplex-forming peptide nucleic acid molecules", poster presented at North American Cystic Fibrosis Meeting, Oct. 8-10, (2015a2).
Mcneer, et al., "Systemic delivery of triplex-forming PNA and donor DNA by nanoparticles mediates site-specific genome editing of human hematopoietic cells in vivo", Gene Therapy, 20:658-669 (2013).
Rogers, et al., "Local delivery of gene-modifying triplex-forming molecules to the epidermis", J Ivest Dermatol., 133(3):685-91(2013).
Yang, et al., "In utero gene delivery using chitosan-DNA nanoparticles in mice", J Surgical Res., 171:691-9 (2011).
Gamble, et al., "Development of Cu+2-Basd Distance Methods and force Field Parametes for the Determination of PNA Conformations and Dynamics by EPR and MD Simulations", Journal of Physical Chemistry Part B, 124(35):7544-7556 (2020).
Bahal, et al., "Site specific genome editing of hematopoietic stem cells for beta thalassemia gene therapy," American Society of Gene and Cell Therapy, Annual Meeting, May 21-24, (2014a).
Carrington, et al., "Novel Alleles of the Chemokine-Receptor Gene CCR5," Am. J. Hum. Genet., 61(6):1261-7(1997).
Nielsen, et al., "Sequence-selective targeting of duplex DNA by peptide nucleic acids", Current opinion in molecular therapeutics, 12:184-191 (2010).
Shenoy, et al., "Calcium Modulated Chloride Pathways Contribute to Chloride Flux in Murine CF-Affected Macrophages", Pediatric research, 70:447-452 (2011).
Bahal, et al., "In vivo correction of anaemia in b-thalassemic mice by gPNA-mediated gene editing with nanoparticle delivery", Nature Communications, 7:1-14 (2016).
Chin, et al., "Correction of a splice-site mutation in the beta-globin gene stimulated by triplex-forming peptide nucleic acids", PNAS, 105(36): 13514-13519 (2008).
Daksis, et al., "Heteropolymeric Triplex-Based Genomic AssayH to Detect Pathogens or Single-Nucleotide Polymorphisms in Human Genomic Samples", PLOS ONE, 2:3 (2007).
He, et al., "The Structure of a _ modified peptide nucleic acid duplex", Mol. BioSyst. 6:1619-1629 (2010).
Papaioannou, et al., "Oligonucleotide-directed gene-editing technology: mechanisms and future prospects", Expert Opinion on Biological, The Informa Healthcare, UK., 12(3):329-342 (2012).
Kamei, et al., "Mechanistic Study of the Uptake/Permeation of Cell-Penetrating Peptides Across a Caco-2 Monolayer and Their Stimulatory Effect on Epithelial Insulin Transport", Journal Of Pharmaceutical Sciences, 102(11):3998-4008 (2013).
Nyce, et al., "DNA antisense therapy for asthma in an animal model", Nature, 385:721-725 (1997).
Scriver, et al., "The metabolic and molecular basis of inherited disease", 8th ed. New York: McGraw-Hill Pub, 2001: 3635-3668.
Asensio, et al. "Thermodynamic, kinetic, and conformational properties of a parallel intermolecular DNA triplex containing 5' and 3' junctions", Biochemistry, 37(43):15188-98 (1998).
Asensio, et al., "The Contribution of Cytosine Protonation to the Stability of Parallel DNA Triple Helices," J. Mol. Biol., 275(5): 811-822 (1998).
Belousov, et al., "Triplex targeting of a native gene in permeabilized intact cells: covalent modification of the gene for the chemokine receptor CCR5," Nucleic Acids Res., 26(5): 1324-8 (1998).
Bennett & Davis, "Erythrocyte ankyrin: Immunoreactive analogues are associated with mitotic structures in cultured cells and with microtubules in brain," Proc. Natl. Acad. Sci. USA. 78:7550-7554 (1981).
Bredberg, et al., "Psoralen adducts in a shuttle vector plasmid propagated in primate cells: high mutagenicity of DNA cross-links", Carcinogenesis 8(12): 1923-27 ( 1987).
Brenneman, et al., "Stimulation of intrachromosomal homologous recombination in human cells by electroporation with site-specific endonucleases," Proc. Natl. Acad. Sci. USA 93(8): 3608-12 (1996).
Cole-Strauss, et al., "Correction of the mutation responsible for sickle cell anemia by an RNADNA oligonucleotide.", Science, 273(5280): 1386-1389.
Staff, "An introduction to gene therapy and its potential prenatal use", Acta Obstat. Gynecol. Scand., 80:485-491 (2001).
Waddington, et al., In utero gene transfer of human factor IX to fetal mice can induce postnatal tolerance of the exogenous clotthing factor, Blood, 101:1359-1366 (2013).
David, et al., "Candidate Disease for Prenatel Gene Therapy", Method in Molecular Biology, 891:10-39 (2012).
Burd, et al., "Fetal uptake of intra-amniotically delivered dendrimers in a mouse model of intrauterine inflammation and preterm birth", Nanomedicine: NBM, 10:1343-1351 (2014).
Zhang, et al., "engineering biodegradable nanoparticles for drug and gene delivery", Chem. Eng. Prog., 109(3):25-30(2013).
Skarsgard, "In utero gene delivery using chitosan DNA nanoparticles in mice", Clinical and Investigative Medicine, 34, Abstract (2008).

* cited by examiner

COMPOSITIONS AND METHODS FOR IN UTERO DELIVERY

CROSS-REFERENCE TO RELATED APPLICATIONS

This application is a continuation of U.S. Ser. No. 16/603,152 filed Oct. 4, 2019, which is a National Phase application under 35 U.S.C. § 371 of PCT/US2018/026116, filed Apr. 4, 2018, which claims the benefit of and priority to U.S. Ser. No. 62/481,562, filed Apr. 4, 2017, U.S. Ser. No. 62/489,377, filed Apr. 24, 2017, and U.S. Ser. No. 62/589,275, filed Nov. 21, 2017, each of which is specifically incorporated by reference herein in its entirety.

STATEMENT REGARDING FEDERALLY SPONSORED RESEARCH

This invention was made with government support under AI112443 and HL125892 awarded by National Institutes of Health. The government has certain rights in the invention.

FIELD OF THE INVENTION

The field of the invention is generally related to compositions and methods for in utero delivery of active agents, particularly those in which the active agent is encapsulated within, surrounded by, and/or dispersed in polymeric microparticles or nanoparticles.

BACKGROUND OF THE INVENTION

Every year an estimated 8 million children are born worldwide with severe structural birth defects or genetic disorders. Structural birth defects are abnormalities in the structure of body parts such as cleft palate, heart defects, club foot, missing and abnormal limbs. Most structural defects develop in the earliest weeks of pregnancy when all of the organs and the skeleton are forming. Myelomeningocele (MMC), an open form of spina bifida, is both the most common and most severe form of neural tube defect associated with long-term survival. MMC occurs in up to 3000 live births in the United States each year, and this does not include the estimated 63% of MMC pregnancies in which the fetus terminated, either spontaneously or intentionally. Patients with MMC have a boney spinal defect but no effective skin or soft tissue covering to protect the spinal cord and meninges which herniate posteriorly through the defect. Despite improved multi-disciplinary care, the neonatal mortality rate for MMC patients remains as high as 10%, and only approximately half of those who survive will be able to function independently as adults. Fetal correction of MMC results in better outcomes, and some have proposed that stem cells at the MMC skin edges can be recruited with the aid of growth factors to close the MMC. Experiments with gelatin sponges impregnated with fibroblast growth factor (FGF) have been investigated in rat and sheep models of MMC.

Patients with the mildest type of neural tube defect, spina bifida occulta, have an open defect in the boney vertebral arches that normally protect the underlying spinal cord. Despite having this boney defect, these patients are usually neurologically normal and have no signs or symptoms except for a small dimple or tuft of hair overlying the defect. Hemoglobinopathies are the most commonly inherited single-gene disorders, with a global carrier frequency of over 5%. Depending on the severity of the disease, children affected by β-thalassemia may require lifelong transfusions or bone marrow transplantation, which can lead to serious complications such as iron overload, sepsis, or graft-versus-host disease. Recent advances in non-invasive genetic testing allow for early gestation diagnosis of genetic disorders such as thalassemia, providing a window during which genetic correction could be achieved prior to birth.

In utero gene therapy thus far has focused on stem cell transplantation and viral-mediated gene delivery, approaches that do not allow for correction of a gene in its endogenous environment. However, at least one report describes the in utero delivery of oligonucleotides for the treatment of Duchenne Muscular Dystrophy (Cai et al., "In Utero Delivery of Oligodeoxynucleotides for Gene Correction", Chapter 26, Francesca Storici (ed.), *Gene Correction: Methods and Protocols, Methods in Molecular Biology*, 1114 (2014)). Site-specific gene editing to correct disease-causing mutations can be administered to postnatal animals via the intravenous or inhalational administration of polymeric, biodegradable nanoparticles loaded with peptide nucleic acids (PNAs) and single-stranded donor DNAs. In a recent report, chitosan-DNA nanoparticles were used for in utero gene therapy (Yang et al. *Journal of Surgical Research*, 171:691-699 (2011)).

Improved compositions and methods for in utero therapeutics and diagnostics are needed, where, for example, diseases or disorders can be addressed prior to the point where irreparable harm is done to tissues and/or organ systems of the embryo or fetus.

Therefore, it is an object of the invention to provide compositions and methods for in utero delivery.

SUMMARY OF THE INVENTION

Compositions and methods for in utero delivery of active agents allow therapeutic and diagnostic molecules to be delivered to an embryo or fetus in need thereof. In some embodiments, the methods deliver an effective amount of a composition to the cells of the embryo or fetus, without delivering an effective amount of the composition to the mother of the embryo or fetus.

The therapeutic or diagnostic active agent can be encapsulated, entrapped or complexed to biocompatible particles such as nano- or microparticles. The particles can be formulated for cellular internalization or to remain predominately extracellular, releasing their cargo in a paracrine-like fashion. In some embodiments, the particles do not cross the placenta. These nano- and microparticles can be engineered to attach to specific targets or to release their chemical payload at different rates. The active agent can also be administered to a subject in utero without particles.

Active agents for in utero delivery include, but are not limited to therapeutic, nutritional, diagnostic, or prophylactic agents, and gene editing compositions. The active agents can be small molecule active agents or biomacromolecules, such as proteins, polypeptides, sugars or polysaccharides, liporproteins or nucleic acids. Suitable small molecule active agents include organic and organometallic compounds. The small molecule active agents can be a hydrophilic, hydrophobic, or amphiphilic compound. The nucleic acids can be oligonucleotide drugs such as DNA, RNAs, antisense, aptamers, small interfering RNAs, ribozymes, external guide sequences for ribonuclease P, and triplex forming agents. In some embodiments, the methods are utilized to deliver active agents such as small molecules, peptides, nucleic acids, peptide nucleic acids (PNAs), locked nucleic acids (LNAs), morpholino oligomers (PMOs), etc., absent a gene editing composition. In some embodiments, the only active agent is a gene editing composition. Exemplary diagnostic agents include paramagnetic molecules, fluorescent compounds, magnetic molecules, and radionuclides, x-ray imaging agents, and contrast agents.

The methods typically include administering to an embryo or fetus, or the pregnant mother thereof, an effective amount of an active agent, encapsulated or entrapped in or otherwise associated with particles. In some methods, active agent or particles including active agent are delivered in utero by injecting and/or infusing the particles into a vein or artery, such as such the vitelline vein or the umbilical vein, or into the amniotic sac of an embryo or fetus.

Particle compositions for extracellular and intracellular delivery of active agents include, but are not limited to, gene editing compositions are also provided and particularly advantageous for use with in utero applications. The particle are preferably made of biodegradable polymers such as polymers or copolymers of lactic acid, glycolic acid, degradable polyesters, polyanhydrides, poly(ortho)esters, polyesters, polyurethanes, poly(butic acid), poly(valeric acid), poly(caprolactone), poly(hydroxyalkanoates), poly(lactide-co-caprolactone), poly(amine-co-ester) polymers, or a combination of any two or more of the foregoing. The particles can be or include poly(lactic-co-glycolic acid) PLGA. In some embodiments, the particles include poly(lactic-co-glycolic acid) (PLGA), poly(beta-amino) ester (PBAE), or a combination thereof. The particles can be formed of or contain one or more poly(amine-co-ester), poly(amine-co-amide), poly(amine-co-ester-co-ortho ester) or a combination thereof. Particles can include or be formed of alginate, chitosan, poly(HEMA) or other acrylate polymers and copolymers. Particles can further include a targeting moiety, a cell penetrating peptide, or a combination thereof. The particles used in the compositions can be of single species or a mixture of two or more different species of particles.

The particles can include an active agent, such as a gene editing composition, suitable for treatment of and can be administered in an effective amount to treat a disease or disorder.

In some embodiments, the formulations and methods provided for the controlled local release of growth factors to cause skin or soft tissue to grow over the exposed spinal cord of the fetal or embryonic subject. The formulation can include biocompatible particles which preferentially binds to MMC defects in utero and effectively release therapeutic agents to induce at least partial skin or soft tissue coverage of the defect. The formulation can be delivered in a minimally invasive fashion through an intra-amniotic injection.

Exemplary diseases and disorders which can be treated include cystic fibrosis.

In some embodiments, the composition is administered to a fetus or to the mother once or more when the fetus is about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, and/or 36 weeks of age.

DETAILED DESCRIPTION OF THE INVENTION

I. Definitions

Figure 1:
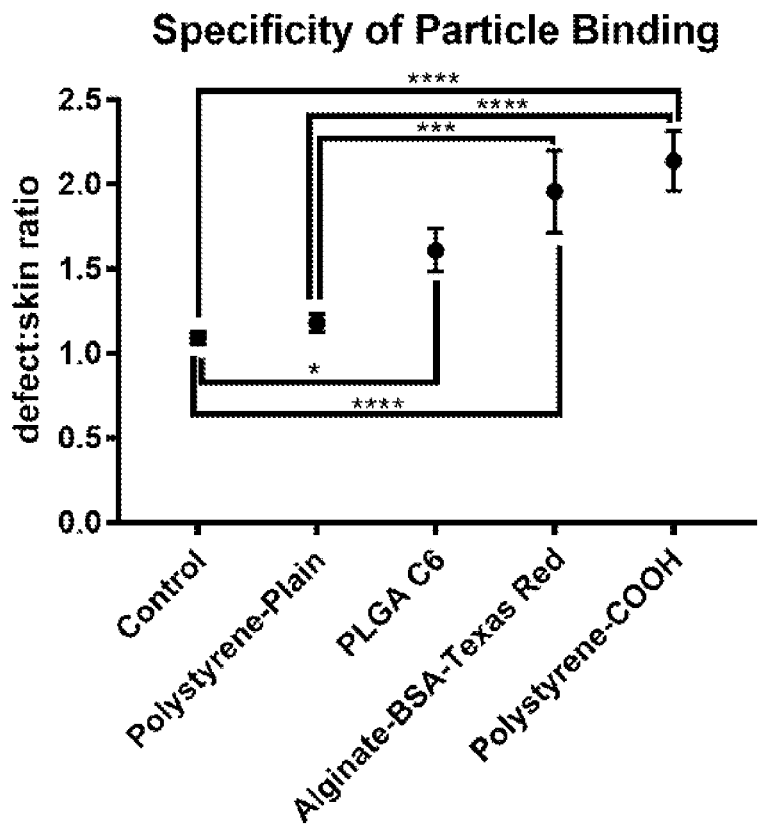
FIG. 1 is a graph showing the binding specificity (using defect-to-skin brightness ratio used as a surrogate for binding specificity) of fluorescent particles to the MMC defect for different particle compositions.
Figure 2:
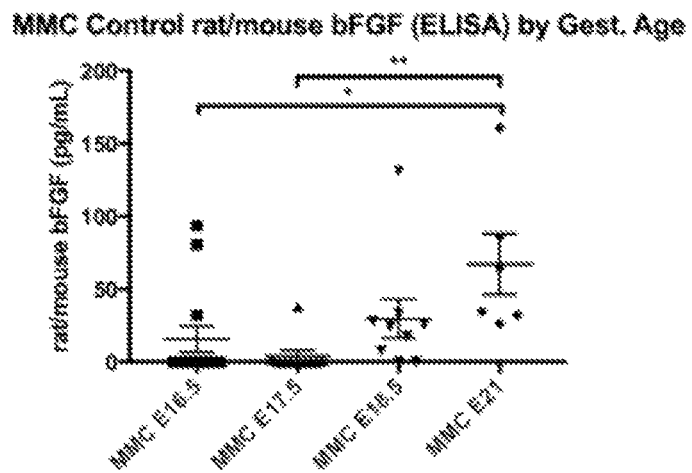
FIG. 2 is a graph showing the amount of rat/mouse basic fibroblast growth factor (bFGF) (pg/mL), obtained from ELISA, of non-injected MMC fetuses at different timepoints around the time of injection. Despite a decrease at E17.5, there appears to be an overall increase in bFGF levels toward full term, with a mean level of 67.3 pg/mL by E21.

As used herein, "affinity tags" are defined herein as molecular species which form highly specific, non-covalent, physiochemical interactions with defined binding partners. Affinity tags which form highly specific, non-covalent, physiochemical interactions with one another are defined herein as "complementary".

As used herein, "coupling agents" are defined herein as molecular entities which associate with polymeric particles and provide substrates that facilitate the modular assembly and disassembly of functional elements onto the particle. Coupling agents can be conjugated to affinity tags. Affinity tags allow for flexible assembly and disassembly of functional elements which are conjugated to affinity tags that form highly specific, noncovalent, physiochemical interactions with affinity tags conjugated to adaptor elements. Coupling agents can also be covalently coupled to functional elements in the absence of affinity tags.

As used herein, the term "isolated" describes a compound of interest (e.g., either a polynucleotide or a polypeptide) that is in an environment different from that in which the compound naturally occurs, e.g., separated from its natural milieu such as by concentrating a peptide to a concentration at which it is not found in nature. "Isolated" is meant to include compounds that are within samples that are substantially enriched for the compound of interest and/or in which the compound of interest is partially or substantially purified.

As used herein with respect to nucleic acids, the term "isolated" includes any non-naturally-occurring nucleic acid sequence, since such non-naturally-occurring sequences are not found in nature and do not have immediately contiguous sequences in a naturally-occurring genome.

As used herein, the term "host cell" refers to prokaryotic and eukaryotic cells into which a nucleic acid can be introduced.

As used herein, "transformed" and "transfected" encompass the introduction of a nucleic acid into a cell by one of a number of techniques known in the art.

As used herein, the phrase that a molecule "specifically binds" to a target refers to a binding reaction which is determinative of the presence of the molecule in the presence of a heterogeneous population of other biologics. Thus, under designated immunoassay conditions, a specified molecule binds preferentially to a particular target and does not bind in a significant amount to other biologics present in the sample. Specific binding of an antibody to a target under such conditions requires the antibody be selected for its specificity to the target. A variety of immunoassay formats may be used to select antibodies specifically immunoreactive with a particular protein. For example, solid-phase ELISA immunoassays are routinely used to select monoclonal antibodies specifically immunoreactive with a protein. See, e.g., Harlow and Lane (1988) Antibodies, A Laboratory Manual, Cold Spring Harbor Publications, New York, for a description of immunoassay formats and conditions that can be used to determine specific immunoreactivity. Specific binding between two entities means an affinity of at least $10^6$, $10^7$, 108, $10^9$, or $10^{10}$ M$^{-1}$. Affinities greater than $10^8$ M$^{-1}$ are preferred.

As used herein, "targeting molecule" is a substance which can direct a particle to a receptor site on a selected cell or tissue type, can serve as an attachment molecule, or serve to couple or attach another molecule. As used herein, "direct" refers to causing a molecule to preferentially attach to a selected cell or tissue type. This can be used to direct cellular materials, molecules, or drugs, as discussed below.

As used herein, the terms "antibody" or "immunoglobulin" are used to include intact antibodies and binding fragments thereof. Typically, fragments compete with the intact antibody from which they were derived for specific binding to an antigen fragment including separate heavy chains, light chains Fab, Fab' F(ab')2, Fabc, and Fv. Fragments are produced by recombinant DNA techniques, or by enzymatic or chemical separation of intact immunoglobulins. The term "antibody" also includes one or more immunoglobulin chains that are chemically conjugated to, or expressed as, fusion proteins with other proteins. The term "antibody" also includes a bispecific antibody. A bispecific or bifunctional antibody is an artificial hybrid antibody having two different heavy/light chain pairs and two different binding sites. Bispecific antibodies can be produced by a variety of methods including fusion of hybridomas or linking of Fab' fragments. See, e.g., Songsivilai and Lachmann, *Clin. Exp. Immunol.*, 79:315-321 (1990); Kostelny, et al., *J. Immunol.*, 148, 1547-1553 (1992).

As used herein, the terms "epitope" or "antigenic determinant" refer to a site on an antigen to which B and/or T cells respond. B-cell epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5 or 8-10, amino acids, in a unique spatial conformation. Methods of determining spatial conformation of epitopes include, for example, x-ray crystallography and 2-dimensional nuclear magnetic resonance. See, e.g., Epitope Mapping Protocols in Methods in Molecular Biology, Vol. 66, Glenn E. Morris, Ed. (1996). Antibodies that recognize the same epitope can be identified in a simple immunoassay showing the ability of one antibody to block the binding of another antibody to a target antigen. T-cells recognize continuous epitopes of about nine amino acids for CD8 cells or about 13-15 amino acids for CD4 cells. T cells that recognize the epitope can be identified by in vitro assays that measure antigen-dependent proliferation, as determined by $^3$H-thymidine incorporation by primed T cells in response to an epitope (Burke, et al., *J. Inf Dis.*, 170:1110-19 (1994)), by antigen-dependent killing (cytotoxic T lymphocyte assay, Tigges, et al., *J. Immunol.*, 156, 3901-3910) or by cytokine secretion.

As used herein, the term "small molecule," as used herein, generally refers to an organic molecule that is less than about 2000 g/mol in molecular weight, less than about 1500 g/mol, less than about 1000 g/mol, less than about 800 g/mol, or less than about 500 g/mol. Small molecules are non-polymeric and/or non-oligomeric.

As used herein, the term "carrier" or "excipient" refers to an organic or inorganic ingredient, natural or synthetic inactive ingredient in a formulation, with which one or more active ingredients are combined.

As used herein, the term "pharmaceutically acceptable" means a non-toxic material that does not interfere with the effectiveness of the biological activity of the active ingredients.

As used herein, the terms "effective amount" or "therapeutically effective amount" means a dosage sufficient to alleviate one or more symptoms of a disorder, disease, or condition being treated, or to otherwise provide a desired pharmacologic and/or physiologic effect. The precise dosage will vary according to a variety of factors such as subject-dependent variables (e.g., age, immune system health, etc.), the disease or disorder being treated, as well as the route of administration and the pharmacokinetics of the agent being administered.

As used herein, the term "prevention" or "preventing" means to administer a composition to a subject or a system at risk for or having a predisposition for one or more symptom caused by a disease or disorder to cause cessation of a particular symptom of the disease or disorder, a reduction or prevention of one or more symptoms of the disease or disorder, a reduction in the severity of the disease or disorder, the complete ablation of the disease or disorder, stabilization or delay of the development or progression of the disease or disorder.

The term "subject" or "patient" refers to any mammal who is the target of administration. Thus, the subject can be a human. The subject can be domesticated, agricultural, or wild animals. Domesticated animals include, for example, dogs, cats, rabbits, ferrets, guinea pigs, hamsters, pigs, monkeys or other primates, and gerbils. Agricultural animals include, for example, horses, cattle, pigs, sheep, rabbits, and goats. The term does not denote a particular age or sex. In some embodiments, the subject is an embryo or fetus.

II. Particle Delivery Vehicles

Compositions and methods for in utero treatment of a fetus or embryo are provided. The methods can include injecting or infusing into the vitelline vein of a fetus or embryo, injecting or infusing into its amniotic sac (e.g., intraamniotic sac injection), or a combination thereof and a composition having an effective amount of an active agent. In some embodiments, the composition is the active agent. In some embodiments, an effective amount of the same or a different active agents are administered by injection or infusion into the vitelline vein and by injection or infusion into the amniotic sac. The active agent can be a therapeutic agent, a nutritional agent, a diagnostic agent, or a prophylactic agent. The active agent can be a small molecule, a protein, or a nucleic acid. The active agent can be an antisense agent or a gene editing composition.

The compositions can include a biodegradable or bioerodible material in which the active agent is embedded or encapsulated. Any of the active agents including, but not limited to, therapeutic, nutritional, diagnostic, prophylactic agents, etc., can be, but need not necessarily be, delivered to the target cells using a particle-based delivery vehicle. Thus, the active agent can be encapsulated and/or entrapped and/or dispersed in a particle(s). Compositions can include a plurality of particles having an active agent encapsulated and/or entrapped and/or dispersed therein, in a pharmaceutically-acceptable carrier, and formulated for infusion or injection into a vitelline artery or a vitelline vein or for intraamniotic sac injection.

The particles can be capable of controlled release of the active agent. The particles can be microparticle(s) and/or nanoparticle(s). The particles can include one or more polymers. One or more of the polymers can be a synthetic polymer. The particle or particles can be formed by, for example, single emulsion technique or double emulsion technique or nanoprecipitation.

The delivery vehicles can be nanoscale compositions, for example, 0.5 nm up to, but not including, about 1 micron. In some embodiments, and for some uses, the particles can be smaller, or larger. Thus, the particles can be microparticles, supraparticles, etc. For example, particle compositions can be between about 1 micron to about 1000 microns. Such compositions can be referred to as microparticulate compositions.

Nanoparticles generally refers to particles in the range of less than 0.5 nm up to, but not including, 1,000 nm. In some embodiments, the nanoparticles have a diameter between 500 nm to less than 0.5 nm, or between 50 and 500 nm, or between 50 and 300 nm. Cellular internalization of polymeric particles can highly dependent upon their size, with nanoparticulate polymeric particles being internalized by cells with much higher efficiency than micoparticulate polymeric particles. For example, Desai, et al. have demonstrated that about 2.5 times more nanoparticles that are 100 nm in diameter are taken up by cultured Caco-2 cells as compared to microparticles having a diameter on 1 μM (Desai, et al., *Pharm. Res.,* 14:1568-73 (1997)). Nanoparticles also have a greater ability to diffuse deeper into tissues in vivo.

In some embodiments, particularly those in which the particles need not be internalized by cells, the particles can be microparticles. Microparticle generally refers to a particle having a diameter, from about 1 micron to about 100 microns. The particles can also be from about 1 to about 50 microns, or from about 1 to about 30 microns, or from about 1 micron to about 10 microns. The microparticles can have any shape. Microparticles having a spherical shape may be referred to as "microspheres."

The particles can have a mean particle size. Mean particle size generally refers to the statistical mean particle size (diameter) of the particles in the composition. Two populations can be said to have a substantially equivalent mean particle size when the statistical mean particle size of the first population of particles is within 20% of the statistical mean particle size of the second population of particles; more preferably within 15%, most preferably within 10%.

The weight average molecular weight can vary for a given polymer but is generally from about 1000 Daltons to 1,000,000 Daltons, 1000 Daltons to 500,000 Dalton, 1000 Daltons to 250,000 Daltons, 1000 Daltons to 100,000 Daltons, 5,000 Daltons to 100,000 Daltons, 5,000 Daltons to 75,000 Daltons, 5,000 Daltons to 50,000 Daltons, or 5,000 Daltons to 25,000 Daltons.

A. Polymer

Particles are can be formed of one or more polymers. Exemplary polymers are discussed below. Copolymers such as random, block, or graft copolymers, or blends of the polymers listed below can also be used.

Functional groups on the polymer can be capped to alter the properties of the polymer and/or modify (e.g., decrease or increase) the reactivity of the functional group. For example, the carboxyl termini of carboxylic acid contain polymers, such as lactide- and glycolide-containing polymers, may optionally be capped, e.g., by esterification, and the hydroxyl termini may optionally be capped, e.g. by etherification or esterification.

Copolymers of PEG or derivatives thereof with any of the polymers described below may be used to make the polymeric particles. In certain embodiments, the PEG or derivatives may be located in the interior positions of the copolymer. Alternatively, the PEG or derivatives may locate near or at the terminal positions of the copolymer. For example, one or more of the polymers above can be terminated with a block of polyethylene glycol. In some embodiments, the core polymer is a blend of pegylated polymer and non-pegylated polymer, wherein the base polymer is the same (e.g., PLGA and PLGA-PEG) or different (e.g., PLGA-PEG and PLA). In certain embodiments, the microparticles or nanoparticles are formed under conditions that allow regions of PEG to phase separate or otherwise locate to the surface of the particles. The surface-localized PEG regions alone may perform the function of, or include, the surface-altering agent.

In particular embodiments, the particles are prepared from one or more polymers terminated with blocks of polyethylene glycol as the surface-altering material.

Release

In certain embodiments, the particles in amniotic space release therapeutic agents over at least 3 days, 5 days, 1 week, 2 weeks, 3 weeks, 1 month, 2 months, 3 months, or longer.

Surface Charge

In certain embodiments, the particles possess a $\zeta$-potential of between about 50 mV and about −50 mV, between about 30 mV and about −30 mV, or between about 10 mV and about −10 mV.

Some charges on the surface of the particles may facilitate binding with the MMC defect in amniotic space or binding to nucleic acids. Thus, the charge of the particles can be selected based on the active agent to be delivered, the disease to be treated, or a combination thereof.

In some embodiments, it may be desirable for the particles to have a negative charge, for example when delivering proteins such as growth factors. Thus, some or all of the polymers forming the particle can have a terminal moiety that imparts a negative charge to the particle. In some embodiments, the negatively charged moiety is a chemical modification to the polymer itself that imparts a negative charge to the polymer. In some embodiments, the negatively charge moiety is a separate, negatively-charged component that is conjugated to the polymer.

The terminal moiety that imparts a negative charge to the particles can be an acidic group or an anionic group. Examples of acidic groups include, but are not limited to, carboxylic acids, protonated sulfates, protonated sulfonates, protonated phosphates, singly- or doubly protonated phosphonates, and singly- or doubly protonated hydroxamates. The corresponding salts of these acidic groups form anionic groups such as carboxylates, sulfates, sulfonates, singly- or doubly deprotonated phosphates, singly- or doubly deprotonated phosphonates, and hydroxamates.

In some embodiments, the particles may be used as nucleic acid carriers. In these embodiments, the particles can be formed of one or more cationic polymers which complex with one or more nucleic acids which are negatively charged.

The cationic polymer can be any synthetic or natural polymer bearing at least two positive charges per molecule and having sufficient charge density and molecular size to bind to nucleic acid under physiological conditions (i.e., pH and salt conditions encountered within the body or within cells). In certain embodiments, the polycationic polymer contains one or more amine residues.

Suitable cationic polymers include, for example, polyethylene imine (PEI), polyallylamine, polyvinylamine, polyvinylpyridine, aminoacetalized poly(vinyl alcohol), acrylic or methacrylic polymers (for example, poly(N,N-dimethylaminoethylmethacrylate)) bearing one or more amine residues, polyamino acids such as polyornithine, polyarginine, and polylysine, protamine, cationic polysaccharides such as chitosan, DEAE-cellulose, and DEAE-dextran, and polyamidoamine dendrimers (cationic dendrimer), as well as copolymers and blends thereof. In some embodiments, the polycationic polymer is poly(amine-co-ester), poly(amine-co-amide) polymer, or poly(amine-co-ester-co-ortho ester).

Cationic polymers can be either linear or branched, can be either homopolymers or copolymers, and when containing amino acids can have either L or D configuration, and can have any mixture of these features. Preferably, the cationic polymer molecule is sufficiently flexible to allow it to form a compact complex with one or more nucleic acid molecules.

In some embodiments, the cationic polymer has a molecular weight of between about 5,000 Daltons and about 100,000 Daltons, more preferably between about 5,000 and about 50,000 Daltons, most preferably between about 10,000 and about 35,000 Daltons.

In particular embodiments, the particles include a hydrophobic polymer, poly(amine-co-ester), poly(amine-co-amide) polymer, or poly(amine-co-ester-co-ortho ester), and optionally, but a shell of, for example, PEG. The core-shell particles can be formed by a co-block polymer. Exemplary polymers are provided below.

1. Exemplary Polymers Hydrophobic Polymers

The polymer that forms the core of the particle may be any biodegradable or non-biodegradable synthetic or natural polymer. In a preferred embodiment, the polymer is a biodegradable polymer.

Particles are ideal materials for the fabrication of gene editing delivery vehicles: 1) control over the size range of fabrication, down to 100 nm or less, an important feature for passing through biological barriers; 2) reproducible biodegradability without the addition of enzymes or cofactors; 3) capability for sustained release of encapsulated, protected nucleic acids over a period in the range of days to months by varying factors such as the monomer ratios or polymer size, for example, the ratio of lactide to glycolide monomer units in poly(lactide-co-glycolide) (PLGA); 4) well-understood fabrication methodologies that offer flexibility over the range of parameters that can be used for fabrication, including choices of the polymer material, solvent, stabilizer, and scale of production; and 5) control over surface properties facilitating the introduction of modular functionalities into the surface.

Any number of biocompatible polymers can be used to prepare the particles. In one embodiment, the biocompatible polymer(s) is biodegradable. In another embodiment, the particles are non-degradable. In other embodiments, the particles are a mixture of degradable and non-degradable particles.

Examples of preferred biodegradable polymers include synthetic polymers that degrade by hydrolysis such as poly(hydroxy acids), such as polymers and copolymers of lactic acid and glycolic acid, other degradable polyesters, polyanhydrides, poly(ortho)esters, polyesters, polyurethanes, poly(butic acid), poly(valeric acid), poly(caprolactone), poly(hydroxyalkanoates), poly(lactide-co-caprolactone), and poly(amine-co-ester) polymers, such as those described in Zhou, et al., *Nature Materials*, 11(1):82-90 (2011), Tietjen, et al. *Nature Communications*, 8:191 (2017) doi:10.1038/s41467-017-00297-x, and WO 2013/082529, U.S. Published Application No. 2014/0342003, and PCT/US2015/061375.

Preferred natural polymers include alginate and other polysaccharides, collagen, albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion.

Exemplary polymers include, but are not limited to, cyclodextrin-containing polymers, in particular cationic cyclodextrin-containing polymers, such as those described in U.S. Pat. No. 6,509,323, In some embodiments, non-biodegradable polymers can be used, especially hydrophobic polymers. Examples of preferred non-biodegradable polymers include ethylene vinyl acetate, poly(meth)acrylic acid, copolymers of maleic anhydride with other unsaturated polymerizable monomers, poly(butadiene maleic anhydride), polyamides, copolymers and mixtures thereof, and dextran, cellulose and derivatives thereof.

Other suitable biodegradable and non-biodegradable polymers include, but are not limited to, polyanhydrides, polyamides, polycarbonates, polyalkylenes, polyalkylenes such as polyethylene and polypropylene, polyalkylene glycols such as poly(ethylene glycol) (PEG), polyalkylene oxides (PEO), polyalkylene terephthalates such as poly (ethylene terephthalate) and ethylene vinyl acetate polymer (EVA), polyvinyl alcohols, polyvinyl ethers, polyvinyl esters such as poly(vinyl acetate), polyethylene, polypropylene, poly(vinyl acetate), poly vinyl chloride, polystyrene, polyvinyl halides such as poly(vinyl chloride) (PVC), polyvinylpyrrolidone, polysiloxanes, polyvinylpyrrolidone, polymers of acrylic and methacrylic esters, polysiloxanes, polyurethanes and copolymers thereof, modified celluloses, alkyl cellulose, hydroxyalkyl celluloses, cellulose ethers, cellulose esters, nitro celluloses, hydroxypropylcellulose, cellulose acetate, cellulose propionate, cellulose acetate butyrate, cellulose acetate phthalate, carboxyethyl cellulose, cellulose triacetate, cellulose sulfate sodium salt, and polyacrylates such as poly(methyl methacrylate), poly(ethylmethacrylate), Poly(2-hydroxyethyl methacrylate) (pHEMA), poly(butylmethacrylate), poly(isobutylmethacrylate), poly(hexylmethacrylate), poly(isodecylmethacrylate), poly(lauryl methacrylate), poly(phenyl methacrylate), poly(methyl acrylate), poly(isopropyl acrylate), poly (isobutyl acrylate), poly(octadecyl acrylate). These materials may be used alone, as physical mixtures (blends), or as co-polymers.

The polymer may be a bioadhesive polymer that is hydrophilic or hydrophobic. Hydrophilic polymers include CARBOPOL™ (a high molecular weight, crosslinked, acrylic acid-based polymers such as those manufactured by NOVEON™), polycarbophil, cellulose esters, and dextran. polymers of acrylic acids, include, but are not limited to, poly(methyl(meth)acrylate) (PMMA), poly(ethyl(meth) acrylate), poly(butyl(meth)acrylate), poly(isobutyl(meth) acrylate), poly(hexyl(meth)acrylate), poly(isodecyl(meth) acrylate), poly(lauryl(meth)acrylate), poly(phenyl(meth) acrylate), poly(methyl acrylate), poly(isopropyl acrylate), poly(isobutyl acrylate), and poly(octadecyl acrylate) (jointly referred to herein as "polyacrylic acids").

Release rate controlling polymers may be included in the polymer matrix or in the coating on the formulation. Examples of rate controlling polymers that may be used are hydroxypropylmethylcellulose (HPMC) with viscosities of either 5, 50, 100 or 4000 cps or blends of the different viscosities, ethylcellulose, methylmethacrylates, such as EUDRAGIT® RS100, EUDRAGIT® RL100, EUDRAGIT® NE 30D (supplied by Rohm America). Gastrosoluble polymers, such as EUDRAGIT® E100 or enteric polymers such as EUDRAGIT® L100-55D, L100 and S100 may be blended with rate controlling polymers to achieve pH dependent release kinetics. Other hydrophilic polymers such as alginate, polyethylene oxide, carboxymethylcellulose, and hydroxyethylcellulose may be used as rate controlling polymers.

These polymers can be obtained from sources such as Sigma Chemical Co., St. Louis, MO; Polysciences, Warrenton, PA; Aldrich, Milwaukee, WI; Fluka, Ronkonkoma, NY; and BioRad, Richmond, CA, or can be synthesized from monomers obtained from these or other suppliers using standard techniques.

In certain embodiments, the hydrophobic polymer is an aliphatic polyester. In preferred embodiments, the hydrophobic polymer is polyhydroxyester such as poly(lactic acid), poly(glycolic acid), or poly(lactic acid-co-glycolic acid).

Other polymers include, but are not limited to, polyalkyl cyanoacralate, polyamino acids such as poly-L-lysine (PLL), poly(valeric acid), and poly-L-glutamic acid, hydroxypropyl methacrylate (HPMA), polyorthoesters, poly (ester amides), poly(ester ethers), polydioxanone and its copolymers, polyhydroxyalkanoates, polypropylene fumarate, polyoxymethylene, poly(butyric acid), trimethylene carbonate, and polyphosphazenes.

The particles can be designed to release molecules to be encapsulated or attached over a period of days to weeks. Factors that affect the duration of release include pH of the surrounding medium (higher rate of release at pH 5 and below due to acid catalyzed hydrolysis of PLGA) and polymer composition. Aliphatic polyesters differ in hydrophobicity and that in turn affects the degradation rate. The hydrophobic poly(lactic acid) (PLA), more hydrophilic poly (glycolic acid) PGA and their copolymers, poly(lactide-co-glycolide) (PLGA) have different release rates. The degradation rate of these polymers, and often the corresponding drug release rate, can vary from days (PGA) to months (PLA) and is easily manipulated by varying the ratio of PLA to PGA.

In some preferred embodiments, the particles can contain one more of the following polyesters: homopolymers including glycolic acid units, referred to herein as "PGA", and lactic acid units, such as poly-L-lactic acid, poly-D-lactic acid, poly-D,L-lactic acid, poly-L-lactide, poly-D-lactide, and poly-D,L-lactide, collectively referred to herein as "PLA", and caprolactone units, such as poly(8-caprolactone), collectively referred to herein as "PCL"; and copolymers including lactic acid and glycolic acid units, such as various forms of poly(lactic acid-co-glycolic acid) and poly (lactide-co-glycolide) characterized by the ratio of lactic acid:glycolic acid, collectively referred to herein as "PLGA"; and polyacrylates, and derivatives thereof. Exemplary polymers also include copolymers of polyethylene glycol (PEG) and the aforementioned polyesters, such as various forms of PLGA-PEG or PLA-PEG copolymers, collectively referred to herein as "PEGylated polymers". In certain embodiments, the PEG region can be covalently associated with polymer to yield "PEGylated polymers" by a cleavable linker. For example, particles can also contain one or more polymer conjugates containing end-to-end linkages between the polymer and a targeting moiety or a detectable label. For example, a modified polymer can be a PLGA-PEG-peptide block polymer.

The in vivo stability/release of the particles can be adjusted during the production by using polymers such as poly(lactide-co-glycolide) copolymerized with polyethylene glycol (PEG). If PEG is exposed on the external surface, it may increase the time these materials circulate due to the hydrophilicity of PEG.

A shell can also be formed of or contain a hyperbranched polymer (HP) with hydroxyl groups, such as a hyperbranched polyglycerol (HPG), hyperbranched peptides (HPP), hyperbranched oligonucleotides (HON), hyperbranched polysaccharides (HPS), and hyperbranched polyunsaturated or saturated fatty acids (HPF). The HP can be covalently bound to the one or more materials that form the core such that the hydrophilic HP is oriented towards the outside of the particles and the hydrophobic material oriented to form the core.

The HP coating can be modified to adjust the properties of the particles. For example, unmodified HP coatings impart stealth properties to the particles which resist non-specific protein absorption and are referred to as nonbioadhesive nanoparticles (NNPs). Alternatively, the hydroxyl groups on the HP coating can be chemically modified to form functional groups that react with functional groups on tissue or otherwise interact with tissue to adhere the particles to the tissue, cells, or extracellular materials, such as proteins. Such functional groups include, but are not limited to, aldehydes, amines, and O-substituted oximes. Particles with an HP coating chemically modified to form functional groups are referred to as bioadhesive nanoparticles (BNPs). The chemically modified HP coating of BNPs forms a bioadhesive corona of the particle surrounding the hydrophobic material forming the core. See, for example, WO 2015/172149, WO 2015/172153, WO 2016/183209, and U.S. Published Applications 2017/0000737 and 2017/0266119.

Particles can be formed of polymers fabricated from polylactides (PLA) and copolymers of lactide and glycolide (PLGA). These have established commercial use in humans and have a long safety record (Jiang, et al., *Adv. Drug Deliv. Rev.*, 57(3):391-410); Aguado and Lambert, *Immunobiology*, 184(2-3):113-25 (1992); Bramwell, et al., *Adv. Drug Deliv. Rev.*, 57(9):1247-65 (2005)). These polymers have been used to encapsulate siRNA (Yuan, et al., *Jour. Nanosocience and Nanotechnology*, 6:2821-8 (2006); Braden, et al., *Jour. Biomed. Nanotechnology*, 3:148-59 (2007); Khan, et al., *Jour. Drug Target*, 12:393-404 (2004); Woodrow, et al., *Nature Materials*, 8:526-533 (2009)). Murata, et al., *J. Control. Release*, 126(3):246-54 (2008) showed inhibition of tumor growth after intratumoral injection of PLGA microspheres encapsulating siRNA targeted against vascular endothelial growth factor (VEGF). However, these microspheres were too large to be endocytosed (35-45 µm) (Conner and Schmid, *Nature*, 422(6927):37-44 (2003)) and required release of the anti-VEGF siRNA extracellularly as a polyplex with either polyarginine or PEI before they could be internalized by the cell. These microparticles may have limited applications because of the toxicity of the polycations and the size of the particles. Nanoparticles (100-300 nm) of PLGA can penetrate deep into tissue and are easily internalized by many cells (Conner and Schmid, *Nature*, 422(6927):37-44 (2003)).

Exemplary particles are described in U.S. Pat. Nos. 4,883, 666, 5,114,719, 5,601,835, 7,534,448, 7,534,449, 7,550,154, and 8,889,117, and U.S. Published Application Nos. 2009/ 0269397, 2009/0239789, 2010/0151436, 2011/0008451, 2011/0268810, 2014/0342003, 2015/0118311, 2015/ 0125384, 2015/0073041, Hubbell, et al., *Science*, 337:303-305 (2012), Cheng, et al., *Biomaterials*, 32:6194-6203 (2011), Rodriguez, et al., *Science*, 339:971-975 (2013), Hrkach, et al., *Sci Transl Med.*, 4:128ra139 (2012), McNeer, et al., *Mol Ther.*, 19:172-180 (2011), McNeer, et al., *Gene Ther.*, 20:658-659 (2013), Babar, et al., *Proc Natl Acad Sci USA*, 109:E1695-E1704 (2012), Fields, et al., *J Control Release* 164:41-48 (2012), and Fields, et al., *Advanced Healthcare Materials*, 361-366 (2015).

2. Poly(Amine-Co-Esters), Poly(Amine-Co-Amides), and Poly(Amine-Co-Ester-Co-Ortho Esters)

The core of the particles can be formed of or contain one or more poly(amine-co-ester), poly(amine-co-amide), poly (amine-co-ester-co-ortho ester) or a combination thereof. In some embodiments, the particles are polyplexes. In some embodiments, the content of a hydrophobic monomer in the polymer is increased relative the content of the same hydrophobic monomer when used to form polyplexes. Increasing the content of a hydrophobic monomer in the polymer forms a polymer that can form solid core particles in the presence of nucleic acids. Unlike polyplexes, these particles are stable for long periods of time during incubation in buffered water, or serum, or upon administration (e.g., injection) into animals. They also provide for a sustained release of nucleic acids which leads to long term activity. In some aspects, the molecular weight of the polymer is less than 5 kDa, 7.5 kDa, 10 kDa, 20 kDa, or 25 kDa. In some forms the molecular weight of the polymer is between about 1 kDa and about 25 kDa, between about 1 kDa and about 10 kDa, between about 1 kDa and about 7.5 kDa.

The polymers can have the general formula:

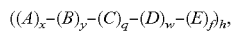

wherein A, B, C, D, and E independently include monomeric units derived from lactones (such as pentadecalactone), a polyfunctional molecule (such as N-methyldiethanolamine), a diacid or diester (such as diethylsebacate), an ortho ester, or polyalkylene oxide (such as polyethylene glycol). In some aspects, the polymers include at least a lactone, a polyfunctional molecule, and a diacid or diester monomeric units. In some aspects, the polymers include at least a lactone, a polyfunctional molecule, an ortho ester, and a diacid or diester monomeric units. In general, the polyfunctional molecule contains one or more cations, one or more positively ionizable atoms, or combinations thereof. The one or more cations are formed from the protonation of a basic nitrogen atom, or from quaternary nitrogen atoms.

In general, x, y, q, w, and f are independently integers from 0-1000, with the proviso that the sum $(x+y+q+w+f)$ is greater than one. h is an integer from 1 to 1000.

In some forms, the percent composition of the lactone can be between about 30% and about 100%, calculated as the mole percentage of lactone unit vs. (lactone unit+diester/ diacid). Expressed in terms of molar ratio, the lactone unit vs. (lactone unit+diester/diacid) content is between about 0.3 and about 1. Preferably, the number of carbon atoms in the lactone unit is between about 10 and about 24. In some embodiments, the number of carbon atoms in the lactone unit is between about 12 and about 16. In some embodiments, the number of carbon atoms in the lactone unit is 12 (dodecalactone), 15 (pentadecalactone), or 16 (hexadecalactone).

The molecular weight of the lactone unit in the polymer, the lactone unit's content of the polymer, or both, influences the formation of solid core particles.

Suitable polymers as well as particles and polyplexes formed therefrom are disclosed in WO 2013/082529, WO 2016/183217, U.S. Published Application No. 2016/ 0251477, U.S. Published Application No. 2015/0073041, U.S. Published Application No. 2014/0073041, and U.S. Pat. No. 9,272,043, each of which is specifically incorporated by reference in entirety.

For example, in some embodiments, the polymer includes a structure that has the formula:

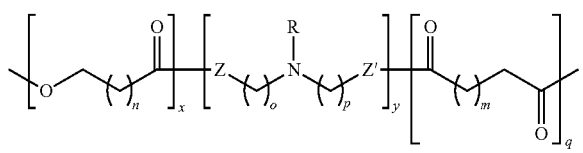

Formula I wherein n is an integer from 1-30, m, o, and p are independently an integer from 1-20, x, y, and q are independently integers from 1-1000, Z and Z' are independently O or NR', wherein R and R' are independently hydrogen, substituted or unsubstituted alkyl, or substituted or unsubstituted aryl. Examples of R and R' groups include, but are not limited to, hydrogen, methyl, ethyl, n-propyl, isopropyl, n-butyl, t-butyl, isobutyl, see-butyl, cyclohexyl, (cyclohexyl)methyl, cyclopropylmethyl, and homologs and isomers of, for example, n-pentyl, n-hexyl, n-heptyl, n-octyl, phenyl, naphthalyl, anthracenyl, phenanthryl, chrysenyl, pyrenyl, tolyl, xylyl, etc. In particular embodiments, the values of x, y, and q are such that the weight average molecular weight of the polymer is greater than 5,000 Daltons. In some aspects, the molecular weight of the polymer is less than 5 kDa, 7.5 kDa, 10 kDa, 20 kDa, or 25 kDa. In some forms the molecular weight of the polymer is between about 1 kDa and about 25 kDa, between about 1 kDa and about 10 kDa, between about 1 kDa and about 7.5 kDa. The polymer can be prepared from one or more lactones, one or more amine-diols, triamines, or hydroxy diamines, and one or more diacids or diesters. In those embodiments where two or more different lactone, diacid or diester, and/or triamine, amine-diol, or hydroxy diamine monomers are used, the values of n, o, p, and/or m can be the same or different.

In some forms, the percent composition of the lactone unit is between about 30% and about 100%, calculated lactone unit vs. (lactone unit+diester/diacid). Expressed in terms of a molar ratio, the lactone unit vs. (lactone unit+diester/ diacid) content is between about 0.3 and about 1, i.e., $x/(x+q)$ is between about 0.3 and about 1. Preferably, the number of carbon atoms in the lactone unit is between about 10 and about 24, more preferably the number of carbon atoms in the lactone unit is between about 12 and about 16. Most preferably, the number of carbon atoms in the lactone unit is 12 (dodecalactone), 15 (pentadecalactone), or 16 (hexadecalactone).

In some embodiments, Z and Z' are O. In some embodiments, Z is O and Z' is NR', or Z is NR' and Z' is O, wherein R' is hydrogen, substituted or unsubstituted alkyl, or substituted or unsubstituted aryl. Examples of R' include, but are not limited to, hydrogen, methyl, ethyl, n-propyl, isopropyl, n-butyl, t-butyl, isobutyl, see-butyl, cyclohexyl, (cyclohexyl)methyl, cyclopropylmethyl, and homologs and isomers of, for example, n-pentyl, n-hexyl, n-heptyl, n-octyl, phenyl, naphthalyl, anthracenyl, phenanthryl, chrysenyl, pyrenyl, tolyl, xylyl, etc.

In some embodiments, Z and Z' are O and n is an integer from 1-24, such 4, 10, 13, or 14.

In some embodiments, Z and Z' are O, n is an integer from 1-24, such 4, 10, 13, or 14, and m is an integer from 1-10, such as 4, 5, 6, 7, or 8.

In some embodiments, Z and Z' are O, n is an integer from 1-24, such 4, 10, 13, or 14, m is an integer from 1-10, such as 4, 5, 6, 7, or 8, and o and p are the same integer from 1-6, such 2, 3, or 4.

In some embodiments, Z and Z' are O, n is an integer from 1-24, such 4, 10, 13, or 14, m is an integer from 1-10, such as 4, 5, 6, 7, or 8, and R is alkyl, such as methyl, ethyl, n-propyl, isopropyl, n-butyl, t-butyl, isobutyl, see-butyl, cyclohexyl, (cyclohexyl)methyl, cyclopropylmethyl, and homologs and isomers of, for example, n-pentyl, n-hexyl, n-heptyl, n-octyl, or aryl, such as phenyl, naphthalyl, anthracenyl, phenanthryl, chrysenyl, pyrenyl, tolyl, or xylyl.

In certain embodiments, n is 14 (e.g., pentadecalactone, PDL), m is 7 (e.g., diethylsebacate, DES), o and p are 2 (e.g., N-methyldiethanolamine, MDEA). In certain embodiments, n, m, o, and p are as defined above, and PEG is incorporated as a monomer.

In particular embodiments, the values of x, y, and q are such that the weight average molecular weight of the polymer is greater than 5,000 Daltons.

The polymer can be prepared from one or more substituted or unsubstituted lactones, one or more substituted or unsubstituted amine-diols (Z and Z'=O), triamines (Z and Z'=NR'), or hydroxy-diamines (Z=O, and Z'=NR', or vice versa) and one or more substituted or unsubstituted diacids or diesters. In those embodiments where two or more different lactone, diacid or diester, and/or triamine, amine-diol, or hydroxy diamine monomers are used, than the values of n, o, p, and/or m can be the same or different.

The monomer units can be substituted at one or more positions with one or more substituents. Exemplary substituents include, but are not limited to, alkyl groups, cyclic alkyl groups, alkene groups, cyclic alkene groups, alkynes, halogen, hydroxyl, carbonyl (such as a carboxyl, alkoxycarbonyl, formyl, or an acyl), thiocarbonyl (such as a thioester, a thioacetate, or a thioformate), alkoxyl, phosphoryl, phosphate, phosphonate, phosphinate, amino, amido, amidine, imine, cyano, nitro, azido, sulfhydryl, alkylthio, sulfate, sulfonate, sulfamoyl, sulfonamido, sulfonyl, nitro, heterocyclyl, aralkyl, or an aromatic or heteroaromatic moiety.

The polymer is preferably biocompatible. Readily available lactones of various ring sizes are known to possess low toxicity: for example, polyesters prepared from small lactones, such as poly(caprolactone) and poly(p-dioxanone) are commercially available biomaterials which have been used in clinical applications. Large (e.g., $C_{16}$-$C_{24}$) lactones and their polyester derivatives are natural products that have been identified in living organisms, such as bees. Lactones containing ring carbon atoms between 16 and 24 are specifically contemplated and disclosed.

In other embodiments, the polymer is biocompatible and biodegradable. The nucleic acid(s) encapsulated by and/or associated with the particles can be released through different mechanisms, including diffusion and degradation of the polymeric matrix. The rate of release can be controlled by varying the monomer composition of the polymer and thus the rate of degradation. For example, if simple hydrolysis is the primary mechanism of degradation, increasing the hydrophobicity of the polymer may slow the rate of degradation and therefore increase the time period of release. In all case, the polymer composition is selected such that an effective amount of nucleic acid(s) is released to achieve the desired purpose/outcome.

The polymers can further include one or more blocks of an alkylene oxide, such as polyethylene oxide, polypropylene oxide, and/or polyethylene oxide-co-polypropylene oxide. The structure of a PEG-containing polymer is shown below:

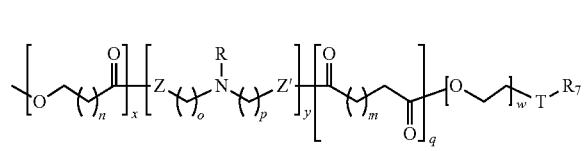

wherein n is an integer from 1-30, m, o, and p are independently an integer from 1-20, x, y, q, and w are independently integers from 1-1000, Z and Z' are independently O or NR', wherein R and R' are independently hydrogen, substituted or unsubstituted alkyl, or substituted or unsubstituted aryl, wherein T is oxygen or is absent, and wherein $R_7$ is hydrogen, alkyl, substituted alkyl, aryl, substituted alkyl, cycloalkyl, substituted cycloalkyl, maleimide, amine, thiol, N-hydroxysuccinimide ester, azide, acrylate, methacrylate, alkyne, hydroxide, or isocynate. In particular embodiments, the values of x, y, q, and w are such that the weight average molecular weight of the polymer is greater than 5,000 Daltons. In some aspects, the molecular weight of the polymer is less than 5 kDa, 7.5 kDa, 10 kDa, 20 kDa, or 25 kDa. In some forms the molecular weight of the polymer is between about 1 kDa and about 25 kDa, between about 1 kDa and about 10 kDa, between about 1 kDa and about 7.5 kDa. Examples of R and R' groups include, but are not limited to, hydrogen, methyl, ethyl, n-propyl, isopropyl, n-butyl, t-butyl, isobutyl, see-butyl, cyclohexyl, (cyclohexyl)methyl, cyclopropylmethyl, and homologs and isomers of, for example, n-pentyl, n-hexyl, n-heptyl, n-octyl, phenyl, naphthalyl, anthracenyl, phenanthryl, chrysenyl, pyrenyl, tolyl, xylyl, etc.

The structure of a PEG-containing copolymer is shown below:

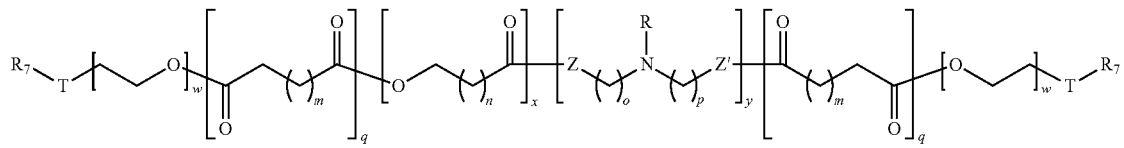

wherein n is an integer from 1-30, m, o, and p are independently an integer from 1-20, x, y, q, and w are independently integers from 1-1000, Z and Z' are independently O or NR', wherein R and R' are independently hydrogen, substituted or unsubstituted alkyl, or substituted or unsubstituted aryl, wherein T is oxygen or is absent, and wherein $R_7$ is hydrogen, alkyl, substituted alkyl, aryl, substituted alkyl, cycloalkyl, substituted cycloalkyl, maleimide, amine, thiol, N-hydroxysuccinimide ester, azide, acrylate, methacrylate, alkyne, hydroxide, or isocynate.

In particular embodiments, the values of x, y, q, and w are such that the weight average molecular weight of the polymer is greater than 5,000 Daltons. In some aspects, the molecular weight of the polymer is less than 5 kDa, 7.5 kDa, 10 kDa, 20 kDa, or 25 kDa. In some forms the molecular weight of the polymer is between about 1 kDa and about 25 kDa, between about 1 kDa and about 10 kDa, between about 1 kDa and about 7.5 kDa. Examples of R and R' groups include, but are not limited to, hydrogen, methyl, ethyl, n-propyl, isopropyl, n-butyl, t-butyl, isobutyl, see-butyl, cyclohexyl, (cyclohexyl)methyl, cyclopropylmethyl, and homologs and isomers of, for example, n-pentyl, n-hexyl, n-heptyl, n-octyl, phenyl, naphthalyl, anthracenyl, phenanthryl, chrysenyl, pyrenyl, tolyl, xylyl, etc.

The blocks of polyalkylene oxide can located at the termini of the polymer (i.e., by reacting PEG having one hydroxy group blocked, for example, with a methoxy group), within the polymer backbone (i.e., neither of the hydroxyl groups are blocked), or combinations thereof.

In particular embodiments, the synthetic polymer includes polymers or copolymers of lactic acid, glycolic acid, degradable polyesters, polyanhydrides, poly(ortho)esters, polyesters, polyurethanes, poly(butic acid), poly(valeric acid), poly(caprolactone), poly(hydroxyalkanoates), poly(lactide-co-caprolactone), poly(amine-co-ester) polymers, or a combination of any two or more of the foregoing. In specific embodiments, the particles are nanoparticles formed of PLGA poly(lactic-co-glycolic acid) (PLGA), a blend of PLGA and poly(beta-amino) esters (PBAEs) (e.g., about 5 and about 25 percent PBAE (wt %)), or poly(amine-co-ester) (PACE). In some embodiments, these particles are utilized for intracellular delivery of gene editing compositions such as peptide nucleic acids alone or in combination with donor oligonucleotides.

In other particular embodiments, the particles are formed of hydrogel type materials such as alginate, chitosan, poly(HEMA) and other acrylate polymers and copolymers. In specific embodiments, the particles are microparticles formed of alginate. In some embodiments, these particles are utilized for extracellular delivery (e.g., paracrine delivery) of a growth factor such a FGF.

B. Polycations In some embodiments, the nucleic acids are complexed to polycations to increase the encapsulation efficiency of the nucleic acids into the particles. The term "polycation" refers to a compound having a positive charge, preferably at least 2 positive charges, at a selected pH, preferably physiological pH. Polycationic moieties have between about 2 to about 15 positive charges, preferably between about 2 to about 12 positive charges, and more preferably between about 2 to about 8 positive charges at selected pH values.

Many polycations are known in the art. Suitable constituents of polycations include basic amino acids and their derivatives such as arginine, asparagine, glutamine, lysine and histidine; cationic dendrimers; and amino polysaccharides. Suitable polycations can be linear, such as linear tetralysine, branched or dendrimeric in structure.

Exemplary polycations include, but are not limited to, synthetic polycations based on acrylamide and 2-acrylamido-2-methylpropanetrimethylamine, poly(N-ethyl-4-vinylpyridine) or similar quartemized polypyridine, diethylaminoethyl polymers and dextran conjugates, polymyxin B sulfate, lipopolyamines, poly(allylamines) such as the strong polycation poly(dimethyldiallylammonium chloride), polyethyleneimine, polybrene, and polypeptides such as protamine, the histone polypeptides, polylysine, polyarginine and polyornithine.

In one embodiment, the polycation is a polyamine. Polyamines are compounds having two or more primary amine groups. In a preferred embodiment, the polyamine is a naturally occurring polyamine that is produced in prokaryotic or eukaryotic cells. Naturally occurring polyamines represent compounds with cations that are found at regularly-spaced intervals and are therefore particularly suitable for complexing with nucleic acids. Polyamines play a major role in very basic genetic processes such as DNA synthesis and gene expression. Polyamines are integral to cell migration, proliferation and differentiation in plants and animals. The metabolic levels of polyamines and amino acid precursors are critical and hence biosynthesis and degradation are tightly regulated. Suitable naturally occurring polyamines include, but are not limited to, spermine, spermidine, cadaverine and putrescine. In a preferred embodiment, the polyamine is spermidine.

In another embodiment, the polycation is a cyclic polyamine. Cyclic polyamines are known in the art and are described, for example, in U.S. Pat. No. 5,698,546, WO 1993/012096 and WO 2002/010142. Exemplary cyclic polyamines include, but are not limited to, cyclen.

Spermine and spermidine are derivatives of putrescine (1,4-diaminobutane), which is produced from L-ornithine by action of ODC (ornithine decarboxylase). L-ornithine is the product of L-arginine degradation by arginase. Spermidine is a triamine structure that is produced by spermidine synthase (SpdS) which catalyzes monoalkylation of putrescine (1,4-diaminobutane) with decarboxylated S-adenosylmethionine (dcAdoMet) 3-aminopropyl donor. The formal alkylation of both amino groups of putrescine with the 3-aminopropyl donor yields the symmetrical tetraamine spermine. The biosynthesis of spermine proceeds to spermidine by the effect of spermine synthase (SpmS) in the presence of dcAdoMet. The 3-aminopropyl donor (dcAdoMet) is derived from S-adenosylmethionine by sequential transformation of L-methionine by methionine adenosyltransferase followed by decarboxylation by AdoMetDC (S-adenosylmethionine decarboxylase). Hence, putrescine, spermidine and spermine are metabolites derived from the amino acids L-arginine (L-ornithine, putrescine) and L-methionine (dcAdoMet, aminopropyl donor).

In some embodiments, the particles themselves are a polycation (e.g., a blend of PLGA and poly(beta amino ester).

C. Coupling Agents or Ligands

The external surface of the polymeric particles may be modified by conjugating to, or incorporating into, the surface of the particle a coupling agent or ligand.

In a preferred embodiment, the coupling agent is present in high density on the surface of the particle. As used herein, "high density" refers to polymeric particles having a high density of ligands or coupling agents, which is preferably in the range of 1,000 to 10,000,000, more preferably 10,000-1,000,000 ligands per square micron of particle surface area. This can be measured by fluorescence staining of dissolved particles and calibrating this fluorescence to a known amount of free fluorescent molecules in solution.

Coupling agents associate with the polymeric particles and provide substrates that facilitate the modular assembly and disassembly of functional elements to the particles. Coupling agents or ligands may associate with particles through a variety of interactions including, but not limited to, hydrophobic interactions, electrostatic interactions and covalent coupling.

In a preferred embodiment, the coupling agents are molecules that match the polymer phase hydrophile-lipophile balance. Hydrophile-lipophile balances range from 1 to 15. Molecules with a low hydrophile-lipophile balance are more lipid loving and thus tend to make a water in oil emulsion while those with a high hydrophile-lipophile balance are more hydrophilic and tend to make an oil in water emulsion. Fatty acids and lipids have a low hydrophile-lipophile balance below 10.

Any amphiphilic polymer with a hydrophile-lipophile balance in the range 1-10, more preferably between 1 and 6, most preferably between 1 and up to 5, can be used as a coupling agent. Examples of coupling agents which may associate with polymeric particles via hydrophobic interactions include, but are not limited to, fatty acids, hydrophobic or amphipathic peptides or proteins, and polymers. These classes of coupling agents may also be used in any combination or ratio. In a preferred embodiment, the association of adaptor elements with particles facilitates a prolonged presentation of functional elements, which can last for several weeks.

Coupling agents can also be attached to polymeric particles through covalent interactions through various functional groups. Functionality refers to conjugation of a molecule to the surface of the particle via a functional chemical group (carboxylic acids, aldehydes, amines, sulfhydryls and hydroxyls) present on the surface of the particle and present on the molecule to be attached.

Functionality may be introduced into the particles in two ways. The first is during the preparation of the particles, for example during the emulsion preparation of particles by incorporation of stabilizers with functional chemical groups. Suitable stabilizers include hydrophobic or amphipathic molecules that associate with the outer surface of the particles.

A second is post-particle preparation, by direct crosslinking particles and ligands with homo- or heterobifunctional crosslinkers. This second procedure may use a suitable chemistry and a class of crosslinkers (CDI, EDAC, glutaraldehydes, etc. as discussed in more detail below) or any other crosslinker that couples ligands to the particle surface via chemical modification of the particle surface after preparation. This second class also includes a process whereby amphiphilic molecules such as fatty acids, lipids or functional stabilizers may be passively adsorbed and adhered to the particle surface, thereby introducing functional end groups for tethering to ligands.

One useful protocol involves the "activation" of hydroxyl groups on polymer chains with the agent, carbonyldiimidazole (CDI) in aprotic solvents such as DMSO, acetone, or THF. CDI forms an imidazolyl carbamate complex with the hydroxyl group which may be displaced by binding the free amino group of a molecule such as a protein. The reaction is an N-nucleophilic substitution and results in a stable N-alkylcarbamate linkage of the molecule to the polymer. The "coupling" of the molecule to the "activated" polymer matrix is maximal in the pH range of 9-10 and normally requires at least 24 hrs. The resulting molecule-polymer complex is stable and resists hydrolysis for extended periods of time.

Another coupling method involves the use of 1-ethyl-3-(3-dimethylaminopropyl) carbodiimide (EDAC) or "water-soluble CDI" in conjunction with N-hydroxylsulfosuccinimide (sulfo NHS) to couple the exposed carboxylic groups of polymers to the free amino groups of molecules in a totally aqueous environment at the physiological pH of 7.0. Briefly, EDAC and sulfo-NHS form an activated ester with the carboxylic acid groups of the polymer which react with the amine end of a molecule to form a peptide bond. The resulting peptide bond is resistant to hydrolysis. The use of sulfo-NHS in the reaction increases the efficiency of the EDAC coupling by a factor of ten-fold and provides for exceptionally gentle conditions that ensure the viability of the molecule-polymer complex.

By using either of these protocols it is possible to "activate" almost all polymers containing either hydroxyl or carboxyl groups in a suitable solvent system that will not dissolve the polymer matrix.

A useful coupling procedure for attaching molecules with free hydroxyl and carboxyl groups to polymers involves the use of the cross-linking agent, divinylsulfone. This method would be useful for attaching sugars or other hydroxylic compounds with bioadhesive properties to hydroxylic matrices. Briefly, the activation involves the reaction of divinylsulfone to the hydroxyl groups of the polymer, forming the vinylsulfonyl ethyl ether of the polymer. The vinyl groups will couple to alcohols, phenols and even amines. Activation and coupling take place at pH 11. The linkage is stable in the pH range from 1-8 and is suitable for transit through the intestine.

Any suitable coupling method known to those skilled in the art for the coupling of molecules and polymers with double bonds, including the use of UV crosslinking, may be used for attachment of molecules to the polymer.

In one embodiment, coupling agents can be conjugated to affinity tags. Affinity tags are any molecular species which form highly specific, noncovalent, physiochemical interactions with defined binding partners. Affinity tags which form highly specific, noncovalent, physiochemical interactions with one another are defined herein as "complementary". Suitable affinity tag pairs are well known in the art and include epitope/antibody, biotin/avidin, biotin/streptavidin, biotin/neutravidin, glutathione-S-transferase/glutathione, maltose binding protein/amylase and maltose binding protein/maltose. Examples of suitable epitopes which may be used for epitope/antibody binding pairs include, but are not limited to, HA, FLAG, c-Myc, glutatione-S-transferase, $His_6$, GFP, DIG, biotin and avidin. Antibodies (both monoclonal and polyclonal and antigen-binding fragments thereof) which bind to these epitopes are well known in the art.

Affinity tags that are conjugated to coupling agents allow for highly flexible, modular assembly and disassembly of functional elements which are conjugated to affinity tags which form highly specific, noncovalent, physiochemical interactions with complementary affinity tags which are conjugated to coupling agents. Adaptor elements may be conjugated with a single species of affinity tag or with any combination of affinity tag species in any ratio. The ability to vary the number of species of affinity tags and their ratios conjugated to adaptor elements allows for exquisite control over the number of functional elements which may be attached to the particles and their ratios.

In another embodiment, coupling agents are coupled directly to functional elements in the absence of affinity tags, such as through direct covalent interactions. Coupling agents can be covalently coupled to at least one species of functional element. Coupling agents can be covalently coupled to a single species of functional element or with any combination of species of functional elements in any ratio.

In a preferred embodiment, coupling agents are conjugated to at least one affinity tag that provides for assembly and disassembly of modular functional elements which are conjugated to complementary affinity tags. In a more preferred embodiment, coupling agents are fatty acids that are conjugated with at least one affinity tag. In a particularly preferred embodiment, the coupling agents are fatty acids conjugated with avidin or streptavidin. Avidin/streptavidin-conjugated fatty acids allow for the attachment of a wide variety of biotin-conjugated functional elements.

The coupling agents are preferably provided on, or in the surface of, particles at a high density. This high density of coupling agents allows for coupling of the polymeric particles to a variety of species of functional elements while still allowing for the functional elements to be present in high enough numbers to be efficacious.

1. Fatty Acids

The coupling agents may include fatty acids. Fatty acids may be of any acyl chain length and may be saturated or unsaturated. In a particularly preferred embodiment, the fatty acid is palmitic acid. Other suitable fatty acids include, but are not limited to, saturated fatty acids such as butyric, caproic, caprylic, capric, lauric, myristic, stearic, arachidic and behenic acid. Still other suitable fatty acids include, but are not limited to, unsaturated fatty acids such as oleic, linoleic, alpha-linolenic, arachidonic, eicosapentaenoic, docosahexaenoic and erucic acid.

2. Hydrophobic or Amphipathic Peptides

The coupling agents may include hydrophobic or amphipathic peptides. Preferred peptides should be sufficiently hydrophobic to preferentially associate with the polymeric particle over the aqueous environment. Amphipathic polypeptides useful as adaptor elements may be mostly hydrophobic on one end and mostly hydrophilic on the other end. Such amphipathic peptides may associate with polymeric particles through the hydrophobic end of the peptide and be conjugated on the hydrophilic end to a functional group.

3. Hydrophobic Polymers

Coupling agents may include hydrophobic polymers. Examples of hydrophobic polymers include, but are not limited to, polyanhydrides, poly(ortho)esters, and polyesters such as polycaprolactone.

III. Therapeutic, Prophylactic, and Diagnostic Agent

The methods typically include in utero delivery of one or more therapeutic prophylactic, or diagnostic agents. Thus, in some embodiments, the particles have encapsulated therein, dispersed therein, complexed thereto and/or covalently or non-covalently associated with the surface one or more therapeutic prophylactic, or diagnostic agents. The therapeutic prophylactic, or diagnostic agent can be a small molecule, protein, polysaccharide or saccharide, nucleic acid molecule and/or lipid.

A. Growth Factors

In some embodiments, the agent is a growth factor. Growth factors typically act as signaling molecules between cells. Examples are cytokines and hormones that bind to specific receptors on the surface of their target cells. They often promote cell differentiation and maturation, which varies between growth factors. For example, bone morphogenetic proteins stimulate bone cell differentiation, while fibroblast growth factors and vascular endothelial growth factors stimulate blood vessel differentiation. Exemplary growth factors include, but are not limited to, Adrenomedullin (AM), Angiopoietin (Ang), Autocrine motility factor, Bone morphogenetic proteins (BMPs), Ciliary neurotrophic factor family, Ciliary neurotrophic factor (CNTF), Leukemia inhibitory factor (LIF), Interleukin-6 (IL-6), Colony-stimulating factors, Macrophage colony-stimulating factor (m-CSF), Granulocyte colony-stimulating factor (G-CSF), Granulocyte macrophage colony-stimulating factor (GM-CSF), Epidermal growth factor (EGF), Ephrins, Erythropoietin (EPO), Fibroblast growth factors (FGF, and FGF1-23), Foetal Bovine Somatotrophin (FBS), GDNF family of ligands, Glial cell line-derived neurotrophic factor (GDNF), Neurturin, Persephin, Artemin, Growth differentiation factor-9 (GDF9), Hepatocyte growth factor (HGF), Hepatoma-derived growth factor (HDGF), Insulin, Insulin-like growth factors, Insulin-like growth factor-1 (IGF-1), Insulin-like growth factor-2 (IGF-2), Interleukins (e.g., IL-1, 2, 3, 4, 5, 6, 7), Keratinocyte growth factor (KGF), Migration-stimulating factor (MSF), Macrophage-stimulating protein (MSP), also known as hepatocyte growth factor-like protein (HGFLP), Myostatin (GDF-8), Neuregulins (e.g, Neurgeulin 1-4), Neurotrophins, Brain-derived neurotrophic factor (BDNF), Nerve growth factor (NGF), Neurotrophin-3 (NT-3), Neurotrophin-4 (NT-4), Placental growth factor (PGF), Platelet-derived growth factor (PDGF), Renalase (RNLS)—Anti-apoptotic survival factor, T-cell growth factor (TCGF), Thrombopoietin (TPO), Transforming growth factors, Transforming growth factor alpha (TGF-α), Transforming growth factor beta (TGF-β), Tumor necrosis factor-alpha (TNF-α), Vascular endothelial growth factor (VEGF), and Wnt signaling pathway modulators.

Basic Fibroblast Growth Factor (bFGF or FGF2)

In some embodiment, the growth factor is an FGF. The mammalian fibroblast growth factor (FGF) family consists of 22 structurally similar polypeptides that are present in most multicellular organisms and exert diverse biological effects. Members of the FGF family are active in many embryological and adult physiological processes, and FGFs have been shown to play a part in many developmental, neoplastic, metabolic, and neurological diseases. FGFs can work via paracrine, intracrine, and endocrine signaling pathways. One of the prototypical FGFs, FGF2 or "basic FGF" (bFGF), is an 18 kDa polypeptide with 155 amino acids that works primarily by paracrine signaling and plays an important role in all four phases of wound healing: hemostasis; inflammation; proliferation; remodeling. bFGF is a potent mitogen that stimulates the migration, proliferation, and differentiation of cells of mesenchymal and neurectodermal origin, such as keratinocytes, fibroblasts, melanocytes, and endothelial cells. For the purpose of treating fetal MMC, it the ability of bFGF to stimulate growth and proliferation of keratinocytes and fibroblasts, vital participants in new skin formation, that makes it a logical therapeutic candidate.

Studies have proven the ability of bFGF to induce new skin and blood vessel formation in rats and sheep. One group in particular has conducted multiple experiments with gelatin sponges impregnated with human recombinant bFGF in rat and sheep models of MMC. Human bFGF is 97% identical to mouse and rat bFGF, and despite the 3% of difference in amino acid sequence, the successful use of human bFGF in rodents in prior studies indicates that there is sufficient cross-reactivity between human and rat bFGF in vivo. This group showed that new vessel and skin growth occurred in the immediate area where BFGF scaffolds or sponges were applied, which is consistent with bFGF's function as a paracrine signaling molecule. Alginate microparticles have been successfully used for encapsulation and controlled delivery of growth factor protein. The Examples below show that intra-amniotic injection of various biodegradable and biocompatible microparticles is safe for the delivery of fluorescent dyes and nucleotides, and FGF delivered in this manner can be used to treat MMC.

B. Gene Editing

In some embodiments, the active agent is one or more nucleic acids. The nucleic acid can alter, correct, or replace an endogenous nucleic acid sequence. The nucleic acid can be used to, for example, treat cancers, diseases and disorders, and correct defects in genes. Gene therapy is a technique for correcting defective genes responsible for disease development. Researchers may use one of several approaches for correcting faulty genes:

A normal gene may be inserted into a nonspecific location within the genome to replace a nonfunctional gene. This approach is most common.

An abnormal gene can be swapped for a normal gene through homologous recombination.

The abnormal gene can be repaired through selective reverse mutation, which returns the gene to its normal function.

The regulation (the degree to which a gene is turned on or off) of a particular gene could be altered.

The nucleic acid can be a DNA, RNA, a chemically modified nucleic acid, or combinations thereof. Gene editing technologies are discussed in more detail below.

C. Excipient

Excipients may be included in the particle formulations to enhance the stability, solubility, and/or controlled release manner of encapsulated therapeutic agents. An exemplary excipient to stabilize protein agents is human serum albumin. In other forms, trehalose may be used as a stabilizing agent for proteins.

IV. Gene Editing Technology

In some embodiments, the therapeutic, prophylactic or diagnostic agent is, or encodes, a gene editing technology. Gene editing technologies can be used alone or in combination with a potentiating agent and/or other active agents. Exemplary gene editing technologies include, but are not limited to, triplex-forming, pseudocomplementary oligonucleotides, CRISPR/Cas, zinc finger nucleases, and TALENs, each of which are discussed in more detail below. Some gene editing technologies are used in combination with a donor oligonucleotide. In some embodiments, the gene editing technology is the donor oligonucleotide, which can be used alone to modify genes. Strategies include, but are not limited to, small fragment homologous replacement (e.g., polynucleotide small DNA fragments (SDFs)), single-stranded oligodeoxynucleotide-mediated gene modification (e.g., ssODN/SSOs) and other described in Sargent, Oligonucleotides, 21(2): 55-75 (2011)), and elsewhere. Other suitable gene editing technologies include, but are not limited to intron encoded meganucleases that are engineered to change their target specificity. See, e.g., Arnould, et al., *Protein Eng. Des. Sel.*, 24(1-2):27-31 (2011)).

In some embodiments, the gene editing composition does not modify a target sequence within a maternal genome. In some embodiments, the target sequence of the fetal or embryonic genome and the target sequence of maternal genome are identical. In some embodiments they are not identical. The fetal or embryonic genome and the maternal genome can be isolated, derived, or obtained from genetically-related or genetically un-related individuals. The fetal or embryonic genome can include one or more mutations in a coding sequence or a non-coding sequence corresponding to a target gene that either indicates the fetus or embryo is at risk of developing a disease or disorder or that indicates that the fetus has a disease or disorder. The coding sequence or a non-coding sequence corresponding to the target gene can include the target sequence. The coding sequence corresponding to the target gene can include one or more exon(s) encoding a product of the target gene. The non-coding sequence corresponding to the target gene can include one or more transcriptional regulator(s), enhancer(s), superenhancer(s), intron(s), and regulatory RNAs that selectively bind a transcript of the target gene. The one or more transcriptional regulator(s) can include a sequence encoding a promoter. The one or more regulatory RNAs that selectively bind a transcript of the target gene comprise one or more miRNA(s). The mutation can include a substitution, an insertion, a deletion, an indel, an inversion, a frameshift, or a transposition. The mutation can be a transcriptional or translational truncation, altered transcriptional splicing, early termination of transcription or translation, variant transcriptional regulation or variant epigenetic regulation.

In some embodiments, the gene editing composition modifies a target sequence within a genome by reducing or preventing expression of the target sequence. The gene editing composition can induce single-stranded or double-stranded breaks in the target sequence. The gene editing composition can induce formation of a triplex within the target sequence.

Gene editing compositions include CRISPR systems, zinc finger nucleases (ZFN), transcription activator-like effector nucleases (TALEN), small fragment homologous replacement. The gene editing composition can be a triplex forming composition. The gene editing composition can be a pseudo-complementary oligonucleotide or PNA oligomer.

V. Methods of Manufacture

A. Methods of Making Particles

The particle compositions described herein can be prepared by a variety of methods.

1. Exemplary Preferred Methods of Manufacture

In preferred embodiments, the particles are formed by a double-emulsion solvent evaporation technique, such as is disclosed in U.S. Published Application No. 2011/0008451 or U.S. Published Application No. 2011/0268810, each of which is a specifically incorporated by reference in its entirety, or Fahmy, et al., *Biomaterials*, 26:5727-5736, (2005), or McNeer, et al., *Mol. Ther.* 19, 172-180 (2011)). This aqueous solution is then added dropwise to a polymer solution of a desired polymer dissolved in an organic solvent to form the first emulsion.

This mixture is then added dropwise to solution containing a surfactant, such as polyvinyl alcohol (PVA) and sonicated to form the double emulsion. The final emulsion is then poured into a solution containing the surfactant in an aqueous solution and stirred for a period of time to allow the dichloromethane to evaporate and the particles to harden. The concentration of the surfactant used to form the emulsion, and the sonication time and amplitude can been optimized according to principles known in the art for formulating particles with a desired diameter. The particles can be collected by centrifugation. If it is desirable to store the particles for later use, they can be rapidly frozen, and lyophilized.

In preferred embodiments the particles are PLGA particles. In a particular exemplary protocol, nucleic acid (such as PNA, DNA, or PNA-DNA) with or without a polycation (such as spermidine) are dissolved in DNAse/RNAse free $H_2O$. Encapsulant in $H_2O$ can be added dropwise to a polymer solution of 50:50 ester-terminated PLGA dissolved in dichloromethane (DCM), then sonicated to form the first emulsion. This emulsion can then be added dropwise to 5% polyvinyl alcohol, then sonicated to form the second emulsion. This mixture can be poured into 0.3% polyvinyl alcohol, and stirred at room temperature to form particles. Particles can then be collected and washed with, for example $H_2O$, collected by centrifugation, and then resuspended in $H_2O$, frozen at −80° C., and lyophilized. Particles can be stored at −20° C. following lyophilization.

Additional techniques for encapsulating the nucleic acid and polycation complex into polymeric particles are described below.

2. Solvent Evaporation

In this method the polymer is dissolved in a volatile organic solvent, such as methylene chloride. The drug (either soluble or dispersed as fine particles) is added to the solution, and the mixture is suspended in an aqueous solution that contains a surface active agent such as poly(vinyl alcohol). The resulting emulsion is stirred until most of the organic solvent evaporated, leaving solid particles. The resulting particles are washed with water and dried overnight in a lyophilizer. Particles with different sizes (0.5-1000 microns) and morphologies can be obtained by this method. This method is useful for relatively stable polymers like polyesters and polystyrene.

However, labile polymers, such as polyanhydrides, may degrade during the fabrication process due to the presence of water. For these polymers, the following two methods, which can be performed in completely anhydrous organic solvents, are more useful.

3. Interfacial Polycondensation

Interfacial polycondensation is used to microencapsulate a core material in the following manner. One monomer and the core material are dissolved in a solvent. A second monomer is dissolved in a second solvent (typically aqueous) which is immiscible with the first. An emulsion is formed by suspending the first solution through stirring in the second solution. Once the emulsion is stabilized, an initiator is added to the aqueous phase causing interfacial polymerization at the interface of each droplet of emulsion.

4. Solvent Evaporation Microencapsulation

In solvent evaporation microencapsulation, the polymer is typically dissolved in a water immiscible organic solvent and the material to be encapsulated is added to the polymer solution as a suspension or solution in an organic solvent. An emulsion is formed by adding this suspension or solution to a beaker of vigorously stirring water (often containing a surface active agent, for example, polyethylene glycol or polyvinyl alcohol, to stabilize the emulsion). The organic solvent is evaporated while continuing to stir. Evaporation results in precipitation of the polymer, forming solid microcapsules containing core material.

The solvent evaporation process can be used to entrap a liquid core material in a polymer such as PLA, PLA/PGA copolymer, or PLA/PCL copolymer microcapsules. The polymer or copolymer is dissolved in a miscible mixture of solvent and nonsolvent, at a nonsolvent concentration which is immediately below the concentration which would produce phase separation (i.e., cloud point). The liquid core material is added to the solution while agitating to form an emulsion and disperse the material as droplets. Solvent and nonsolvent are vaporized, with the solvent being vaporized at a faster rate, causing the polymer or copolymer to phase separate and migrate towards the surface of the core material droplets. This phase-separated solution is then transferred into an agitated volume of nonsolvent, causing any remaining dissolved polymer or copolymer to precipitate and extracting any residual solvent from the formed membrane. The result is a microcapsule composed of polymer or copolymer shell with a core of liquid material.

Solvent evaporation microencapsulation can result in the stabilization of insoluble active agent particles in a polymeric solution for a period of time ranging from 0.5 hours to several months. Stabilizing an insoluble pigment and polymer within the dispersed phase (typically a volatile organic solvent) can be useful for most methods of microencapsulation that are dependent on a dispersed phase, including film casting, solvent evaporation, solvent removal, spray drying, phase inversion, and many others.

The stabilization of insoluble active agent particles within the polymeric solution could be critical during scale-up. By stabilizing suspended active agent particles within the dispersed phase, the particles can remain homogeneously dispersed throughout the polymeric solution as well as the resulting polymer matrix that forms during the process of microencapsulation.

Solvent evaporation microencapsulation (SEM) have several advantages. SEM allows for the determination of the best polymer-solvent-insoluble particle mixture that will aid in the formation of a homogeneous suspension that can be used to encapsulate the particles. SEM stabilizes the insoluble particles or pigments within the polymeric solution, which will help during scale-up because one will be able to let suspensions of insoluble particles or pigments sit for long periods of time, making the process less time-dependent and less labor intensive. SEM allows for the creation of particles that have a more optimized release of the encapsulated material.

5. Solvent Removal Microencapsulation

In solvent removal microencapsulation, the polymer is typically dissolved in an oil miscible organic solvent and the material to be encapsulated is added to the polymer solution as a suspension or solution in organic solvent. Surface active agents can be added to improve the dispersion of the material to be encapsulated. An emulsion is formed by adding this suspension or solution to vigorously stirring oil, in which the oil is a nonsolvent for the polymer and the polymer/solvent solution is immiscible in the oil. The organic solvent is removed by diffusion into the oil phase while continuing to stir. Solvent removal results in precipitation of the polymer, forming solid microcapsules containing core material.

6. Phase Separation Microencapsulation

In phase separation microencapsulation, the material to be encapsulated is dispersed in a polymer solution with stirring. While continually stirring to uniformly suspend the material, a nonsolvent for the polymer is slowly added to the solution to decrease the polymer's solubility. Depending on the solubility of the polymer in the solvent and nonsolvent, the polymer either precipitates or phase separates into a polymer rich and a polymer poor phase. Under proper conditions, the polymer in the polymer rich phase will migrate to the interface with the continuous phase, encapsulating the core material in a droplet with an outer polymer shell.

7. Spontaneous Emulsification

Spontaneous emulsification involves solidifying emulsified liquid polymer droplets by changing temperature, evaporating solvent, or adding chemical cross-linking agents. The physical and chemical properties of the encapsulant, and the material to be encapsulated, dictates the suitable methods of encapsulation. Factors such as hydrophobicity, molecular weight, chemical stability, and thermal stability affect encapsulation.

8. Coacervation

Encapsulation procedures for various substances using coacervation techniques have been described in the prior art, for example, in GB-B-929 406; GB-B-929 401; U.S. Pat. Nos. 3,266,987; 4,794,000 and 4,460,563. Coacervation is a process involving separation of colloidal solutions into two or more immiscible liquid layers (Ref. Dowben, R. General Physiology, Harper & Row, New York, 1969, pp. 142-143.). Through the process of coacervation compositions comprised of two or more phases and known as coacervates may be produced. The ingredients that comprise the two phase coacervate system are present in both phases; however, the colloid rich phase has a greater concentration of the components than the colloid poor phase.

9. Solvent Removal

This technique is primarily designed for polyanhydrides. In this method, the drug is dispersed or dissolved in a solution of the selected polymer in a volatile organic solvent like methylene chloride. This mixture is suspended by stirring in an organic oil (such as silicon oil) to form an emulsion. Unlike solvent evaporation, this method can be used to make particles from polymers with high melting points and different molecular weights. Particles that range between 1-300 microns can be obtained by this procedure. The external morphology of spheres produced with this technique is highly dependent on the type of polymer used.

10. Spray-Drying

In this method, the polymer is dissolved in organic solvent. A known amount of the active drug is suspended (insoluble drugs) or co-dissolved (soluble drugs) in the polymer solution. The solution or the dispersion is then spray-dried. Typical process parameters for a mini-spray drier (Buchi) are as follows: polymer concentration=0.04 g/mL, inlet temperature=-24° C., outlet temperature=13-15° C., aspirator setting=15, pump setting=10 mL/minute, spray flow=600 Nl/hr, and nozzle diameter=0.5 mm. Particles ranging between 1-10 microns are obtained with a morphology which depends on the type of polymer used.

11. Nanoprecipitation

In nanoprecipitation, the polymer and nucleic acids are co-dissolved in a selected, water-miscible solvent, for example DMSO, acetone, ethanol, acetone, etc. In a preferred embodiment, nucleic acids and polymer are dissolved in DMSO. The solvent containing the polymer and nucleic acids is then drop-wise added to an excess volume of stirring aqueous phase containing a stabilizer (e.g., poloxamer, Pluronic®, and other stabilizers known in the art). Particles are formed and precipitated during solvent evaporation. To reduce the loss of polymer, the viscosity of the aqueous phase can be increased by using a higher concentration of the stabilizer or other thickening agents such as glycerol and others known in the art. Lastly, the entire dispersed system is centrifuged, and the nucleic acid-loaded polymer particles are collected and optionally filtered. Nanoprecipitation-based techniques are discussed in, for example, U.S. Pat. No. 5,118,528.

Advantages to nanoprecipitation include: the method can significantly increase the encapsulation efficiency of drugs that are polar yet water-insoluble, compared to single or double emulsion methods (Alshamsan, *Saudi Pharmaceutical Journal*, 22(3):219-222 (2014)). No emulsification or high shear force step (e.g., sonication or high-speed homogenization) is involved in nanoprecipitation, therefore preserving the conformation of nucleic acids. Nanoprecipitation relies on the differences in the interfacial tension between the solvent and the nonsolvent, rather than shear stress, to produce particles. Hydrophobicity of the drug will retain it in the instantly-precipitating particles; the un-precipitated polymer due to equilibrium is "lost" and not in the precipitated particle form.

B. Exemplary Particle Formulations

The particle formulation can be selected based on the considerations including the targeted tissue or cells. A preferred particle formulation is PLGA or PACE.

Other preferred particle formulations, particularly preferred for treating cystic fibrosis, are described in McNeer, et al., *Nature Commun.*, 6:6952. doi: 10.1038/ncomms7952 (2015), and Fields, et al., *Adv Healthc Mater.*, 4(3):361-6 (2015). doi: 10.1002/adhm.201400355 (2015) Epub 2014. Such particles are composed of a blend of Poly(beta-amino) esters (PBAEs) and poly(lactic-co-glycolic acid) (PLGA). Poly(beta-amino) esters (PBAEs) are degradable, cationic polymers synthesized by conjugate (Michael-like) addition of bifunctional amines to diacrylate esters (Lynn, Langer R, editor. *J Am Chem Soc.* 2000. pp. 10761-10768). PBAEs appear to have properties that make them efficient vectors for gene delivery. These cationic polymers are able to condense negatively charged pDNA, induce cellular uptake, and buffer the low pH environment of endosomes leading to DNA escape (Lynn, Langer R, editor. *J Am Chem Soc.* 2000. pp. 10761-10768, and Green, *Acc Chem Res.*, 41(6):749-759 (2008)). PBAEs have the ability to form hybrid particles with other polymers, which allows for production of solid, stable and storable particles. For example, blending cationic PBAE with PLGA produced highly loaded pDNA particles. The addition of PBAE to PLGA resulted in an increase in gene transfection in vitro and induced antigen-specific tumor rejection in a murine model (Little, et al. *Proc Natl Acad Sci USA.*, 101:9534-9539 (2004), Little, et al., *J Control Release*, 107:449-462 (2005)).

X. Methods of Use

A. Methods of Treatment The methods most typically include in utero delivery of at least one active agent to an embryo or fetus in need thereof. In some embodiments, the methods of administration are used to deliver an active agent such as a therapeutic, nutritional, diagnostic, or prophylactic agents.

The active agents can be small molecule active agents or biomacromolecules, such as proteins, polypeptides, or nucleic acids. In some embodiments, two or more active agent are delivered using an in utero delivery method. In particular embodiments, at least one of the active agents is a gene editing technology.

The active agent is typically administered in an effective amount to a subject in need thereof. The effective amount or therapeutically effective amount can be a dosage sufficient to treat, inhibit, or alleviate one or more symptoms of a disease or disorder, or to otherwise provide a desired pharmacologic and/or physiologic effect, for example, reducing, inhibiting, or reversing one or more of the underlying pathophysiological mechanisms underlying a disease or disorder.

A composition including active agent can be administered to a specific location, organ, or tissue of the fetus or embryo. The composition can have a defined release profile. In some embodiments the composition is incapable of crossing the placenta. When two or more active agents are used, the agents or their particles can have the same targeting agent, or different targeting agents, wherein the different targeting agents are capable of specifically binding to the same or different targets on or in the fetus or embryo. When two or more compositions are used, the release profiles for the different active agents can be the same or different.

The compositions can be administered or otherwise contacted with target cells once, twice, or three time daily; one, two, three, four, five, six, seven times a week, one, two, three, four, five, six, seven or eight times a month. For example, in some embodiments, the composition is administered every two or three days, or on average about 2 to about 4 times about week.

In some Examples below, for in uterine delivery by injection of alginate particles, each fetus received 30 µL of 20 mg/mL alginate microparticles suspended in PBS. For the arm treated with bFGF alone, bFGF was diluted to match the expected concentration of bFGF in the Alginate-HSA-bFGF, which was approximately 0.4 µg/L or 12 µg per injection.

In other embodiments, dosages are expressed in mg/ml, particularly when expressed as an ex vivo dosage of active agent such a growth factor or gene editing composition packaged in a particle with or without functional molecules. Dosages can be, for example 0.01 mg/ml to about 100 mg/ml, or about 0.5 mg/ml to about 50 mg/ml, or about 1 mg/ml to about 10 mg/ml per dose to a cell population of $10^6$ cells.

Dosage units including an effective amount of the compositions are also provided. The dosage can be lower than the effective dosage of the same composition when administered to treat the fetus after birth, as a child, or as an adult. The dosage can be effective to treat or prevent a disease or disorder in the fetus.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions, solutions or emulsions that can include suspending agents, solubilizers, thickening agents, dispersing agents, stabilizers, and preservatives. Formulations for injection may be presented in unit dosage form, e.g., in ampules or in multi-dose containers, optionally with an added preservative. The compositions may take such forms as sterile aqueous or non-aqueous solutions, suspensions and emulsions, which can be isotonic with the blood of the subject in certain embodiments. Examples of nonaqueous solvents are polypropylene glycol, polyethylene glycol, vegetable oil such as olive oil, sesame oil, coconut oil, arachis oil, peanut oil, mineral oil, injectable organic esters such as ethyl oleate, or fixed oils including synthetic mono or di-glycerides. Aqueous carriers include water, alcoholic/aqueous solutions, emulsions or suspensions, including saline and buffered media. Parenteral vehicles include sodium chloride solution, 1,3-butandiol, Ringer's dextrose, dextrose and sodium chloride, lactated Ringer's or fixed oils. Intravenous vehicles include fluid and nutrient replenishers, and electrolyte replenishers (such as those based on Ringer's dextrose). Preservatives and other additives may also be present such as, for example, antimicrobials, antioxidants, chelating agents and inert gases. In addition, sterile, fixed oils are conventionally employed as a solvent or suspending medium. For this purpose any bland fixed oil including synthetic mono- or di-glycerides may be employed. In addition, fatty acids such as oleic acid may be used in the preparation of injectables. Carrier formulation can be found in Remington's Pharmaceutical Sciences, Mack Publishing Co., Easton, Pa. Those of skill in the art can readily determine the various parameters for preparing and formulating the compositions without resort to undue experimentation.

In some embodiments, the compositions include pharmaceutically acceptable carriers with formulation ingredients such as salts, carriers, buffering agents, emulsifiers, diluents, excipients, chelating agents, fillers, drying agents, antioxidants, antimicrobials, preservatives, binding agents, bulking agents, silicas, solubilizers, or stabilizers.

B. Methods of Administration i. In Utero Administration

In some embodiments the route of administration is via an intravenous or intra-amniotic injection or infusion. The compositions can be administered during in utero surgery. The experiments below show that administration of nanoparticulate compositions to fetal mice results in particle retention within the fetuses with no detectable particle accumulation in the maternal mouse.

Thus, the methods can used to deliver effective amounts of compositions to the embryo or fetus, or cells thereof, without delivering an effective amount of the composition of the mother of the embryo or fetus, or her cells. In some methods the compositions can be administered by injection or infusion intravascularly into the vitelline vein, or umbilical vein, or an artery such as the vitelline artery of an embryo or fetus. In the experiments described below, intra-vitelline vein delivery of fluorescent PLGA nanoparticles (NPs) resulted in widespread fetal particle distribution at both E15.5 and E16.5 with the most abundant NP accumulation in the fetal liver. It is believed that the substantial accumulation of NPs in the fetal liver observed occurs because extraembryonic vitelline veins anastomose to form the portal circulation.

Additionally (to injection into the vitelline vein) or alternatively, the same or different compositions can be administered by injection or infusion into the amniotic cavity. During physiologic mammalian fetal development, the fetus breaths amniotic fluid into and out of the developing lungs, providing the necessary forces to direct lung development and growth. Developing fetuses additionally swallow amniotic fluid, which aids the formation of the gastrointestinal tract. The experiments below show that introduction of a nanoparticulate composition into the amniotic fluid at gestational ages after the onset of fetal breathing and swallowing resulted in delivery to the lung and gut, respectively, with increased intensity of accumulation at the later gestational ages, while administration before the onset of fetal breathing and swallowing did not lead to any detectable particle accumulation within the fetus.

The methods can be carried out at any time it is technically feasible to do so and the method are efficacious.

Fetal surgeons and maternal fetal medicine physicians can safely access the amniotic cavity for amniocentesis and cannulate umbilical vessels for fetal blood transfusions under ultrasound guidance as early as 13 weeks of gestation in humans (Bang, et al., *Br Med J* (Clin Res Ed), 284, 373-374 (1982), Kempe et al., *Ultrasound Obstet Gynecol*, 29, 226-228 (2007)). Under current medical guidelines, amniocentesis can be performed safely at 15 to 20 weeks of gestation. These procedures have been used in clinical practice since the 1980's and carry a very low risk of fetal loss (~1%) (Bang, et al., *Br Med J* (Clin Res Ed), 284, 373-374 (1982), Van Kamp, et al., *Am J Obstet Gynecol*, 192, 171-177 (2005)). These procedures can be utilized for in utero delivery of the compositions in human and other animals. An injection involves a tiny puncture in the amniotic membrane; and the therapy could be delivered earlier and with relatively low risk of premature labor and fetal loss.

In a human, the process of injection can be performed in a manner similar to amniocentesis, during which an ultrasound-guided needle is inserted into the amniotic sac to withdraw a small amount of amniotic fluid for genetic testing. A glass pipette is an exemplary needle-like tool amenable for shape and size modification for piercing through the amniotic membrane via a tiny puncture, and dispensing formulation into the utero. In some of the Examples below, a pulled glass pipette with approximately 60 micron tip, 30 microliters of suspended microparticles are injected into the amniotic space surrounding the rat fetuses. Dimensions of the tool to deliver formulation into the amniotic space are variable depending on the subject. The uterus is then returned to its normal position within the abdomen, and the pregnant dam's abdominal wall is closed.

The composition can be administered to a fetus, embryo, or to the mother or other subject when the fetus or embryo is about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36 weeks of age.

In some embodiments, the methods are carried out at a gestational time point during which agents can be safely delivered via the umbilical vessels. In some methods in utero administration is carried out on or after the gestational equivalent of E15, E15.5, or E16 of a mouse (e.g., a human or mammal's gestational age equivalent to murine gestational age E15, E15.5, or E16). Typically intraamniotic injection is carried out on or after the gestational equivalent of E16 or E16.5, or on or after fetal breathing and/or swallowing has begun.

In other embodiments, intraamniotic injection is carried out on or after the gestational equivalent of E14, E15, E16, E17, E18, E19, E20, or E21 of a rat (e.g., a human or other mammal's gestational age equivalent to rat gestational age E14, E15, E16, E17, E18, E19, E20, or E21).

The compositions can be administered before damage has occurred or when only limited damage has occurred. In some embodiments, the compositions are administered before nerve damage occurs, (e.g., the limbs of the fetus or embryo are still moving).

The formulations may be delivered using a bioerodible implant by way of diffusion or by degradation of the polymeric matrix. In certain embodiments, the administration of the formulation may be designed so as to result in sequential exposures to the composition, over a certain time period, for example, hours, days, weeks, months or years. This may be accomplished, for example, by repeated administrations of a formulation or by a sustained or controlled release delivery system in which the compositions are delivered over a prolonged period without repeated administrations. Maintaining a substantially constant concentration of the composition may be preferred in some cases.

Other delivery systems suitable include time-release, delayed release, sustained release, or controlled release delivery systems. Such systems may avoid repeated administrations in many cases, increasing convenience to the subject and the physician. Many types of release delivery systems are available and known to those of ordinary skill in the art. They include, for example, polymer-based systems such as polylactic and/or polyglycolic acids, polyanhydrides, polycaprolactones, copolyoxalates, polyesteramides, polyorthoesters, polyhydroxybutyric acid, and/or combinations of these. Microcapsules of the foregoing polymers containing nucleic acids are described in, for example, U.S. Pat. No. 5,075,109. Other examples include non-polymer systems that are lipid-based including sterols such as cholesterol, cholesterol esters, and fatty acids or neutral fats such as mono-, di- and triglycerides; hydrogel release systems; liposome-based systems; phospholipid based-systems; silastic systems; peptide based systems; wax coatings; compressed tablets using conventional binders and excipients; or partially fused implants. Specific examples include erosional systems in which the oligonucleotides are contained in a formulation within a matrix (for example, as described in U.S. Pat. Nos. 4,452,775, 4,675,189, 5,736,152, 4,667,013, 4,748,034 and 5,239,660), or diffusional systems in which an active component controls the release rate (for example, as described in U.S. Pat. Nos. 3,832,253, 3,854,480, 5,133,974 and 5,407,686). The formulation may be as, for example, microspheres, hydrogels, polymeric reservoirs, cholesterol matrices, or polymeric systems. In some embodiments, the system may allow sustained or controlled release of the composition to occur, for example, through control of the diffusion or erosion/degradation rate of the formulation containing the triplex-forming molecules and donor oligonucleotides. In addition, a pump-based hardware delivery system may be used to deliver one or more embodiments.

Examples of systems in which release occurs in bursts include systems in which the composition is entrapped in liposomes which are encapsulated in a polymer matrix, the liposomes being sensitive to specific stimuli, e.g., temperature, pH, light or a degrading enzyme and systems in which the composition is encapsulated by an ionically-coated microcapsule with a microcapsule core degrading enzyme. Examples of systems in which release of the inhibitor is gradual and continuous include, e.g., erosional systems in which the composition is contained in a form within a matrix and effusional systems in which the composition permeates at a controlled rate, e.g., through a polymer. Such sustained release systems can be in the form of pellets, or capsules.

Use of a long-term release implant may be particularly suitable in some embodiments. "Long-term release," as used herein, means that the implant containing the composition is constructed and arranged to deliver therapeutically effective levels of the composition for at least 30 or 45 days, and preferably at least 60 or 90 days, or even longer in some cases. Long-term release implants are well known to those of ordinary skill in the art, and include some of the release systems described above.

C. Diseases to Be Treated

The formulations can be delivered in a minimally invasive fashion through an intra-amniotic injection or intravenous injection. The methods can be performed throughout gestation. Intra-amniotic injection has an adverse event profile similar to amniocentesis and IA pharmacotherapy.

The Examples below show that delivery FGF growth factor in utero can correct a pathology associated with spina bifida. In some embodiments, repair of the MMC defect before secondary intrauterine nerve damage occurs is more beneficial than open fetal repair at 23 weeks gestational age. By inducing a skin or soft tissue water-tight covering of the defect early in development, MMC is converted into spina bifida occulta or at least secondary nerve injury is prevented until definitive postnatal repair can be performed. As spina bifida occulta is usually asymptomatic, this conversion could effectively be a cure for the devastating sequelae of spina bifida. Medical kits are also disclosed. The medical kits can include, for example, a dosage supply of gene editing technology or a potentiating agent thereof, or a combination thereof in separately or together in the same admixture. The active agents can be supplied alone (e.g., lyophilized), or in a pharmaceutical composition. The active agents can be in a unit dosage, or in a stock that should be diluted prior to administration. In some embodiments, the kit includes a supply of pharmaceutically acceptable carrier. The kit can also include devices for administration of the active agents or compositions, for example, syringes. The kits can include printed instructions for administering the compound in a use as described above.

In the preferred embodiment, the kit for injection into the amniotic sac of a fetus having exposed neural tissue includes polymeric microparticles having a diameter between 5 and 10 microns and a zeta potential between −32.8 and −47 mV on the surface, the polymeric microparticles having as the sole active agent fibroblast growth factor encapsulated, entrapped, complexed to or dispersed in the microparticles which is released in amniotic fluid to cause epithelial tissue to form over the exposed spinal cord or brain tissue of an embryo or fetus having exposed spinal cord or brain tissue, wherein the microparticles are formed of alginate or a polymer, copolymer or polymer blend selected from the group consisting of poly(lactic acid) (PLA), poly(glycolic acid)(PGA), poly(lactide-co-glycolide)(PLGA), polyanhydrides, poly(ortho)esters, poly(caprolactone), poly(hydroxyalkanoates), poly(lactide-co-caprolactone), poly(beta-amino)esters(PBAEs) and poly(amine-co-esterpolymers (PACE), wherein the composition is formulated for infusion or injection into the amniotic sac, and optionally, a needle for delivery of the microparticle formulation into the amniotic sac. In the preferred embodiment, the microparticles are in a concentration between 0.01 mg/ml to about 100 mg/ml, about 0.5 mg/ml to about 50 mg/ml, or about 1 mg/ml to about 10 mg/ml, and the microparticles have a loading of FGF per mg of particles releasing picograms of FGF into the amniotic fluid. In the most preferred embodiment the polymer, copolymer or polymer blend is poly(lactic acid) (PLA), poly(glycolic acid)(PGA), poly(lactide-co-glycolide) (PLGA), or alginate, having a negative surface charge.

EXAMPLES

Example 1: Intra-Amniotic Delivery in a Rat Myelomeningocele Model to Determine the Effect of Particle Properties on Binding to MMC Defect Myelomeningocele (MMC), or open spina bifida, is a devastating spinal birth defect that results in lifelong neurological morbidity. As the most severe form of spina bifida, MMC leads to lifelong lower body paralysis, bowel and bladder dysfunction. According to one study referenced by the Centers for Disease Control (CDC), the medical costs for MMC patients in the first year of life ranged from a median of $21,937 to a maximum of $1.35 million in 2012. The estimated annual cost of care for spina bifida patients in the United States in 1989 was $775 million, which would equal about $1.45 billion in today's dollars. The incidence of spina bifida is approximately 1 in 2000 to 2500 live births in the United States. This does not take into account the estimated 63% of MMC pregnancies in which the fetus is aborted, either spontaneously or intentionally. For mothers who have already given birth to one child with a neural tube defect, there is an approximately 4% risk that the next child will have spina bifida. For parents who have at least two children with neural tube defects, the risk of spina bifida in subsequent pregnancies increases to 10%.

The majority of spina bifida defects are found in the lower back, but defects can exist essentially anywhere along the spine, including the upper back and neck. Individual defects can vary significantly from patient to patient, and the term "spina bifida" encompasses a spectrum of open spinal defects. Patients with the mildest form of the anomaly, spina bifida occulta, have an open defect in the boney vertebral arches that normally protect the underlying spinal cord. Despite having this boney defect, these patients are usually neurologically normal, with no signs or symptoms except for a small dimple or tuft of hair overlying the defect. On the other end of the spectrum, patients with myelomeningocele (MMC), or open spina bifida, have no skin or soft tissue covering the boney defect along with posterior herniation of a developmentally abnormal spinal cord and meninges. Without any soft tissue or skin covering, the spinal cord is dangerously exposed to physical and chemical damage from the amniotic environment. Patients with MMC are usually born with paralysis of the lower body along with bowel and bladder dysfunction.

Prenatal diagnosis of MMC can be made as early as the first trimester using routine ultrasound surveillance. Since the advent of routine prenatal ultrasound, physicians have noticed that fetuses with MMC are able to move their legs as early as 16 weeks in gestation, but the patients' lower limb movements diminish gradually over the course of pregnancy. Based upon this observation, MMC experts have formulated a "two-hit" disease model in order to better explain the pathophysiology of MMC. The primary insult takes place during the 4th week of gestation when the caudal neuropore fails to close properly. As the fetus continues to grow, this defect in the caudal neural tube results in open exposure of the distal spinal cord. Secondary injury to the spinal cord occurs as it is exposed to intrauterine chemical and mechanical stresses over the course of gestation. The combined primary and secondary "hits" to the spinal cord result in lower extremity paralysis with bowel and bladder dysfunction by the time of birth in the majority of patients.

In addition, loss of hydrostatic pressure from leakage of cerebral spinal fluid (CSF) through the MMC defect results in herniation of the hindbrain (cerebellum) through the foramen magnum of the skull, a condition known as Chiari II malformation. The Chiari hindbrain malformation causes obstruction of CSF flow from brain to spinal column, and the CSF obstruction results in a condition known as hydrocephalus, in which there is rapid increase in head size and intracranial pressure from accumulated CSF. Even with standard post-natal closure of the defect, approximately 80% of MMC patients will require a permanent ventriculoperitoneal (VP) shunt to drain the excess CSF from the brain into the abdominal cavity. Despite improved multi-disciplinary care, the neonatal mortality rate for MMC patients remains as high as 10%, and only approximately half of those who survive will be able to function independently as adults. As always, the best "treatment" for MMC is prevention, and folate diet supplementation at the turn of the 21st century appears to have decreased the prevalence of all neural tube defects by 21 to 35%. Still, despite large-scale folate supplementation, neural tube defects remain fairly common.

Current options for a pregnant woman faced with a prenatal diagnosis of MMC are termination, delivery and postnatal repair, or fetal surgery. Though prenatal surgery increases the number of patients with MMC who can walk, the results show that, even after the stress and enormous undertaking of prenatal surgery, approximately 60% of the patients still cannot walk. Another significant disadvantage to fetal surgery is a higher rate of premature birth and premature rupture of membranes. Though fetal surgery for MMC has resulted in significant medical advancements, it is expensive, somewhat inaccessible, resource intensive, and potentially dangerous for both mother and fetus.

The current standard of care is postnatal surgical reconstruction to cover the exposed spina elements and prevent infection and further spinal damage. Some centers have started performing prenatal surgery to cover the defect with adjacent skin and muscle, but this prenatal surgery is incredibly costly, very high risk for fetus and mother, highly restricted, and still leaves around 60% of patients unable to walk independently. Therefore, myelomeningocele remains a fairly common, devastating, and expensive problem for which there is no low-risk, inexpensive, effective, widely applicable treatment.

Materials and Methods

Previous studies have established a reproducible MMC model in Sprague-Dawley rats. Pregnant Sprague-Dawley rats were fed all-trans retinoic acid, and this produces MMC defects in approximately 90% of the rat's offspring. Time-dated pregnant rats were gavage fed all-trans retinoic acid on day 10 of gestation to induce MMC. The control group received no further intervention. On day 18, groups 2, 3, 4 and 5 underwent laparotomy and intra-amniotic (IA) injections of various particles. Group 2 received poly(lactic-co-glycolic acid) (PLGA) nanoparticles (NPs) loaded with coumarin-6 (C6) fuorescent dye. Group 3 received alginate microparticles (MPs) loaded with bovine serum albumin (BSA) and Texas Red® dye. Group 4 received green fuorescent polystyrene MPs modified with terminal carboxyl groups (COOH), and Group 5 received unmodified green fuorescent polystyrene MPs.

All groups were sacrificed 3 hours after injections, and fetuses were examined under a fluorescence stereomicroscope. Images were analyzed with the Fiji image processing program. MMC defect-to-skin mean brightness ratios (MBR) were calculated using data from image overlays of equal area and analyzed by ANOVA with Tukey multiple comparisons test.

Preparation of Particles

Alginate microparticles loaded with bFGF were resuspended in phosphate buffered saline and sonicated.

PRONOVA Sterile Alginate was purchased from NovaMatrix (Sandvika, Norway) and used in all experiments. Microparticles were fabricated. Briefly, alginate and hypromellose (Sigma-Aldrich) were dissolved in ultrapure water in a 10:1 (w/w) ratio to create a 1.25% alginate solution. Alginate was completely dissolved in an incubated orbital shaker under gentle agitation, at which time the protein cargo, either recombinant human bFGF (Creative Biomart, New York) stabilized with human serum albumin (HSA) or bovine serum albumin (BSA) conjugated to Texas Red® (BSA-TR) (ThermoFisher), was dissolved in the alginate solution. HSA has been shown to be well tolerated in rats and nude mice without evidence of allergy or anaphylaxis. Once combined, the alginate/protein solution was added dropwise into a homogenizing solution of iso-octane (Fischer) and 5% Span 80 (EMD Millipore) (v/v). Next, 30% Tween 80 (Sigma), 700 mM $CaCl_2$) (Sigma) crosslinking solution, and isopropyl alcohol (AmericanBIO) were successively added to the homogenizing solution. After mixing, the solution was transferred to a new tube and washed twice in isopropyl alcohol. Following the final wash, the remaining alcohol was evaporated under a sterile air stream. The alginate particle pellet was then suspended in ultrapure water, aliquoted, flash frozen, and lyophilized for 24 hr until dry. Goal protein concentrations were 1% TR-BSA (w/w alginate) and 1.5% bFGF (w/w alginate). All particles were stored at −20° C. until use. Particle size was measured with dynamic light scattering and surface charge (zeta potential) was measured in solution using a Malvern Zetasizer (Malvern Instruments, UK).

PLGA nanoparticles were loaded with the hydrophobic fluorescent dye, coumarin 6 (C6), to track the delivery and uptake of nanoparticles (NPs) in fetal tissues after intra-amniotic (IA) administration. PLGA (50:50 ester-terminated, 0.95-1.2 g/dl, LACTEL absorbable polymers; Birmingham, AL) NPs containing C6 (Sigma; St Louis, MO) were synthesized using a previously described single-emulsion solvent evaporation technique. C6 was added to the polymer solution at a 0.2% (w/w) dye-to-polymer ratio. Dynamic light scattering (DLS) was performed to measure the NP size (hydrodynamic diameter) and surface charge (zeta potential) using a Malvern Nano-ZS (Malvern Instruments, UK).

Green fluorescent polystyrene microparticles (MPs) with (PS—COOH) and without (PS-plain) carboxyl surface groups were purchased from Phosphorex (Hopkinton, MA). The average diameter for both types of PS MPs was 10 μm, and they had a concentration of 10 mg/mL in de-ionized water with a small amount of surfactant and 2 mM sodium azide. These polystyrene particles were used without any modification. Surface charge (zeta potential) was measured in solution using a Malvern Zetasizer (Malvern Instruments, UK).

Injection and Binding Assay

Time-dated pregnant Sprague-Dawley dams were gavage fed ATRA at 60 mg/kg or 40 mg/kg on E10 to induce MMC, as described above. Control and ATRA-exposed dams between 14 and 21 days post-conception were anesthetized with inhaled isoflurane (3% v/v for induction, 2% v/v for maintenance). The gravid uterus was exposed through a midline laparotomy incision. For the binding specificity studies, lyophilized PLGA-C6 and Alg-BSA-TR were resuspended by vortex and water bath sonication in 1× Dulbecco's phosphate-buffered saline (DPBS) to concentrations of 9 mg/mL (PLGA) and 18 mg/mL (Alg-BSA-TR). Polystyrene MPs (PS—COOH and PS-plain) were used at a concentration of 10 mg/mL. All particles were drawn up into a glass micropipette (tip diameter ~60 m) and 20 μL injected directly into the amniotic cavity of each fetus using a pneumatic micro-injector (Narishige; Japan). Glass pipettes were pulled, cut, and ground. When injections were complete, the uterus was returned to the abdominal cavity, and the dam's abdominal wall fascia and skin were each closed with a running layer of 5-0 PDS II suture. During recovery, dams were placed in their cages over heating pads with easy access to water and chow, and they were monitored until they were awake and alert. For the PLGA, Alg-BSA-TR, and polystyrene studies, ATRA-exposed dams and wild type controls were sacrificed via chamber-inhaled carbon dioxide 3 hours after injections were completed. The uterus was exposed again, and individual fetuses were dissected free from the uterus within their amniotic sacks. Quality injection assurance was performed by observing the whole amniotic sac under a fluorescence microscope (Leica Microsystems, Wetzlar, Germany). If the amniotic fluid fluoresced under appropriate filter (e.g. green filter for C6), particles were considered to be successfully delivered into the amniotic space.

Imaging and Measurements Ex vivo fetal imaging of MMC defects was performed on a Leica M80 fluorescence stereomicroscope (Wetzlar, Germany). Images were analyzed using Fiji imaging software downloaded from the NIH website. Images from the fluorescence stereomicroscope were analyzed using the Fiji image processing program, and MMC defect-to-skin brightness ratios were calculated using raw integrated pixel densities from image overlays of equal area (400×400 pixel squares). MMC defect-to-skin brightness ratios for all groups were compared using one-way analysis of variance (ANOVA) and Tukey multiple comparisons test.

Amniotic Fluid Analysis

Amniotic fluid was obtained from fetal specimens ranging in age from E16.5 to E21. The amniotic fluid samples were centrifuged at 2000 rpm for 10 minutes to remove any blood clots. Rat/mouse bFGF levels were determined for untreated MMC specimens at age E16.5, E17.5, E18.5, and E21 using a Quantikine® ELISA kit (R&D Systems; Minneapolis, MN). Human bFGF concentration was measured in untreated MMC and Alg-HSA-bFGF treated MMC specimens at E21 using a Legend Max® Human FGF-basic ELISA Kit (BioLegend; San Diego, CA).

Results

All dams (N=6) and fetuses (n=57) were viable at the time of sacrifice. PLGA NPs (p=0.0461), alginate MPs (p<0.0001), and polystyrene-COOH MPs (p<0.0001) had significantly higher defect-to-skin brightness ratios compared to controls.

FIG. 20 shows specific and robust MMC defect binding was achieved by polystyrene-COOH MPs (MBR=2.139, 95% confidence interval, CI, 1.768-2.510), as well as alginate MPs (MBR=1.957, 95% CI 1.44-2.48) and PLGA NPs (MBR=1.61, 95% CI 1.34-1.88). Unmodified polystyrene MPs (PS-plain) had the weakest (p=0.9796) and least specific binding (MBR=1.18, 95% CI 1.07-1.30) compared to the non-injected controls (MBR=1.09, 95% CI 1.013-1.168).

Alginate particles were approximately 4.752+/-42 microns in diameter with a zeta potential of -35.3+/-2.5 mV. The PS—COOH particles were approximately 10 microns in diameter with a zeta potential of -47 mV. PS-plain particles were 10 microns in diameter with a zeta potential of -40 mV.

In short, intra-amniotic delivery of biodegradable alginate and PLGA particles to the MMC defect was feasible and did not cause immediate complications in rats. Polystyrene-COOH MPs, alginate MPs and PLGA NPs showed preferential binding to the MMC defect compared to surrounding skin. Specific binding to the MMC defect might be related to negative zeta potential or terminal functional groups. Preferential binding of biodegradable MPs and NPs to the MMC defect allows for targeted delivery of encapsulated therapeutic agents.

Open spina bifida, or MMC, is a devastating anomaly which affects approximately 4000 live births in the United States each year. Many affected neonates survive into adulthood and require full-time care in addition to multiple surgical procedures to correct hydrocephalus, bowel dysfunction, bladder dysfunction, decubitus ulcers, or other associated problems. Therefore, given that spina bifida is the most common neural tube defect, the condition can be very expensive at both personal and societal levels. Though it has shown promising results, fetal surgery is maximally invasive, highly exclusive (excludes 80% of patients screened), expensive, and fraught with risk for both mother and fetus. Attempts at less invasive laparoscopic and fetoscopic interventions have yet to yield results as promising as open fetal surgery, and they involve increased physiologic stress. Furthermore, it seems that even fetal MMC repair is performed too late to adequately preserve exposed neural tissue.

Recent studies in rats and sheep have shown that a gelatin sponge scaffold impregnated with bFGF can encourage ingrowth of skin with partial or even complete coverage of the spinal cord with new skin in some cases. However, in order to place a gelatin scaffold over an MMC defect, one would have to perform fetoscopy or open fetal surgery, and thus the treatment would still be invasive. Experiments were designed to determine whether it would be possible to achieve similar results in a less invasive way through the injection of biodegradable particles carrying therapeutic growth factors. Nano- and microparticles can be engineered to target specific tissue either by surface modification or antibody conjugation. Experiments were designed to investigate whether any particles could be appropriate vehicles for the controlled delivery of growth factors to the MMC defect. bFGF was chosen as the therapeutic growth factor. This is believed to be the first study involving the intra-amniotic injection of biodegradable particles for the delivery of growth factors to the MMC defect.

Given a high rate of spontaneous abortions and very severe defects, it was initially believed that the dose being administered was too high. Upon further investigation, it was discovered that there was a difference in the way in which the ATRA-olive oil was prepared. The investigators in a previous study measured out the amount of ATRA according to each individual dam's weight and suspended that amount of ATRA in 2 mL of olive oil. Due to the logistics of the gavage process, the exact dose of ATRA for each individual dam was not easy to determine before adding it to the olive oil. In order to streamline the process, the total weight of ATRA per vial was measured and suspended in a volume of olive oil required to create a stock solution of 12 mg/mL ATRA in olive oil. The volume administered per dose was then altered according to the dam's weight to achieve the appropriate total ATRA dose. When the dose was decreased to 40 mg/kg, isolated MMC yields around 90% were immediately achieved, and therefore, this dose was used for the remainder of the experiments. The exact reason or reasons for the difference in caudal regression and exencephaly rates was not identified, but it might have been related to the nutritional makeup of the chow. Nevertheless, the isolated MMC specimens resembled those of prior studies on gross examination and histology.

A determination of which biodegradable particles were best for delivering therapeutic agents to the fetal MMC defect was made. Initial experiments included the intra-amniotic injection of PLGA particles encapsulating coumarin-6 green fluorescent dye. Interestingly, without any modifications, the PLGA particles appeared to bind preferentially to the MMC defect of E21 fetuses. E21 is almost full term, and so therapeutic injections were preformed earlier in gestation in order to allow time for tissue growth. Therefore, intra-amniotic injections of PLGA-C6 were performed in fetuses ranging in age from E14 to E18. After qualitative analysis under the fluorescence stereomicroscope, it appeared that the PLGA-C6 particles bound most specifically to the MMC defect at E18 and slightly less specifically at E17. This MMC binding specificity was not nearly as pronounced at age E16 and younger perhaps due to the inherent qualities of the more immature epidermis. E18 was selected as the proper time point to testpreferential particle binding.

Alginate microparticles, were also included in the study. PLGA-C6 NPs were compared to Alg-BSA-TR MPs in E18 fetuses and both bound specifically to the MMC defect. Alginate MPs bound slightly more specifically to the MMC defect compared to PLGA NPs.

To investigate why particles preferentially bind to the MMC defect, polystyrene MPs of known size with and without surface carboxyl groups were tested. Given that the particles with more negative zeta potential (PS—COOH vs PS-plain) bound more specifically to the defect, it is possible that either terminal COOH groups, negative zeta potential, or both characteristics lead to improved binding specifically to the MMC defect. Alginate MPs are rich in COOH groups and have a negative zeta potential, and therefore, it is possible that these characteristics of alginate particles contribute to better MMC defect binding compared to PLGA.

Example 2: Intra-Amniotic Delivery of Fibroblast Growth Factor-Loaded Alginate Microparticles Materials and Methods Animal Preparation At a specific time point, pregnant rats are fed all-trans retinoic acid, and this produces MMC defects in approximately 90% of the rat's offspring. Sodium alginate microparticles are produced in the Biomedical Engineering lab and loaded with human basic fibroblast growth factor (bFGF) with a small amount of human serum albumin (HSA) added for stability. At a specific time point, the pregnant rats are placed under general anesthesia, and their uterus is exposed via midline laparotomy.

Each MMC dam was gavage fed either 60 mg/kg or 40 mg/kg of 97% pure all-trans retinoic acid (ATRA) (Across Organics; Morris Plains, NJ) dissolved in extra virgin olive oil (Whole Foods Market; Austin, TX) between 8 PM to 9 PM on gestation day E10. All wildtype dams were left alone until sacrifice. In prior studies, this method has induced MMC in fetal rats at an acceptably high rate (>80%). Early on during the study, however, high rate of caudal regression, exencephaly, and severely large MMC defects were noticed. The dose was decreased from 60 mg/kg to 40 mg/kg and achieved a 97% MMC rate at the new dose. 40 mg/kg was used for the remainder of the study.

Administration

Using a pulled glass pipette with approximately 60 micron tip, 30 microliters of suspended microparticles are injected into the amniotic space surrounding the rat fetuses. The uterus is then returned to its normal position within the abdomen, and the pregnant dam's abdominal wall is closed. In a human, this procedure would be performed in a manner similar to amniocentesis, during which a ultrasound-guided needle is inserted into the amniotic sac to withdraw a small amount of amniotic fluid for genetic testing.

Specifically, time-dated pregnant Sprague-Dawley dams at E17 and E18 were placed under general anesthesia with inhaled isoflurane (Henry Schein) (3% vol/vol for induction, 2% vol/vol for maintenance). The gravid uterus was exposed through a midline laparotomy incision. Lyophilized Alg-HSA-BFGF was re-suspended in sterile Dulbecco's PBS to a concentration of 20 mg/mL by gentle vortex and water bath sonication. The particle solution was drawn up into a glass micropipette (tip diameter ~60 m). A pneumatic microinjector (Narishige; Japan) was used to inject a volume of 30 µL into the amniotic cavity of each fetus via a ventral approach. Great care was taken to avoid inadvertently injecting into vessels, placenta, or the fetus itself, and placement of the needle tip was indirectly confirmed by a small retrograde flash of amniotic fluid into the tip immediately prior to injection. When injections were complete, the uterus was returned to the abdominal cavity, and the dam's abdominal wall fascia and skin were each closed with a running layer of 5-0 PDS II suture. During recovery, dams were placed in their cages over heating pads with easy access to water and chow, and they were monitored until they were awake and alert.

Histological Analysis

Control and injected ATRA-exposed dams were sacrificed via chamber-inhaled carbon dioxide prior to term on E21. The gravid uterus was exposed via laparotomy and removed. Great care was taken to remove each individual fetus from the uterus with its amniotic sac intact. Each fetus's amniotic sac was then removed. Ex vivo fetal imaging of MMC defects was performed on a Leica M80 fluorescence stereomicroscope (Wetzlar, Germany). Fetuses were fixed for 2 days in 4% (w/v) paraformaldehyde (Electron Microscopy Sciences; Hartfield, PA) in PBS and transferred at room temperature in 70% (v/v) ethanol in distilled water to Yale Pathology Tissue Service (YPTS) for paraffin embedding and sectioning. Cut sections were stained with hematoxylin-eosin, pancytokeratin AE1/AE3, or trichrome per YPTS protocols. Sections were obtained at 50 m intervals beginning at the superior aspect of the MMC defect and moving caudally down through the defect. The slides were imaged on a Zeiss Axio Scope (Carl Zeiss Microscopy; Germany).

Magnetic Resonance Imaging (MRI)

Wild type and control MMC fetuses were fixed in 4% PFA (w/v) in PBS for 2 weeks and delivered to the Yale Magnetic Resonance Research Center (MRRC). Each specimen was placed into a custom-built MRI-compatible tube filled with Fluorinert—an MRI susceptibility-matching fluid (Sigma-Aldrich). MR images were obtained on an 11.7 T horizontal bore scanner (Bruker, Billerica, MA) with a bore size of 21 cm and maximum gradient strength of 400 mT/m, using a custom-made 1H radio frequency volume coil (4 cm diameter). The DTI experiments were performed using an echo-planar imaging (EPI) spin-echo diffusion-weighted sequence with 4 shots, a diffusion gradient of 6 ms and a delay between the two diffusion gradients of 12 ms. 30 contiguous slices of 0.5 mm thickness were acquired at a resolution of 192×128 with a field of view of 34 mm×22 mm using a repetition time (TR) of 8 s, an echo time (TE) of 27 ms and 32 averages. 35 different images were acquired for each slice, 30 corresponding to various non-collinear diffusion gradient directions with b=1,000 s mm-2 and 5 with no diffusion gradients. Fractional anisotropy (FA) and average diffusion coefficient (ADC) images were generated from the EPI-based DTI images in BioImage Suite.

Statistical Analysis

Rat/mouse bFGF concentration data along the gestational timeline were obtained via ELISA and analyzed using ordinary one-way analysis of variance with Tukey multiple comparisons test. Adjusted P value <0.05 was considered significant. Post-injection rat/mouse and human bFGF concentration data obtained at E21 via ELISA was analyzed with a 2-tailed unpaired t-test with Welch's correction because equal standard deviations could not be assumed between groups. Adjusted P value less than 0.05 was considered significant. Defect-to-skin brightness ratio data for the fluorescence binding study was analyzed using ANOVA with Tukey multiple comparisons test. Again, an adjusted P value <0.05 was considered significant. Statistical analyses were performed using GraphPad Prism (version 7; GraphPad Software; La Jolla, CA).

Results

Alginate microparticles have been studied to deliver proteins and growth factors to specific tissues, as well as in topical delivery of drugs to chronic wounds. However, they have not been used for the controlled release delivery of growth factors to a specific area of the fetus in utero, especially the open spinal defect of a fetus with myelomeningocele.

Fetal Delivery of Alg-HSA-bFGF

Before injecting exogenous bFGF into the amniotic space, the baseline levels of detectable bFGF in rat MMC amniotic fluid was measured. To determine what the baseline bFGF level is in rat amniotic fluid at various time points around the time of the injection, rat/mouse bFGF levels for untreated MMC specimens at age E16.5, E17.5, E18.5, and E21 were obtained and as shown in FIG. 21. The level of bFGF in rat amniotic fluid increases toward full term to a mean of 67 pg/mL (range 26 to 161 pg/mL). After analyzing the data using ordinary ANOVA with Tukey multiple comparisons, the differences between E16.5 (15.8 pg/mL), E17.5 (4.1 pg/mL) and E21 (67.3 pg/mL) were found to be statistically significant (E16.5 vs E21, P=0.02; E17.5 vs E21 P=0.006).

Figure 3:
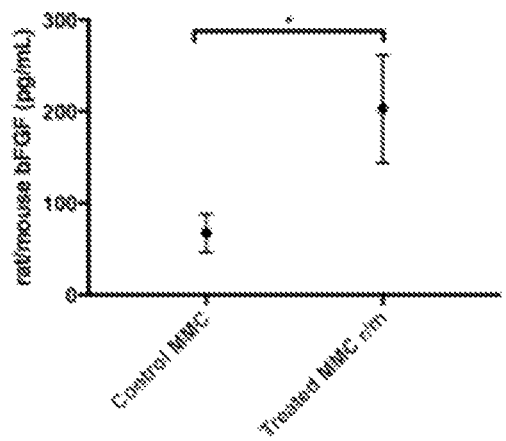
FIG. 3 is a graph showing the amount of rat/mouse bFGF (pg/mL) in treated MMCs compared to control: 202.9+/−59 pg/mL vs 67.3+/−20.9 pg/mL, p=0.041.
Figure 4:
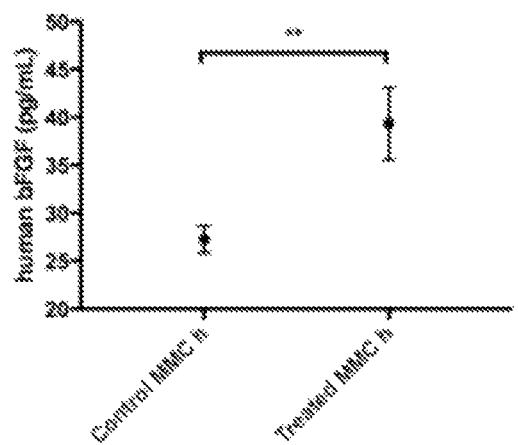
FIG. 4 is a graph showing the amount of human bFGF in amniotic fluid injected with alginate particles delivering bFGF and stabilized with human serum albumin compared to control: 39.3+/−3.8 pg/mL vs 27.3+/−1.4 pg/mL, p=0.0046.

For the Alg-HSA-bFGF study, treated MMCs had higher amniotic fluid levels of both human (39.3+/−3.8 pg/mL vs 27.3+/−1.4 pg/mL, p=0.0046) and rat/mouse bFGF (202.9+/−59 pg/mL vs 67.3+/−20.9 pg/mL, p=0.041) compared to control MMCs (FIGS. 3 and 4). Obtaining amniotic fluid via needle aspiration is difficult toward the end of gestation due to the increasing fetus-to-amniotic fluid ratio. By E21, the amniotic fluid is so low that there is no visible target for needle aspiration, and the fluid must be obtained by opening the amniotic sac and allowing the small amount that remains to drain out. Despite the challenge in obtaining enough amniotic fluid per specimen, values of both rat/mouse and human bFGF were obtained in control MMC and injected MMC specimens. The control MMC bFGF amniotic fluid concentrations ranged from 0 to 161 pg/mL, and the levels appeared to increase significantly toward full term.

Next, the amount of rat/mouse and human bFGF were measured in control and injected MMC fetuses. The levels of both human and rat/mouse bFGF were significantly higher in the injected amniotic fluid vs the control fluid at day E21. While the human bFGF level was approximately 12 ng/mL higher in the injected specimens compared to control, the rat/mouse bFGF level was approximately 135 ng/mL higher in the injected amniotic fluid by E21 (p=0.04). The reason for the larger increase in rat/mouse bFGF over human bFGF is not clear, but may be related to a host inflammatory response to the injections. The user manual of the rat/mouse QUANTIKINE® ELISA kit states that its detection antibody cross-reacts with human recombinant bFGF, but the extent of cross-reactivity is not made clear in the user manual provided by the company. Also, according to the user manual included in the LEGEND Max™ human bFGF ELISA kit, it should not detect rat/mouse bFGF. Therefore, the fact that the control human bFGF level is higher than zero indicates a high background, and this high background could be due to user error or a faulty kit.

All dams that underwent laparotomy and IA injections with Alginate-HSA-bFGF, blank Alginate, Alginate-BSA-TR, bFGF alone and PBS were alive at the time of sacrifice (N=22). 150 of 239 fetuses (62.8%) that received IA injections at E17.5 were viable at E21. Fetal loss between the time of injection and sacrifice was not significantly higher in any group that received injections. Un-injected specimens (0 of 24, 0%), those injected with PBS (0 of 13, 0%) and those injected with bFGF alone (0 of 42, 0%) showed no coverage of the defect. Of the remaining control groups, 2 of 18 (11%) treated with Alginate-BSA-TR and 3 of 19 (16%) treated with Alginate-Blank appeared to have at least partial coverage of the MMC defect. Fluorescent stereomicroscopy of the MMC specimen treated with Alginate-BSA-TR revealed positive red fluorescence throughout a layer of tissue covering the defect with negligible fluorescent signal from surrounding normal skin. This finding suggests that the alginate particles aggregated specifically over the MMC defect and likely accomplished cellular or paracellular delivery of fluorescently tagged BSA. On histological analysis of the same specimen, the red fluorescent layer of tissue over the MMC defect had the appearance of abnormal, hyperkeratotic and partially formed skin.

Gross and histomorphological differences were also discovered between the control MMCs and several of the treated specimens. Even on gross analysis, 7 out of 34 (20.6%) of the injected specimens observed appeared noticeably smaller with opaque rinds overlying the exposed nerve tissue. Although smaller defects might be the result of natural variation among the MMC defects; the analyses of a large number of untreated fetal rat MMC specimens have not revealed any similar results on either gross or histological analysis.

Following injection of particles loaded with growth factor, Alginate-HAS-bFGF, 18 of 61 (30%) fetuses treated with Alginate-HSA-bFGF had evidence of soft tissue coverage that was significant compared to un-injected (P=0.0021), PBS (P=0.0297), and bFGF controls (P<0.0001). Histological analysis of specimens treated with Alginate-HSA-bFGF that were positive for tissue coverage on gross inspection also showed complete skin covering over the spinal cord.

Slides were stained with trichrome and a pan cytokeratin (AE1/AE3) immunohistochemical stain. Trichrome is excellent for visualizing normal skin as well as collagen in the dermis and subdermal tissue. The immunohistochemistry AE1/AE3 stain is a cocktail of antibodies against cytokeratin found in epithelial cells. In the skin, AE1/AE3 specifically stains the epidermis, eccrine glands, and folliculosebaceous-apocrine unit. The AE1/AE3 stain was used in a previously published study which used bFGF-impregnated gelatin sponges to grow new skin-like tissue over the defect.

In control MMC slide images, the 2 flattened and exposed hemicords were identified, adjacent thin epithelia layer, and the normal appearing skin located far from the nerve tissue. None of the control slides stained strongly for AE1/AE3, especially not within the epithelial tissues surrounding the cord. For the treated specimens, it was immediately apparent that there was abnormal-appearing skin covering the spinal cord more inferiorly within the defect, as compared to the control. Additionally, one of the specimens appeared to have a thick film overlying both the new skin and the spinal cord. The film appeared to be composed of scattered red blood cells, some nucleated cells, and spherical empty structures consistent with alginate particles. The overall structure seemed benign (it washed away during the preparation of pan cytokeratin AE1/AE3 slides). Moreover, the extremely positive staining of pan cytokeratin AE1/AE3 directly over the spinal cord indicates that those areas of skin are relatively new or at least producing excess keratins compared to the normal skin at the periphery of the slides. In sum, with trichrome staining and analysis at the same level within the MMC defect, the treated MMCs appeared to have a layer of abnormal skin covering the spinal cord, whereas the control spinal cord was flattened and completely exposed. In addition, treated specimens stained strongly for pan cytokeratin AE1/AE3 specifically in the area of the skin covering the spinal cord while the control did not have significantly increased staining in the area of the defect or the skin immediately surrounding it. This skin is notably different than the native skin that has lower levels of pan cytokeratin staining and the absence of hair follicles. Moreover, treated specimens did not have significant staining within the skin distant from the MMC defect.

Put together, the pan cytokeratin staining pattern suggests that the skin seen overlying the spinal cord in these treated specimens is new, growing rapidly, over-producing keratins, or all of the above.

Fetal MRI for the Microstructural Analysis Of Fetal MMC

Micro MRI scans were completed for 4 wild type and 4 control MMC specimens, from which Diffusion Tensor Imaging (DTI) images were produced. With DTI imaging, software can be used to assign colors (red, green, or blue) to identify the direction of a water diffusion vector in plane x, y, or z. There were differences in the passive diffusion of water throughout the spinal cord and the brain. The spinal cord of the MMC specimen was almost entirely red, which indicated a significant passive diffusion of water in the cranio-caudal direction. Meanwhile, the wild type specimen had a markedly thinner stripe of red in the center of its cord, perhaps identifying the passive diffusion of water along the central canal. Altogether, there are marked differences between wild type and untreated MMC specimens on DTI images.

CONCLUSION

Intra-amniotic injection of biocompatible PLGA and alginate particles is feasible and safe in the immediate peri-injection period. Both PLGA and alginate bind preferentially to the MMC defect compared to the fetal skin, and this preferential binding is best at gestation day E17.5 to E18. Negative zeta potential and/or surface carboxyl groups might be factors that improve binding to the MMC defect. Although PLGA and alginate particles bind to the MMC defect without any surface modifications, future attempts at improved MP targeting with surface group modifications or antibody conjugation might allow for more optimal delivery of bFGF to the MMC defect. Intra-amniotic injection of Alg-HSA-bFGF microparticles at gestational ages E17 to E18 leads to the growth of new skin over the MMC defect in the ATRA-induced rat MMC model.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. A method comprising administering by injection into the amniotic fluid of a 15 to 20 week human embryo or fetus having exposed spinal cord or brain tissue, an effective amount of a composition comprising fibroblast growth factor encapsulated, entrapped, complexed to or dispersed in polymeric microparticles having a diameter from about 5 to about 10 microns and a zeta potential between −32.8 and −47 mV to cause epithelial tissue to form over the exposed spinal cord or brain tissue in the embryo or fetus, wherein the microparticles are formed of alginate, poly(lactic acid) (PLA), poly(glycolic acid)(PGA), poly(lactide-co-glycolide)(PLGA), polyanhydrides, poly(ortho) esters, poly(caprolactone), poly(hydroxyalkanoates), poly(lactide-co-caprolactone), poly(beta-amino) esters (PBAEs) or poly(amine-co-ester) polymers(PACE).

2. The method of claim 1, wherein the microparticles are formed of poly(lactic acid)(PLA), poly(glycolic acid) (PGA), poly(lactide-co-glycolide)(PLGA), polyanhydrides, poly(ortho)esters, poly(caprolactone), poly(hydroxyalkanoates), poly(lactide-co-caprolactone), poly(beta-amino)esters (PBAEs) or poly(amine-co-ester)polymers (PACE).

3. The method of claim 2, wherein the microparticles are formed of polylactide-co-glycolide (PLGA).

4. The method of claim 1, wherein the microparticles are formed of alginate encapsulating the fibroblast growth factor.

5. The method of claim 1 wherein the composition is administered into the amniotic fluid of the embryo or fetus having exposed spinal cord.

6. The method of claim 1 wherein the composition is injected using an ultrasonic guided needle inserted into the amniotic sac.

7. The method of claim 1 wherein the fetus or embryo is human and is about 14, 15, 16, or 17 weeks of age.

8. The method of claim 1 wherein the microparticles release an amount of fibroblast growth factor to produce picogram levels of fibroblast growth factor in the amniotic fluid.

9. A kit comprising
a composition comprising polymeric microparticles having a diameter between 5 and 10 microns and a zeta potential between −32.8 and −47 mV, the polymeric microparticles having as the sole active agent fibroblast growth factor encapsulated, entrapped, complexed to or dispersed in the microparticles,
wherein the microparticles are formed of alginate, poly(lactic acid)(PLA), poly(glycolic acid)(PGA), poly(lactide-co-glycolide)(PLGA), polyanhydrides, poly(ortho)esters, poly(caprolactone), poly(hydroxyalkanoates), poly(lactide-co-caprolactone), poly(beta-amino)esters(PBAEs) or poly(amine-co-ester)polymers(PACE),
wherein the composition is formulated for infusion or injection into the amniotic sac, and
a needle for delivery of the microparticle formulation into the amniotic sac.

10. The kit of claim 9 wherein the microparticles are in a concentration between 0.01 mg/ml to about 100 mg/ml, about 0.5 mg/ml to about 50 mg/ml, or about 1 mg/ml to about 10 mg/ml.

11. The kit of claim 9 wherein the microparticles have a loading of FGF per mg of particles releasing picograms of FGF into the amniotic fluid.

12. The kit of claim 9 wherein the microparticles are formed of poly(lactic acid) (PLA), poly(glycolic acid) (PGA), poly(lactide-co-glycolide)(PLGA), or alginate.

13. The kit of claim 9 comprising dosage units of 5-10 micron poly(lactic acid)(PLA), poly(glycolic acid)(PGA), or poly(lactide-co-glycolide)(PLGA) microparticles having a loading of fibroblast growth factor producing picogram levels of FGF in the amniotic fluid.

* * * * *